US005378822A

United States Patent [19]

Bradfield et al.

[11] Patent Number: 5,378,822
[45] Date of Patent: Jan. 3, 1995

[54] NUCLEIC ACIDS ENCODING MURINE AND HUMAN AH RECEPTORS

[75] Inventors: Christopher A. Bradfield; Kristin M. Dolwick, both of Chicago, Ill.; Alan Poland, Madison, Wis.

[73] Assignees: Wisconsin Alumni Research, Evanston, Ill.; Northwestern University & Foundation, Madison, Wis.

[21] Appl. No.: 45,806

[22] Filed: Apr. 8, 1993

[51] Int. Cl.$^6$ ..................... C07H 21/02; C07H 21/04
[52] U.S. Cl. .................................. 536/23.5; 536/23.1; 536/24.3; 536/24.31
[58] Field of Search ................... 536/23.5; 435/6, 91.2

[56] References Cited

PUBLICATIONS

Lee et al., Science 239, 1288–1291 (1988).
Blackwood et al., "Max: A Helix-Loop-Helix Zipper Protein That Forms a Sequence Secific DNA Binding Complex with Myc", Science, 251: 1211–1217 (1991).
Bradfield et al., "Purification and N-Terminal Amino Acid Sequence of the Ah Receptor from the C57BL/6J Mouse," Mol. Pharm., 39: 13–19 (1991).
Burbach et al., "Cloning of the Ah Receptor cDNA Reveals a Distinctive Ligand Activated Transcription Factor," Proc. Acad. Sci., 89: 8185–8189 (1992).
Chirgwin et al., "Isolation of Biologically Active Ribonucleic Acid from Sources Enriched in Riobnuclease," Biochem., 18: 5294–5299 (1979).
Chrambach et al., "A Procedure for Rapid and Sensitive Stainng of Protein Fractionated by Polyacrylamide Gel Electrophoresis," Ana. Biochem., 20: 150–154 (1967).
Courey et al., "Analysis of Sp1 in Vivo Reveals Multiple Transcriptonal Domains, including a Novel Glutamine-Rich Actuation Motif," Cell, 55:887–898 (1988).
Dension et al., "Protein-DNA Interactions at Recognition Sides for the Dioxin-Ah Receptor Complex," J. of Bio. Chem.
Durrin et al., "2, 3, 7, 8–Tetrachlorodibenzo–p–Dioxin Receptors Regulate Transcription of the Cytochrome P$_1$–450 Gene," J. of Cell. Biochem., 35:153–160 (1987).
Elferink et al., "Protein-DNA Interactions at a Dioxin-Responsive Enhancer," J. of Bio. Chem., 265:20708–20712 (1990).
Ema et al., "cDNA Cloning and Structure of Mouse Putative Ah Receptor," Biochem. and Biophy. Research Comm., 184:246–253 (1992).
Michael a. Frohman, "Race: Rapid Amplification of cDNA Ends," in PCR Protocols: A Guide to Methods and Applications, (Academic Press, Inc., San Diego, 1990), pp. 28–38.
Gerster, "The Cell Type-Specific Octamer Transcription Factor OTF-2 has Two Domains Required for the Actuation of Transcription," EMBO J., 9:1635–1643 (1990).
Hankison, Oliver, "Dominant and Recessive Aryl Hydrocarbon Hydroxylase—Deficient Mutants of Mouse Hepatoma Line, Hepa–1, and Assignment of Recessive Mutants to Three Complementation Groups," Somatic Cell Genetics, 9: 497–514 (1983).

(List continued on next page.)

Primary Examiner—Margaret Parr
Assistant Examiner—Kenneth R. Horlick
Attorney, Agent, or Firm—Tilton, Fallon, Lungmus & Chestnut

[57] ABSTRACT

Murine and human Ah-receptor cDNAs are provided. These molecules can be used to generate large quantities of Ah-receptor protein for use in competitive binding assays for detecting environmental pollutants. Also, the murine and human cDNAs can be used in the generation of recombinant organisms that can serve as biomonitors for environmental pollutants or in regulating gene expression for receptor agonists. Additionally, the cDNAs can be used to detect human and wildlife populations that have high susceptibility to environmental pollutants and polyacrylic aromatic hydrocarbons.

4 Claims, 14 Drawing Sheets

PUBLICATIONS

Hanson et al., "Administration's 1992 Budget Proposes a Healthy Boost for R&D," *Chemical Engineering News*, 7–13, (1991).

Heukeshoven et al., "Simplified Method for Silver Staining of Proteins in Polyacrylamide Gels and the Mechanism of Silver Staining," *Electrophoresis*, 6:103–112 (1985).

Hewick et al., "A Gas-Liquid Solid Phase Peptide and Protein Sequentor," *J. of Bio. Chem.*, 256:7990–7997 (1981).

Hoffman et al., "Cloning of a factor Required for Activity of the Ah (Dioxin) Receptor," *Science*, 252:954–958 (1991).

Israel et al., "Induction of mRNA Specific for Cytochrome $P_1$–450 in Wild Type and Variant Mouse Hepatoma Cells," *J. of Bio. Chem.*, 258:10390–10394 (1983).

Jones et al., "Biochemical and Genetic Analysis of Variant Mouse Hepatoma Cells Which Overtranscribe the Cytochrome $P_1$–450 Gene in Response to 2,3,7,8-Tetrachlorodibenzo-p-Dioxin," *J. Bio Chem.*, 259:12357–12363 (1984).

Kohler et al., "Continuous Cultures of Fused Cells Secreting Antibody of Predefined Specificity," *Nature*, 256:495–497 (1975).

Marilyn Kozak, "An Analysis of 51-Noncoding Sequences from 699 Vertebrate Messenger RNAs," *Nuclear Acids Research*, 15:8125–8132 (1987).

Laemmli, U. K., "Cleavage of Structural Proteins During the Assembly of the Head of Bacteriphage T4," *Nature*, 227:680–685 (1970).

Laurent et al., "The SNF5 protein of *Saccharomyces cerevisiae* is a Glutamine and Proline-Rich Transcriptional Activator that Affects Expression of a Broad Spectrum of Genes," *Mole. and Cell Bio.*, 10: 5616–5625 (1990).

Miller et al., "Biochemical and Genetic Analysis of Variant Mouse Hepatoma Cells Defective in the Induction of Benzo(a)pyrene-metabolizing Enzyme Activity," *J. of Bio. Chem.*, 258:3523–3527 (1983).

Nambu et al., "The Drosophila Single-Minded Gene Encodes a Helix-Loop-helix Protein that Acts as a Master Regulator of CNS Midline Developement," *Cell*, 67:1157–1167 (1991).

Nebert et al., "P450 Genes: Structure, Evolution, and Regulation," *Ann. Rev. Biochem.*, 56:945–93 (1987).

Newhold et al., "Regulation of Mouse CYP1A1 Gene Expression by Dioxin: Requirement of Two cis-acting Elements During Induction," *Mol. and Cell. Bio.*, 9:2378–2386 (1989).

Okey, "Detection and Characterization of a Low Affinity Form of Cytosolic Ah Receptor in Livers of Mice Non-Responsive to Induction of Cytochrome $P_1$–456 by 3-Methylcholanthrene," *Mol. Phar.*, 35:823–830 (1989).

Gary H. Perdew I, "Association of the Ah Receptor with the 90 kDA Heat Shock Protein," *J. of Bio. Chem.*, 263:13802–13805 (1988).

Perdew II et al., "Analysis of Photoaffinity-Labeled Aryl Hydrocarbon Receptor Heterogeneity by Two Dimensional Gel Electrophoresis," *Biochem.* 29:6210–6214 (1990).

Poland I et al., "Genetic Expression of Aryl Hydrocarbon Hydroxylase by 2, 3, 7, 8-Tetrachlorodibenzo-p-dioxin: Evidence for a Receptor Mutation in Genetically Non-Responsive Mice," *Mol. Pharm.*, 11: 389–398 (1975).

Poland II et al., "2, 3, 7, 8-Tetrachlorodibenzo-p-dioxin and Related Halogenated Aromatic Hydrocarbons: Examination of the Mechanism of Toxicity," *Ann. Rev. Pharmacol. Toxicol.*, 22:517–54 (1982).

Poland III et al., "Photoaffinity Labeling of the Ah Receptor," *J. of Bio. Chem.*, 261:6352–6365 (1986).

Poland IV et al., "Variation in the Molecular Mass of the Ah Receptor Among Vertebrate Species and Strains of Rats," *Biochemical and Biophysical Research Communications*, 146:1438–1449 (1987).

Poland V et al., "Characterization of Polyclonal Antibodies to the Ah Receptor Prepared by immunization with a Synthetic Peptide Hapten," *Mol. Pharm.*, 39:20–26 (1991).

Pongratz I et al., "Dual Roles of the 90 kDA heat Shock protein hsp 90 in Modulating Functional Activities of the Dioxin receptor," *J. of Bio. Chem.*, 267:13728–12734 (1992).

Pongratz II et al., "Inhibition of the Specific DNA Binding Activity of the Dioxin Receptor of Phosphatase Treatment," *J. of Bio. Chem.*, 266:16813–16817 (1991).

(List continued on next page.)

PUBLICATIONS

Reyes et al., "Identification of the Ah Receptor Nuclear Translocator Protein (Arnt) as a Component of the DNA Binding Form of the Ah Receptor," *Science*, 256:1193-1195 (1992).

Sadowski et al., "A Vector for Expressing GAL4 (1-147) Fusions in Mammalian Cells," *Nucleic Acids Research*, 17:7539 (1989).

Stephen Safe, "Polychlorinated Biphenyls (PCBs), Dibenzo-p-Dioxins (PCDDS), Dibenzofurans (PCDFs), and Related Compounds: Environmental and Mechanistic Considerations Which Support the Development of Toxic Equivalency Factors (TEFs)," *Crt. Rev. Tox.*, 21: 51-88 (1990).

Sanger et al., "DNA Sequencing with Chain-Terminating Inhibitors," *Proc. Natl. Acad. Sci. USA*, 74:5463-5467 (1977).

Schagger et al., "Tricine–Sodium Dodecyl Sulfate–Polyacrylamide Gel Electrophoresis for the Separation of Proteins in the Range from 1 to 100 kDa," *Ana. Bio.* 166:368-379 (1987).

Short et al., "ZAP: A Bacteriophage Expression Vector with in Vivo Excision Properties," *Nucleic Acids Research*, 16:7583-7600 (1988).

Telakowski, "Glutathione s-transferase Ya Subunit Gene. Identification of Regulator of Elements Required for basal Level and Inducible Expression," *Proc. Natl Acad. Sci. USA* 85:1000-1004 (1988).

Weintraub et al., "The myoD Gene Family: Nodal Point During Specification of the Muscle Cell Lineage," *Science*, 251:761-766 (1991).

Wharton et al., "opa: A Novel Family of Transcribed Repeats Shared by the Notch Locus and Other Developmentally Regulated Loc, in D. Melanogaster," *Cell*, 40:55-62 (1985).

HELIX-LOOP-HELIX DOMAINS

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 3207 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 1..2415

( x i ) SEQUENCE DESCRIPTION: SEQ ID NO:1:

```
ATG AGC AGC GGC GCC AAC ATC ACC TAT GCC AGC CGC AAG CGG CGC AAG        48
Met Ser Ser Gly Ala Asn Ile Thr Tyr Ala Ser Arg Lys Arg Arg Lys
 1               5                  10                  15

CCG GTG CAG AAA ACA GTA AAG CCC ATC CCC GCT GAA GGA ATT AAG TCA        96
Pro Val Gln Lys Thr Val Lys Pro Ile Pro Ala Glu Gly Ile Lys Ser
             20                  25                  30

AAT CCT TCT AAG CGA CAC AGA GAC CGG CTG AAC ACA GAG TTA GAC CGC       144
Asn Pro Ser Lys Arg His Arg Asp Arg Leu Asn Thr Glu Leu Asp Arg
         35                  40                  45

CTG GCC AGC CTG CTG CCC TTC CCG CAA GAT GTT ATT AAT AAG CTG GAC       192
Leu Ala Ser Leu Leu Pro Phe Pro Gln Asp Val Ile Asn Lys Leu Asp
     50                  55                  60

AAA CTC TCT GTT CTT AGG CTC AGC GTC ACG TAC CTG AGG GCC AAG AGC       240
Lys Leu Ser Val Leu Arg Leu Ser Val Thr Tyr Leu Arg Ala Lys Ser
 65                  70                  75                  80

TTC TTT GAT GTT GCA TTA AAG TCC ACC CCT GCT GAC AGA AAT GGA GGC       288
Phe Phe Asp Val Ala Leu Lys Ser Thr Pro Ala Asp Arg Asn Gly Gly
                 85                  90                  95

CAG GAC CAG TGT AGA GCA CAA ATC AGA GAC TGG CAG GAT TTG CAA GAA       336
Gln Asp Gln Cys Arg Ala Gln Ile Arg Asp Trp Gln Asp Leu Gln Glu
            100                 105                 110

GGA GAG TTC TTG TTA CAG GCG CTG AAT GGC TTT GTG CTG GTT GTC ACA       384
Gly Glu Phe Leu Leu Gln Ala Leu Asn Gly Phe Val Leu Val Val Thr
        115                 120                 125

GCA GAT GCC TTG GTC TTC TAT GCT TCC TCC ACT ATC CAA GAT TAC CTG       432
Ala Asp Ala Leu Val Phe Tyr Ala Ser Ser Thr Ile Gln Asp Tyr Leu
    130                 135                 140

GGC TTT CAG CAG TCT GAT GTC ATC CAT CAG AGC GTA TAT GAG CTC ATC       480
Gly Phe Gln Gln Ser Asp Val Ile His Gln Ser Val Tyr Glu Leu Ile
145                 150                 155                 160

CAT ACA GAA GAC CGG GCG GAA TTC CAG CGC CAG CTT CAC TGG GCT CTA       528
His Thr Glu Asp Arg Ala Glu Phe Gln Arg Gln Leu His Trp Ala Leu
                165                 170                 175

AAC CCA GAC TCT GCA CAA GGA GTG GAC GAA GCC CAT GGC CCT CCA CAG       576
Asn Pro Asp Ser Ala Gln Gly Val Asp Glu Ala His Gly Pro Pro Gln
            180                 185                 190

GCA GCA GTC TAT TAT ACC CCA GAC CAG CTT CCT CCA GAG AAC GCT TCT       624
Ala Ala Val Tyr Tyr Thr Pro Asp Gln Leu Pro Pro Glu Asn Ala Ser
        195                 200                 205

TTC ATG GAG AGG TGC TTC AGG TGC CGG CTG AGG TGC CTG CTG GAT AAT       672
Phe Met Glu Arg Cys Phe Arg Cys Arg Leu Arg Cys Leu Leu Asp Asn
    210                 215                 220

TCA TCT GGT TTT CTG GCA ATG AAT TTC CAA GGG AGG TTA AAG TAT CTT       720
Ser Ser Gly Phe Leu Ala Met Asn Phe Gln Gly Arg Leu Lys Tyr Leu
225                 230                 235                 240

CAT GGA CAG AAC AAG AAA GGG AAG GAC GGA GCG CTG CTT CCT CCA CAA       768
His Gly Gln Asn Lys Lys Gly Lys Asp Gly Ala Leu Leu Pro Pro Gln
                245                 250                 255

CTG GCT TTG TTT GCA ATA GCT ACT CCA CTT CAG CCA CCC TCC ATC CTG       816
Leu Ala Leu Phe Ala Ile Ala Thr Pro Leu Gln Pro Pro Ser Ile Leu
```

|   |   |   |   |   |   |   |   |   |   |   |   |   |   |   |   |   |
|---|---|---|---|---|---|---|---|---|---|---|---|---|---|---|---|---|
| GAA | ATT | CGA | ACC | AAA | AAC | TTC | ATC | TTC | AGG | ACC | AAA | CAC | AAG | CTA | GAC | 864 |
| Glu | Ile | Arg | Thr | Lys | Asn | Phe | Ile | Phe | Arg | Thr | Lys | His | Lys | Leu | Asp | |
| | | 275 | | | | | 280 | | | | | 285 | | | | |
| TTC | ACA | CCT | ATT | GGT | TGT | GAT | GCC | AAA | GGG | CAG | CTT | ATT | CTG | GGC | TAT | 912 |
| Phe | Thr | Pro | Ile | Gly | Cys | Asp | Ala | Lys | Gly | Gln | Leu | Ile | Leu | Gly | Tyr | |
| | 290 | | | | | 295 | | | | | 300 | | | | | |
| ACA | GAA | GTA | GAG | CTG | TGC | ACA | AGA | GGA | TCG | GGG | TAC | CAG | TTC | ATC | CAT | 960 |
| Thr | Glu | Val | Glu | Leu | Cys | Thr | Arg | Gly | Ser | Gly | Tyr | Gln | Phe | Ile | His | |
| 305 | | | | | 310 | | | | | 315 | | | | | 320 | |
| GCT | GCA | GAC | ATA | CTT | CAC | TGT | GCA | GAA | TCC | CAC | ATC | CGC | ATG | ATT | AAG | 1008 |
| Ala | Ala | Asp | Ile | Leu | His | Cys | Ala | Glu | Ser | His | Ile | Arg | Met | Ile | Lys | |
| | | | | 325 | | | | | 330 | | | | | 335 | | |
| ACT | GGA | GAA | AGT | GGC | ATG | ACA | GTT | TTC | CGG | CTT | CTT | GCA | AAA | CAC | AGT | 1056 |
| Thr | Gly | Glu | Ser | Gly | Met | Thr | Val | Phe | Arg | Leu | Leu | Ala | Lys | His | Ser | |
| | | | 340 | | | | | 345 | | | | | 350 | | | |
| CGC | TGG | AGG | TGG | GTC | CAG | TCC | AAT | GCA | CGC | TTG | ATT | TAC | AGA | AAT | GGA | 1104 |
| Arg | Trp | Arg | Trp | Val | Gln | Ser | Asn | Ala | Arg | Leu | Ile | Tyr | Arg | Asn | Gly | |
| | | 355 | | | | | 360 | | | | | 365 | | | | |
| AGA | CCA | GAT | TAC | ATC | ATC | GCC | ACT | CAG | AGA | CCA | CTG | ACG | GAT | GAA | GAA | 1152 |
| Arg | Pro | Asp | Tyr | Ile | Ile | Ala | Thr | Gln | Arg | Pro | Leu | Thr | Asp | Glu | Glu | |
| | 370 | | | | | 375 | | | | | 380 | | | | | |
| GGA | CGA | GAG | CAT | TTA | CAG | AAG | CGA | AGT | ACG | TCG | CTG | CCC | TTC | ATG | TTT | 1200 |
| Gly | Arg | Glu | His | Leu | Gln | Lys | Arg | Ser | Thr | Ser | Leu | Pro | Phe | Met | Phe | |
| 385 | | | | | 390 | | | | | 395 | | | | | 400 | |
| GCT | ACC | GGA | GAG | GCT | GTG | TTG | TAC | GAG | ATC | TCC | AGC | CCT | TTC | TCT | CCC | 1248 |
| Ala | Thr | Gly | Glu | Ala | Val | Leu | Tyr | Glu | Ile | Ser | Ser | Pro | Phe | Ser | Pro | |
| | | | | 405 | | | | | 410 | | | | | 415 | | |
| ATA | ATG | GAT | CCC | CTA | CCA | ATA | CGC | ACC | AAA | AGC | AAC | ACT | AGC | AGG | AAA | 1296 |
| Ile | Met | Asp | Pro | Leu | Pro | Ile | Arg | Thr | Lys | Ser | Asn | Thr | Ser | Arg | Lys | |
| | | | 420 | | | | | 425 | | | | | 430 | | | |
| GAC | TGG | GCT | CCC | CAG | TCA | ACC | CCA | AGT | AAG | GAT | TCT | TTC | CAC | CCC | AGT | 1344 |
| Asp | Trp | Ala | Pro | Gln | Ser | Thr | Pro | Ser | Lys | Asp | Ser | Phe | His | Pro | Ser | |
| | | 435 | | | | | 440 | | | | | 445 | | | | |
| TCT | CTT | ATG | AGT | GCC | CTC | ATC | CAG | CAG | GAT | GAG | TCC | ATC | TAT | CTG | TGT | 1392 |
| Ser | Leu | Met | Ser | Ala | Leu | Ile | Gln | Gln | Asp | Glu | Ser | Ile | Tyr | Leu | Cys | |
| | 450 | | | | | 455 | | | | | 460 | | | | | |
| CCT | CCT | TCA | AGC | CCT | GCG | CTG | TTA | GAC | AGC | CAT | TTT | CTC | ATG | GGC | TCC | 1440 |
| Pro | Pro | Ser | Ser | Pro | Ala | Leu | Leu | Asp | Ser | His | Phe | Leu | Met | Gly | Ser | |
| 465 | | | | | 470 | | | | | 475 | | | | | 480 | |
| GTG | AGC | AAG | TGC | GGG | AGT | TGG | CAA | GAC | AGC | TTT | GCG | GCC | GCA | GGA | AGT | 1488 |
| Val | Ser | Lys | Cys | Gly | Ser | Trp | Gln | Asp | Ser | Phe | Ala | Ala | Ala | Gly | Ser | |
| | | | | 485 | | | | | 490 | | | | | 495 | | |
| GAG | GCT | GCG | CTG | AAA | CAT | GAG | CAA | ATT | GGC | CAT | GCT | CAG | GAC | GTG | AAC | 1536 |
| Glu | Ala | Ala | Leu | Lys | His | Glu | Gln | Ile | Gly | His | Ala | Gln | Asp | Val | Asn | |
| | | | 500 | | | | | 505 | | | | | 510 | | | |
| CTT | GCA | CTC | TCT | GGC | GGC | CCC | TCA | GAG | CTC | TTT | CCG | GAT | AAT | AAA | AAT | 1584 |
| Leu | Ala | Leu | Ser | Gly | Gly | Pro | Ser | Glu | Leu | Phe | Pro | Asp | Asn | Lys | Asn | |
| | | 515 | | | | | 520 | | | | | 525 | | | | |
| AAT | GAC | TTG | TAC | AGC | ATC | ATG | AGG | AAC | CTT | GGG | ATT | GAT | TTT | GAA | GAT | 1632 |
| Asn | Asp | Leu | Tyr | Ser | Ile | Met | Arg | Asn | Leu | Gly | Ile | Asp | Phe | Glu | Asp | |
| | 530 | | | | | 535 | | | | | 540 | | | | | |
| ATC | AGA | AGC | ATG | CAG | AAC | GAG | GAG | TTC | TTC | AGA | ACT | GAC | TCC | ACC | GCT | 1680 |
| Ile | Arg | Ser | Met | Gln | Asn | Glu | Glu | Phe | Phe | Arg | Thr | Asp | Ser | Thr | Ala | |
| 545 | | | | | 550 | | | | | 555 | | | | | 560 | |
| GCT | GGT | GAG | GTT | GAC | TTC | AAA | GAC | ATC | GAC | ATA | ACG | GAC | GAA | ATC | CTG | 1728 |
| Ala | Gly | Glu | Val | Asp | Phe | Lys | Asp | Ile | Asp | Ile | Thr | Asp | Glu | Ile | Leu | |
| | | | | 565 | | | | | 570 | | | | | 575 | | |
| ACC | TAC | GTG | CAG | GAT | TCC | CTG | AAC | AAT | TCA | ACT | TTG | CTG | AAC | TCG | GCT | 1776 |
| Thr | Tyr | Val | Gln | Asp | Ser | Leu | Asn | Asn | Ser | Thr | Leu | Leu | Asn | Ser | Ala | |
| | | | | 580 | | | | | 585 | | | | | 590 | | |

-continued

| | | | | | | | | | | | | | | | | |
|---|---|---|---|---|---|---|---|---|---|---|---|---|---|---|---|---|
| TGC | CAG | CAG | CAG | CCT | GTG | ACT | CAG | CAC | CTA | AGC | TGT | ATG | CTG | CAG | GAG | 1824 |
| Cys | Gln | Gln | Gln | Pro | Val | Thr | Gln | His | Leu | Ser | Cys | Met | Leu | Gln | Glu | |
| | | 595 | | | | | 600 | | | | | 605 | | | | |
| CGC | CTG | CAA | CTA | GAG | CAA | CAG | CAA | CAG | CTT | CAG | CAG | CCC | CCG | CCG | CAG | 1872 |
| Arg | Leu | Gln | Leu | Glu | Gln | Gln | Gln | Gln | Leu | Gln | Gln | Pro | Pro | Pro | Gln | |
| | 610 | | | | | 615 | | | | | 620 | | | | | |
| GCT | CTG | GAG | CCC | CAG | CAG | CAG | CTG | TGT | CAG | ATG | GTG | TGC | CCC | CAG | CAA | 1920 |
| Ala | Leu | Glu | Pro | Gln | Gln | Gln | Leu | Cys | Gln | Met | Val | Cys | Pro | Gln | Gln | |
| 625 | | | | 630 | | | | | 635 | | | | | | 640 | |
| GAT | CTG | GGT | CCG | AAG | CAC | ACG | CAA | ATC | AAC | GGC | ACG | TTT | GCA | AGT | TGG | 1968 |
| Asp | Leu | Gly | Pro | Lys | His | Thr | Gln | Ile | Asn | Gly | Thr | Phe | Ala | Ser | Trp | |
| | | | | 645 | | | | | 650 | | | | | | 655 | |
| AAC | CCC | ACC | CCT | CCC | GTG | TCT | TTC | AAC | TGT | CCC | CAG | CAG | GAA | CTA | AAG | 2016 |
| Asn | Pro | Thr | Pro | Pro | Val | Ser | Phe | Asn | Cys | Pro | Gln | Gln | Glu | Leu | Lys | |
| | | | 660 | | | | | 665 | | | | | | 670 | | |
| CAC | TAT | CAG | CTC | TTT | TCC | AGC | TTA | CAG | GGG | ACT | GCT | CAG | GAA | TTT | CCC | 2064 |
| His | Tyr | Gln | Leu | Phe | Ser | Ser | Leu | Gln | Gly | Thr | Ala | Gln | Glu | Phe | Pro | |
| | | 675 | | | | | 680 | | | | | 685 | | | | |
| TAC | AAA | CCA | GAG | GTG | GAC | AGT | GTG | CCT | TAC | ACA | CAG | AAC | TTT | GCT | CCC | 2112 |
| Tyr | Lys | Pro | Glu | Val | Asp | Ser | Val | Pro | Tyr | Thr | Gln | Asn | Phe | Ala | Pro | |
| | 690 | | | | | 695 | | | | | 700 | | | | | |
| TGT | AAT | CAG | CCT | CTG | CTT | CCA | GAA | CAT | TCC | AAG | AGT | GTG | CAG | TTG | GAC | 2160 |
| Cys | Asn | Gln | Pro | Leu | Leu | Pro | Glu | His | Ser | Lys | Ser | Val | Gln | Leu | Asp | |
| 705 | | | | | 710 | | | | | 715 | | | | | 720 | |
| TTC | CCT | GGA | AGG | GAT | TTT | GAA | CCG | TCC | CTG | CAT | CCC | ACT | ACT | TCT | AAT | 2208 |
| Phe | Pro | Gly | Arg | Asp | Phe | Glu | Pro | Ser | Leu | His | Pro | Thr | Thr | Ser | Asn | |
| | | | | 725 | | | | | 730 | | | | | 735 | | |
| TTA | GAT | TTT | GTC | AGT | TGT | TTA | CAA | GTT | CCT | GAA | AAC | CAA | AGT | CAT | GGG | 2256 |
| Leu | Asp | Phe | Val | Ser | Cys | Leu | Gln | Val | Pro | Glu | Asn | Gln | Ser | His | Gly | |
| | | | 740 | | | | | 745 | | | | | 750 | | | |
| ATA | AAC | TCA | CAG | TCC | GCC | ATG | GTC | AGT | CCT | CAG | GCA | TAC | TAT | GCT | GGG | 2304 |
| Ile | Asn | Ser | Gln | Ser | Ala | Met | Val | Ser | Pro | Gln | Ala | Tyr | Tyr | Ala | Gly | |
| | | 755 | | | | | 760 | | | | | 765 | | | | |
| GCC | ATG | TCC | ATG | TAT | CAG | TGC | CAG | CCA | GGG | CCA | CAG | CGC | ACC | CCT | GTG | 2352 |
| Ala | Met | Ser | Met | Tyr | Gln | Cys | Gln | Pro | Gly | Pro | Gln | Arg | Thr | Pro | Val | |
| 770 | | | | | 775 | | | | | 780 | | | | | | |
| GAC | CAG | ACG | CAG | TAC | AGC | TCT | GAA | ATT | CCA | GGT | TCT | CAG | GCA | TTC | CTA | 2400 |
| Asp | Gln | Thr | Gln | Tyr | Ser | Ser | Glu | Ile | Pro | Gly | Ser | Gln | Ala | Phe | Leu | |
| 785 | | | | | 790 | | | | | 795 | | | | | 800 | |
| AGC | AAG | GTG | CAG | AGT | TGAGGTGTTT | TCAATGAAAC | CTATTCGTCC | GACTTGAGCA | | | | | | | | 2455 |
| Ser | Lys | Val | Gln | Ser | | | | | | | | | | | | |
| | | | | 805 | | | | | | | | | | | | |

| | | | | |
|---|---|---|---|---|
| GCATTGGCCA | CGCTGCTCAG | ACCACTGGCC | ATCTCCATCA | CTGCGGAAGC | CCGGCCTCTT | 2515 |
| CCCGATATCA | CACCCGGTGG | ATTCCTGTAG | CTCCCATGCC | AGGATGAAAT | TCATTCAGGA | 2575 |
| ACAGGATACC | AGAACTGTGA | GGGTTGGACA | TCAGTACACT | TTCTCCAAAA | CAGATTTCGA | 2635 |
| TTCTTGTGTT | TAGAGAAGGA | GTTTAAAACC | CGTACCTGAG | ATGCTCCCTA | TACGATGGGA | 2695 |
| GAGCTCGGAC | GGAGCACATG | GGAGGAGTTC | AGGCACCTCA | GAGTGCACAG | TGTTTACTGT | 2755 |
| GAAAAATTCT | CGGGTTCCCT | GCTCAGTAAC | TTCAGCAGGA | AAAACAGGGA | GGTATTTGGA | 2815 |
| GCTTTGAACT | TCTGGATTCT | TGTTAGTATA | CCAAATACGG | AGTTACAGGA | CTAACCGATT | 2875 |
| TCCTATATTT | TTTAACCTCT | GTTTTGTCC | CAGAAGTTAA | AGTAAATGGT | TTGGTGCTTT | 2935 |
| TCTCAAAAGA | AAATCTCAAT | GCTTCTTTC | TGCACTGTTA | ATATAAGTGC | CTCACTTTTT | 2995 |
| GTTGTTGTTG | TTGTTGTTTT | CTGATTTTTT | TCTTTTTTTC | TATCTACCTG | TAACACAATA | 3055 |
| GGGTATGTAT | TTTATATGAA | ATATTTTTA | TCTTTTTTGA | ATTAATATTC | TTTCTGCACA | 3115 |
| AAGAAAGTTT | CCCGAATCCC | AACCTTTCTA | TGACCCCGCT | GTGTGTGTGC | ACTACTCATC | 3175 |
| CTTTCCTTCA | GATAAAGAGT | AATTGATAAC | TC | | | 3207 |

( 2 ) INFORMATION FOR SEQ ID NO:2:

( i ) SEQUENCE CHARACTERISTICS:
        ( A ) LENGTH: 805 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ser  Ser  Gly  Ala  Asn  Ile  Thr  Tyr  Ala  Ser  Arg  Lys  Arg  Arg  Lys
 1              5                        10                       15

Pro  Val  Gln  Lys  Thr  Val  Lys  Pro  Ile  Pro  Ala  Glu  Gly  Ile  Lys  Ser
              20                        25                       30

Asn  Pro  Ser  Lys  Arg  His  Arg  Asp  Arg  Leu  Asn  Thr  Glu  Leu  Asp  Arg
              35                        40                       45

Leu  Ala  Ser  Leu  Leu  Pro  Phe  Pro  Gln  Asp  Val  Ile  Asn  Lys  Leu  Asp
         50                        55                       60

Lys  Leu  Ser  Val  Leu  Arg  Leu  Ser  Val  Thr  Tyr  Leu  Arg  Ala  Lys  Ser
 65                       70                        75                       80

Phe  Phe  Asp  Val  Ala  Leu  Lys  Ser  Thr  Pro  Ala  Asp  Arg  Asn  Gly  Gly
                   85                        90                       95

Gln  Asp  Gln  Cys  Arg  Ala  Gln  Ile  Arg  Asp  Trp  Gln  Asp  Leu  Gln  Glu
              100                       105                      110

Gly  Glu  Phe  Leu  Leu  Gln  Ala  Leu  Asn  Gly  Phe  Val  Leu  Val  Val  Thr
              115                       120                      125

Ala  Asp  Ala  Leu  Val  Phe  Tyr  Ala  Ser  Ser  Thr  Ile  Gln  Asp  Tyr  Leu
         130                       135                      140

Gly  Phe  Gln  Gln  Ser  Asp  Val  Ile  His  Gln  Ser  Val  Tyr  Glu  Leu  Ile
145                       150                      155                      160

His  Thr  Glu  Asp  Arg  Ala  Glu  Phe  Gln  Arg  Gln  Leu  His  Trp  Ala  Leu
                   165                       170                      175

Asn  Pro  Asp  Ser  Ala  Gln  Gly  Val  Asp  Glu  Ala  His  Gly  Pro  Pro  Gln
              180                       185                      190

Ala  Ala  Val  Tyr  Tyr  Thr  Pro  Asp  Gln  Leu  Pro  Pro  Glu  Asn  Ala  Ser
         195                       200                      205

Phe  Met  Glu  Arg  Cys  Phe  Arg  Cys  Arg  Leu  Arg  Cys  Leu  Leu  Asp  Asn
     210                       215                      220

Ser  Ser  Gly  Phe  Leu  Ala  Met  Asn  Phe  Gln  Gly  Arg  Leu  Lys  Tyr  Leu
225                       230                      235                      240

His  Gly  Gln  Asn  Lys  Lys  Gly  Lys  Asp  Gly  Ala  Leu  Leu  Pro  Pro  Gln
              245                       250                      255

Leu  Ala  Leu  Phe  Ala  Ile  Ala  Thr  Pro  Leu  Gln  Pro  Pro  Ser  Ile  Leu
              260                       265                      270

Glu  Ile  Arg  Thr  Lys  Asn  Phe  Ile  Phe  Arg  Thr  Lys  His  Lys  Leu  Asp
              275                       280                      285

Phe  Thr  Pro  Ile  Gly  Cys  Asp  Ala  Lys  Gly  Gln  Leu  Ile  Leu  Gly  Tyr
     290                       295                      300

Thr  Glu  Val  Glu  Leu  Cys  Thr  Arg  Gly  Ser  Gly  Tyr  Gln  Phe  Ile  His
305                       310                      315                      320

Ala  Ala  Asp  Ile  Leu  His  Cys  Ala  Glu  Ser  His  Ile  Arg  Met  Ile  Lys
                   325                       330                      335

Thr  Gly  Glu  Ser  Gly  Met  Thr  Val  Phe  Arg  Leu  Leu  Ala  Lys  His  Ser
              340                       345                      350

Arg  Trp  Arg  Trp  Val  Gln  Ser  Asn  Ala  Arg  Leu  Ile  Tyr  Arg  Asn  Gly
              355                       360                      365

Arg  Pro  Asp  Tyr  Ile  Ile  Ala  Thr  Gln  Arg  Pro  Leu  Thr  Asp  Glu  Glu
```

|  |  | 370 |  |  |  |  | 375 |  |  |  |  | 380 |  |  |
|---|---|---|---|---|---|---|---|---|---|---|---|---|---|---|

Gly Arg Glu His Leu Gln Lys Arg Ser Thr Ser Leu Pro Phe Met Phe
385                    390                395                    400

Ala Thr Gly Glu Ala Val Leu Tyr Glu Ile Ser Ser Pro Phe Ser Pro
                405                410                    415

Ile Met Asp Pro Leu Pro Ile Arg Thr Lys Ser Asn Thr Ser Arg Lys
            420                425                430

Asp Trp Ala Pro Gln Ser Thr Pro Ser Lys Asp Ser Phe His Pro Ser
        435                440                445

Ser Leu Met Ser Ala Leu Ile Gln Gln Asp Glu Ser Ile Tyr Leu Cys
    450                455                460

Pro Pro Ser Ser Pro Ala Leu Leu Asp Ser His Phe Leu Met Gly Ser
465                470                475                    480

Val Ser Lys Cys Gly Ser Trp Gln Asp Ser Phe Ala Ala Ala Gly Ser
            485                490                    495

Glu Ala Ala Leu Lys His Glu Gln Ile Gly His Ala Gln Asp Val Asn
            500                505                510

Leu Ala Leu Ser Gly Gly Pro Ser Glu Leu Phe Pro Asp Asn Lys Asn
        515                520                525

Asn Asp Leu Tyr Ser Ile Met Arg Asn Leu Gly Ile Asp Phe Glu Asp
    530                535                540

Ile Arg Ser Met Gln Asn Glu Glu Phe Phe Arg Thr Asp Ser Thr Ala
545                550                555                    560

Ala Gly Glu Val Asp Phe Lys Asp Ile Asp Ile Thr Asp Glu Ile Leu
            565                570                    575

Thr Tyr Val Gln Asp Ser Leu Asn Asn Ser Thr Leu Leu Asn Ser Ala
            580                585                590

Cys Gln Gln Gln Pro Val Thr Gln His Leu Ser Cys Met Leu Gln Glu
        595                600                605

Arg Leu Gln Leu Glu Gln Gln Gln Leu Gln Gln Pro Pro Pro Gln
610                615                620

Ala Leu Glu Pro Gln Gln Gln Leu Cys Gln Met Val Cys Pro Gln Gln
625                630                635                    640

Asp Leu Gly Pro Lys His Thr Gln Ile Asn Gly Thr Phe Ala Ser Trp
            645                650                655

Asn Pro Thr Pro Pro Val Ser Phe Asn Cys Pro Gln Gln Glu Leu Lys
            660                665                670

His Tyr Gln Leu Phe Ser Ser Leu Gln Gly Thr Ala Gln Glu Phe Pro
        675                680                685

Tyr Lys Pro Glu Val Asp Ser Val Pro Tyr Thr Gln Asn Phe Ala Pro
690                695                700

Cys Asn Gln Pro Leu Leu Pro Glu His Ser Lys Ser Val Gln Leu Asp
705                710                715                    720

Phe Pro Gly Arg Asp Phe Glu Pro Ser Leu His Pro Thr Thr Ser Asn
            725                730                735

Leu Asp Phe Val Ser Cys Leu Gln Val Pro Glu Asn Gln Ser His Gly
        740                745                750

Ile Asn Ser Gln Ser Ala Met Val Ser Pro Gln Ala Tyr Tyr Ala Gly
        755                760                765

Ala Met Ser Met Tyr Gln Cys Gln Pro Gly Pro Gln Arg Thr Pro Val
        770                775                780

Asp Gln Thr Gln Tyr Ser Ser Glu Ile Pro Gly Ser Gln Ala Phe Leu
785                790                795                    800

Ser Lys Val Gln Ser
            805

( 2 ) INFORMATION FOR SEQ ID NO:3:

( i ) SEQUENCE CHARACTERISTICS:
        ( A ) LENGTH: 5261 base pairs
        ( B ) TYPE: nucleic acid
        ( C ) STRANDEDNESS: double
        ( D ) TOPOLOGY: unknown ( i i ) MOLECULE TYPE: cDNA ( i x ) FEATURE:
        ( A ) NAME/KEY: CDS
        ( B ) LOCATION: 383..2927

( x i ) SEQUENCE DESCRIPTION: SEQ ID NO:3:

```
AATTCCGCAC GGCCCAGACC CAGGATTCTT TATAGACGGC CCAGGCTCCT CCTCCGCCCG      60

GGCCGCCTCA CCTGCGGGCA TTGCGCGCCG CCTCCGCCGG TGTAGACGGC ACCTGCGCCG     120

CCTTGCTCGC GGGTCTCCGC CCTCGCCCAC CCTCACTGCG CCAGGCCCAG GCAGCTCACC     180

TGTACTGGCG CGGGCTGCGG AAGCTGCGTG ACGCGAGGCG TTGAGGCGCG CGCCCACGC      240

CACTGTCCCG AGAGGACGCA GGTGGAGCGG GCGCGACTTC GCGAACCCGG CGCCGGCCGC     300

CGCAGTGGTC CCAGCCTACA CCGGGTTCCG GGGACCCGGC CGCCAGTGCC CGGGGAGTAG     360

CCGCCGCCGT CGGCTGGGCA CC ATG AAC AGC AGC AGC GCC AAC ATC ACC TAC     412
                        Met Asn Ser Ser Ser Ala Asn Ile Thr Tyr
                         1               5                    10

GCC AGT CGC AAG CGG CGG AAG CCG GTG CAG AAA ACA GTA AAG CCA ATC      460
Ala Ser Arg Lys Arg Arg Lys Pro Val Gln Lys Thr Val Lys Pro Ile
             15                  20                  25

CCA GCT GAA GGA ATC AAG TCA AAT CCT TCC AAG CGG CAT AGA GAC CGA      508
Pro Ala Glu Gly Ile Lys Ser Asn Pro Ser Lys Arg His Arg Asp Arg
         30                  35                  40

CTT AAT ACA GAG TTG GAC CGT TTG GCT AGC CTG CTG CCT TTC CCA CAA      556
Leu Asn Thr Glu Leu Asp Arg Leu Ala Ser Leu Leu Pro Phe Pro Gln
     45                  50                  55

GAT GTT ATT AAT AAG TTG GAC AAA CTT TCA GTT CTT AGG CTC AGC GTC      604
Asp Val Ile Asn Lys Leu Asp Lys Leu Ser Val Leu Arg Leu Ser Val
 60                  65                  70

AGT TAC CTG AGA GCC AAG AGC TTC TTT GAT GTT GCA TTA AAA TCC TCC      652
Ser Tyr Leu Arg Ala Lys Ser Phe Phe Asp Val Ala Leu Lys Ser Ser
 75                  80                  85                  90

CCT ACT GAA AGA AAC GGA GGC CAG GAT AAC TGT AGA GCA GCA AAT TTC      700
Pro Thr Glu Arg Asn Gly Gly Gln Asp Asn Cys Arg Ala Ala Asn Phe
         95                  100                 105

AGA GAA GGC CTG AAC TTA CAA GAA GGA GAA TTC TTA TTA CAG GCT CTG      748
Arg Glu Gly Leu Asn Leu Gln Glu Gly Glu Phe Leu Leu Gln Ala Leu
             110                 115                 120

AAT GGC TTT GTA TTA GTT GTC ACT ACA GAT GCT TTG GTC TTT TAT GCT      796
Asn Gly Phe Val Leu Val Val Thr Thr Asp Ala Leu Val Phe Tyr Ala
         125                 130                 135

TCT TCT ACT ATA CAA GAT TAT CTA GGG TTT CAG CAG TCT GAT GTC ATA      844
Ser Ser Thr Ile Gln Asp Tyr Leu Gly Phe Gln Gln Ser Asp Val Ile
     140                 145                 150

CAT CAG AGT GTA TAT GAA CTT ATC CAT ACC GAA GAC CGA GCT GAA TTT      892
His Gln Ser Val Tyr Glu Leu Ile His Thr Glu Asp Arg Ala Glu Phe
155                 160                 165                 170

CAG CGT CAG CTA CAC TGG GCA TTA AAT CCT TCT CAG TGT ACA GAG TCT      940
Gln Arg Gln Leu His Trp Ala Leu Asn Pro Ser Gln Cys Thr Glu Ser
             175                 180                 185

GGA CAA GGA ATT GAA GAA GCC ACT GGT CTC CCC CAG ACA GTA GTC TGT      988
Gly Gln Gly Ile Glu Glu Ala Thr Gly Leu Pro Gln Thr Val Val Cys
         190                 195                 200
```

| | | | | | | | | | | | | | | | | |
|---|---|---|---|---|---|---|---|---|---|---|---|---|---|---|---|---|
| TAT | AAC | CCA | GAC | CAG | ATT | CCT | CCA | GAA | AAC | TCT | CCT | TTA | ATG | GAG | AGG | 1036 |
| Tyr | Asn | Pro | Asp | Gln | Ile | Pro | Pro | Glu | Asn | Ser | Pro | Leu | Met | Glu | Arg | |
| | | 205 | | | | | 210 | | | | | 215 | | | | |
| TGC | TTC | ATA | TGT | CGT | CTA | AGG | TGT | CTG | CTG | GAT | AAT | TCA | TCT | GGT | TTT | 1084 |
| Cys | Phe | Ile | Cys | Arg | Leu | Arg | Cys | Leu | Leu | Asp | Asn | Ser | Ser | Gly | Phe | |
| | | 220 | | | | 225 | | | | | 230 | | | | | |
| CTG | GCA | ATG | AAT | TTC | CAA | GGG | AAG | TTA | AAG | TAT | CTT | CAT | GGA | CAG | AAA | 1132 |
| Leu | Ala | Met | Asn | Phe | Gln | Gly | Lys | Leu | Lys | Tyr | Leu | His | Gly | Gln | Lys | |
| 235 | | | | | 240 | | | | | 245 | | | | | 250 | |
| AAG | AAA | GGG | AAA | GAT | GGA | TCA | ATA | CTT | CCA | CCT | CAG | TTG | GCT | TTG | TTT | 1180 |
| Lys | Lys | Gly | Lys | Asp | Gly | Ser | Ile | Leu | Pro | Pro | Gln | Leu | Ala | Leu | Phe | |
| | | | | | 255 | | | | | 260 | | | | | 265 | |
| GCG | ATA | GCT | ACT | CCA | CTT | CAG | CCA | CCA | TCC | ATA | CTT | GAA | ATC | CGG | ACC | 1228 |
| Ala | Ile | Ala | Thr | Pro | Leu | Gln | Pro | Pro | Ser | Ile | Leu | Glu | Ile | Arg | Thr | |
| | | | 270 | | | | | 275 | | | | | 280 | | | |
| AAA | AAT | TTT | ATC | TTT | AGA | ACC | AAA | CAC | AAA | CTA | GAC | TTC | ACA | CCT | ATT | 1276 |
| Lys | Asn | Phe | Ile | Phe | Arg | Thr | Lys | His | Lys | Leu | Asp | Phe | Thr | Pro | Ile | |
| | | 285 | | | | | 290 | | | | | 295 | | | | |
| GGT | TGT | GAT | GCC | AAA | GGA | AGA | ATT | GTT | TTA | GGA | TAT | ACT | GAA | GCA | GAG | 1324 |
| Gly | Cys | Asp | Ala | Lys | Gly | Arg | Ile | Val | Leu | Gly | Tyr | Thr | Glu | Ala | Glu | |
| | | 300 | | | | 305 | | | | | 310 | | | | | |
| CTG | TGC | ACG | AGA | GGC | TCA | GGT | TAT | CAG | TTT | ATT | CAT | GCA | GCT | GAT | ATG | 1372 |
| Leu | Cys | Thr | Arg | Gly | Ser | Gly | Tyr | Gln | Phe | Ile | His | Ala | Ala | Asp | Met | |
| 315 | | | | | 320 | | | | | 325 | | | | | 330 | |
| CTT | TAT | TGT | GCC | GAG | TCC | CAT | ATC | CGA | ATG | ATT | AAG | ACT | GGA | GAA | AGT | 1420 |
| Leu | Tyr | Cys | Ala | Glu | Ser | His | Ile | Arg | Met | Ile | Lys | Thr | Gly | Glu | Ser | |
| | | | | 335 | | | | | 340 | | | | | 345 | | |
| GGC | ATG | ATA | GTT | TTC | CGG | CTT | CTT | ACA | AAA | AAC | AAC | CGA | TGG | ACT | TGG | 1468 |
| Gly | Met | Ile | Val | Phe | Arg | Leu | Leu | Thr | Lys | Asn | Asn | Arg | Trp | Thr | Trp | |
| | | | 350 | | | | | 355 | | | | | 360 | | | |
| GTC | CAG | TCT | AAT | GCA | CGC | CTG | CTT | TAT | AAA | AAT | GGA | AGA | CCA | GAT | TAT | 1516 |
| Val | Gln | Ser | Asn | Ala | Arg | Leu | Leu | Tyr | Lys | Asn | Gly | Arg | Pro | Asp | Tyr | |
| | | 365 | | | | | 370 | | | | | 375 | | | | |
| ATC | ATT | GTA | ACT | CAG | AGA | CCA | CTA | ACA | GAT | GAG | GAA | GGA | ACA | GAG | CAT | 1564 |
| Ile | Ile | Val | Thr | Gln | Arg | Pro | Leu | Thr | Asp | Glu | Glu | Gly | Thr | Glu | His | |
| Ile | 380 | | | | | 385 | | | | | | 390 | | | | |
| TTA | CGA | AAA | CGA | AAT | ACG | AAG | TTG | CCT | TTT | ATG | TTT | ACC | ACT | GGA | GAA | 1612 |
| Leu | Arg | Lys | Arg | Asn | Thr | Lys | Leu | Pro | Phe | Met | Phe | Thr | Thr | Gly | Glu | |
| 395 | | | | | 400 | | | | | 405 | | | | | 410 | |
| GCT | GTG | TTG | TAT | GAG | GCA | ACC | AAC | CCT | TTT | CCT | GCC | ATA | ATG | GAT | CCC | 1660 |
| Ala | Val | Leu | Tyr | Glu | Ala | Thr | Asn | Pro | Phe | Pro | Ala | Ile | Met | Asp | Pro | |
| | | | | 415 | | | | | 420 | | | | | 425 | | |
| TTA | CCA | CTA | AGG | ACT | AAA | AAT | GGC | ACT | AGT | GGA | AAA | GAC | TCT | GCT | ACC | 1708 |
| Leu | Pro | Leu | Arg | Thr | Lys | Asn | Gly | Thr | Ser | Gly | Lys | Asp | Ser | Ala | Thr | |
| | | | 430 | | | | | 435 | | | | | 440 | | | |
| ACA | TCC | ACT | CTA | AGC | AAG | GAC | TCT | CTC | AAT | CCT | AGT | TCC | CTC | CTG | GCT | 1756 |
| Thr | Ser | Thr | Leu | Ser | Lys | Asp | Ser | Leu | Asn | Pro | Ser | Ser | Leu | Leu | Ala | |
| | | 445 | | | | | 450 | | | | | 455 | | | | |
| GCC | ATG | ATG | CAA | CAA | GAT | GAG | TCT | ATT | TAT | CTC | TAT | CCT | GCT | TCA | AGT | 1804 |
| Ala | Met | Met | Gln | Gln | Asp | Glu | Ser | Ile | Tyr | Leu | Tyr | Pro | Ala | Ser | Ser | |
| | 460 | | | | | 465 | | | | | 470 | | | | | |
| ACT | TCA | AGT | ACT | GCA | CCT | TTT | GAA | AAC | AAC | TTT | TTC | AAC | GAA | TCT | ATG | 1852 |
| Thr | Ser | Ser | Thr | Ala | Pro | Phe | Glu | Asn | Asn | Phe | Phe | Asn | Glu | Ser | Met | |
| 475 | | | | | 480 | | | | | 485 | | | | | 490 | |
| AAT | GAA | TGC | AGA | AAT | TGG | CAA | GAT | AAT | ACT | GCA | CCG | ATG | GGA | AAT | GAT | 1900 |
| Asn | Glu | Cys | Arg | Asn | Trp | Gln | Asp | Asn | Thr | Ala | Pro | Met | Gly | Asn | Asp | |
| | | | | 495 | | | | | 500 | | | | | 505 | | |
| ACT | ATC | CTG | AAA | CAT | GAG | CAA | ATT | GAC | CAG | CCT | CAG | GAT | GTG | AAC | TCA | 1948 |
| Thr | Ile | Leu | Lys | His | Glu | Gln | Ile | Asp | Gln | Pro | Gln | Asp | Val | Asn | Ser | |
| | | | 510 | | | | | 515 | | | | | 520 | | | |
| TTT | GCT | GGA | GGT | CAC | CCA | GGG | CTC | TTT | CAA | GAT | AGT | AAA | AAC | AGT | GAC | 1996 |

|   |   |   |   |   |   |   |   |   |   |   |   |   |   |   |   |
|---|---|---|---|---|---|---|---|---|---|---|---|---|---|---|---|
| Phe | Ala | Gly | Gly | His | Pro | Gly | Leu | Phe | Gln | Asp | Ser | Lys | Asn | Ser | Asp |
|     | 525 |     |     |     |     | 530 |     |     |     |     | 535 |     |     |     |     |

```
TTG TAC AGC ATA ATG AAA AAC CTA GGC ATT GAT TTT GAA GAC ATC AGA       2044
Leu Tyr Ser Ile Met Lys Asn Leu Gly Ile Asp Phe Glu Asp Ile Arg
    540             545             550

CAC ATG CAG AAT GAA AAA TTT TTC AGA AAT GAT TTT TCT GGT GAG GTT       2092
His Met Gln Asn Glu Lys Phe Phe Arg Asn Asp Phe Ser Gly Glu Val
555             560             565             570

GAC TTC AGA GAC ATT GAC TTA ACG GAT GAA ATC CTG ACG TAT GTC CAA       2140
Asp Phe Arg Asp Ile Asp Leu Thr Asp Glu Ile Leu Thr Tyr Val Gln
                575             580             585

GAT TCT TTA AGT AAG TCT CCC TTC ATA CCT TCA GAT TAT CAA CAG CAA       2188
Asp Ser Leu Ser Lys Ser Pro Phe Ile Pro Ser Asp Tyr Gln Gln Gln
            590             595             600

CAG TCC TTG GCT CTG AAC TCA AGC TGT ATG GTA CAG GAA CAC CTA CAT       2236
Gln Ser Leu Ala Leu Asn Ser Ser Cys Met Val Gln Glu His Leu His
        605             610             615

CTA GAA CAG CAA CAG CAA CAT CAC CAA AAG CAA GTA GTA GTG GAG CCA       2284
Leu Glu Gln Gln Gln Gln His His Gln Lys Gln Val Val Val Glu Pro
    620             625             630

CAG CAA CAG CTG TGT CAG AAG ATG AAG CAC ATG CAA GTT AAT GGC ATG       2332
Gln Gln Gln Leu Cys Gln Lys Met Lys His Met Gln Val Asn Gly Met
635             640             645             650

TTT GAA AAT TGG AAC TCT AAC CAA ATC GTG CCT TTC AAT TGT CCA CAG       2380
Phe Glu Asn Trp Asn Ser Asn Gln Ile Val Pro Phe Asn Cys Pro Gln
                655             660             665

CAA GAC CCA CAA CAA TAT AAT GTC TTT ACA GAC TTA CAT GGG ATC AGT       2428
Gln Asp Pro Gln Gln Tyr Asn Val Phe Thr Asp Leu His Gly Ile Ser
            670             675             680

CAA GAG TTC CCC TAC AAA TCT GAA ATG GAT TCT ATG CCT TAT ACA CAG       2476
Gln Glu Phe Pro Tyr Lys Ser Glu Met Asp Ser Met Pro Tyr Thr Gln
        685             690             695

AAC TTT ATT TCC TGT AAT CAG CCT GTA TTA CCA CAA CAT TCC AAA TGT       2524
Asn Phe Ile Ser Cys Asn Gln Pro Val Leu Pro Gln His Ser Lys Cys
    700             705             710

ACA GAG CTG GAC TAC CCT ATG GGG AGT TTT GAA CCA TCC CCA TAC CCC       2572
Thr Glu Leu Asp Tyr Pro Met Gly Ser Phe Glu Pro Ser Pro Tyr Pro
715             720             725             730

ACT ACT TCT AGT TTA GAA GAT TTT GTC ACT TGT TTA CAA CTT CCT GAA       2620
Thr Thr Ser Ser Leu Glu Asp Phe Val Thr Cys Leu Gln Leu Pro Glu
                735             740             745

AAC CAA AAG CAT GGA TTA AAT CCA CAG TCA GCC ATA ATA ACT CCT CAG       2668
Asn Gln Lys His Gly Leu Asn Pro Gln Ser Ala Ile Ile Thr Pro Gln
            750             755             760

ACA TGT TAT GCT GGG GCC GTG TCG ATG TAT CAG TGC CAG CCA GAA CCT       2716
Thr Cys Tyr Ala Gly Ala Val Ser Met Tyr Gln Cys Gln Pro Glu Pro
        765             770             775

CAG CAC ACC CAC GTG GGT CAG ATG CAG TAC AAT CCA GTA CTG CCA GGC       2764
Gln His Thr His Val Gly Gln Met Gln Tyr Asn Pro Val Leu Pro Gly
    780             785             790

CAA CAG GCA TTT TTA AAC AAG TTT CAG AAT GGA GTT TTA AAT GAA ACA       2812
Gln Gln Ala Phe Leu Asn Lys Phe Gln Asn Gly Val Leu Asn Glu Thr
795             800             805             810

TAT CCA GCT GAA TTA AAT AAC ATA AAT AAC ACT CAG ACT ACC ACA CAT       2860
Tyr Pro Ala Glu Leu Asn Asn Ile Asn Asn Thr Gln Thr Thr Thr His
                815             820             825

CTT CAG CCA CTT CAT CAT CCG TCA GAA GCC AGA CCT TTT CCT GAT TTG       2908
Leu Gln Pro Leu His His Pro Ser Glu Ala Arg Pro Phe Pro Asp Leu
            830             835             840

ACA TCC AGT GGA TTC CTG T AATTCCAAGC CCAATTTTGA CCCTGGTTTT           2957
Thr Ser Ser Gly Phe Leu
        845
```

| | | | | | |
|---|---|---|---|---|---|
|TGGATTAAAT|TAGTTTGTGA|AGGATTATGG|AAAAATAAAA|CTGTCACTGT|TGGACGTCAG|3017|
|CAAGTTCACA|TGGAGGCATT|GATGCATGCT|ATTCACAATT|ATTCCAAACC|AAATTTTAAT|3077|
|TTTTGCTTTT|AGAAAAGGGA|GTTTAAAAAT|GGTATCAAAA|TTACATATAC|TACAGTCAAG|3137|
|ATAGAAAGGG|TGCTGCCACG|GAGTGGTGAG|GTACCGTCTA|CATTTCACAT|TATTCTGGGC|3197|
|ACCACAAAAT|ATACAAAACT|TTATCAGGGA|AACTAAGATT|CTTTTAAATT|AGAAATATT|3257|
|CTCTATTTGA|ATTATTTCTG|TCACAGTAAA|AATAAAATAC|TTTGAGTTTT|GAGCTACTGG|3317|
|ATTCTTATTA|GTTCCCCAAA|TACAAAGTTA|GAGAACTAAA|CTAGTTTTC|CTATCATGTT|3377|
|AACCTCTGCT|TTTATCTCAG|ATGTTAAAAT|AAATGGTTTG|GTGCTTTTA|TAAAAGATA|3437|
|ATCTCAGTGC|TTTCCTCCTT|CACTGTTTCA|TCTAAGTGCC|TCACATTTTT|TTCTACCTAT|3497|
|AACACTCTAG|GATGTATATT|TTATATAAAG|TATTCTTTTT|CTTTTTAAA|TTAATATCTT|3557|
|TCTGCACACA|AATATTATTT|GTGTTTCCTA|AATCCAACCA|ATTTTCATTA|ATTCAGGCAT|3617|
|ATTTTAACTC|CACTGCTTAC|CTACTTTCTT|CAGGTAAAAG|GGCAAATAAT|GATCGAAAAA|3677|
|ATAATTATTT|ATTACATAAT|TTAGTTGTTT|CTAGACTATA|AATGTTGCTA|TGTGCCTTAT|3737|
|GTTGAAAAAA|TTTAAAAGTA|AAATGTCTTT|CCAAATTATT|TCTTAATTAT|TATAAAAATA|3797|
|TTAAGACAAT|AGCACTTAAA|TTCCTCAACA|GTGTTTTCAG|AAGAAATAAA|TATACCACTC|3857|
|TTTACCTTTA|TTGATATCTC|CATGATGATA|GTTGAATGTT|GCAATGTGAA|AAATCTGCTG|3917|
|TTAACTGCAA|CCTTGTTTAT|TAAATTGCAA|GAAGCTTTAT|TTCTAGCTTT|TTAATTAAGC|3977|
|AAAGCACCCA|TTTCAATGTG|TATAAATTGT|CTTTAAAAAC|TGTTTAGAC|CTATAATCCT|4037|
|TGATAATATA|TTGTGTTGAC|TTTATAAATT|TCGCTTCTTA|GAACAGTGGA|AACTATGTGT|4097|
|TTTTCTCATA|TTTGAGGAGT|GTTAAGATTG|CAGATAGCAA|GGTTTGGTGC|AAAGTATTGT|4157|
|AATGAGTGAA|TTGAATGGTG|CATTGTATAG|ATATAATGAA|CAAAATTATT|TGTAAGATAT|4217|
|TTGCAGTTTT|TCATTTTAAA|AAGTCCATAC|CTTATATATG|CACTTAATTT|GTTGGGGCTT|4277|
|TACATACTTT|ATCAATGTGT|CTTTCTAAGA|AATCAAGTAA|TGAATCCAAC|TGCTTAAAGT|4337|
|TGGTATTAAT|AAAAGACAA|CCACATAGTT|CGTTTACCTT|CAAACTTTAG|GTTTTTTTAA|4397|
|TGATATACTG|ATCTTCATTA|CCAATAGGCA|AATTAATCAC|CCTACCAACT|TTACTGTCCT|4457|
|AACATGGACT|TTCAAAAAGA|AAAAATGACA|CCATCTTTTA|TTCTTTTTTT|TTTTTTTTT|4517|
|TTGAGAGAGA|GTCTTACTCT|GCCGCCCAAA|CTGGAGTGCA|GTGGCACAAT|CTTGGCTCAC|4577|
|TGCAACCTCT|ACCTCCTGGG|TTCAAGTGAT|TCTCTTGCCT|CAGCCTCCCG|AGTTGCTGGG|4637|
|ATTGCGGGCA|TGGTGGCGTG|AGCCTGTAGT|CCTAGCTACT|CGGGAGGCTG|AGGCAGGAGA|4697|
|ATAGCCTGAA|CCTGGGAATC|GGAGGTTGCA|GGGCCAAGAT|CGCCCCACTG|CACTCCAGCC|4757|
|TGGCAATAGA|CCGAGCTCCG|TCTCCAAAAA|AAAAAATACA|ATTTTTATTT|CTTTTACTTT|4817|
|TTTTAGTAAG|TTAATGTATA|TAAAAATGGC|TTCGGACAAA|ATATCTCTGA|GTTCTGTGTA|4877|
|TTTTCAGTCA|AAACTTTAAA|CCTGTAGAAT|CAATTTAAGT|GTTGAAAAAA|ATTTGTCTGA|4937|
|AACATTTCAT|AATTTGTTTC|CAGCATGAGG|TATCTAAGGA|TTTAGACCAG|AGGTCTAGAT|4997|
|TAATACTCTA|TTTTTACATT|TAAACCTTTT|ATTATAAGTC|TTACATAAAC|CATTTTTGTT|5057|
|ACTCTCTTCC|ACATGTTACT|GGATAAATTG|TTTAGTGGAA|AATAGGCTTT|TAATCATGA|5117|
|ATATGATGAC|AATCAGTTAT|ACAGTTATAA|AATTAAAAGT|TTGAAAAGCA|ATATTGTATA|5177|
|TTTTTATCTA|TATAAAATAA|CTAAAATGTA|TCTAAGAATA|ATAAAATCAC|GTTAAACCAA|5237|
|AAAAAAAAAA|AAAAAAAAAA|AAAA| | |5261|

( 2 ) INFORMATION FOR SEQ ID NO:4:

(i) SEQUENCE CHARACTERISTICS:
 (A) LENGTH: 848 amino acids
 (B) TYPE: amino acid
 (D) TOPOLOGY: linear (ii) MOLECULE TYPE: protein (xi) SEQUENCE DESCRIPTION: SEQ ID NO:4:

```
Met Asn Ser Ser Ser Ala Asn Ile Thr Tyr Ala Ser Arg Lys Arg Arg
 1               5                  10                  15

Lys Pro Val Gln Lys Thr Val Lys Pro Ile Pro Ala Glu Gly Ile Lys
             20                  25                  30

Ser Asn Pro Ser Lys Arg His Arg Asp Arg Leu Asn Thr Glu Leu Asp
             35                  40                  45

Arg Leu Ala Ser Leu Leu Pro Phe Pro Gln Asp Val Ile Asn Lys Leu
 50                  55                  60

Asp Lys Leu Ser Val Leu Arg Leu Ser Val Ser Tyr Leu Arg Ala Lys
 65                  70                  75                  80

Ser Phe Phe Asp Val Ala Leu Lys Ser Ser Pro Thr Glu Arg Asn Gly
                 85                  90                  95

Gly Gln Asp Asn Cys Arg Ala Ala Asn Phe Arg Glu Gly Leu Asn Leu
             100                 105                 110

Gln Glu Gly Glu Phe Leu Leu Gln Ala Leu Asn Gly Phe Val Leu Val
         115                 120                 125

Val Thr Thr Asp Ala Leu Val Phe Tyr Ala Ser Ser Thr Ile Gln Asp
130                 135                 140

Tyr Leu Gly Phe Gln Gln Ser Asp Val Ile His Gln Ser Val Tyr Glu
145                 150                 155                 160

Leu Ile His Thr Glu Asp Arg Ala Glu Phe Gln Arg Gln Leu His Trp
                 165                 170                 175

Ala Leu Asn Pro Ser Gln Cys Thr Glu Ser Gly Gln Gly Ile Glu Glu
             180                 185                 190

Ala Thr Gly Leu Pro Gln Thr Val Val Cys Tyr Asn Pro Asp Gln Ile
         195                 200                 205

Pro Pro Glu Asn Ser Pro Leu Met Glu Arg Cys Phe Ile Cys Arg Leu
210                 215                 220

Arg Cys Leu Leu Asp Asn Ser Ser Gly Phe Leu Ala Met Asn Phe Gln
225                 230                 235                 240

Gly Lys Leu Lys Tyr Leu His Gly Gln Lys Lys Gly Lys Asp Gly
                 245                 250                 255

Ser Ile Leu Pro Pro Gln Leu Ala Leu Phe Ala Ile Ala Thr Pro Leu
             260                 265                 270

Gln Pro Pro Ser Ile Leu Glu Ile Arg Thr Lys Asn Phe Ile Phe Arg
         275                 280                 285

Thr Lys His Lys Leu Asp Phe Thr Pro Ile Gly Cys Asp Ala Lys Gly
290                 295                 300

Arg Ile Val Leu Gly Tyr Thr Glu Ala Glu Leu Cys Thr Arg Gly Ser
305                 310                 315                 320

Gly Tyr Gln Phe Ile His Ala Ala Asp Met Leu Tyr Cys Ala Glu Ser
                 325                 330                 335

His Ile Arg Met Ile Lys Thr Gly Glu Ser Gly Met Ile Val Phe Arg
             340                 345                 350

Leu Leu Thr Lys Asn Asn Arg Trp Thr Trp Val Gln Ser Asn Ala Arg
         355                 360                 365

Leu Leu Tyr Lys Asn Gly Arg Pro Asp Tyr Ile Ile Val Thr Gln Arg
370                 375                 380

Pro Leu Thr Asp Glu Glu Gly Thr Glu His Leu Arg Lys Arg Asn Thr
```

-continued

| 385 | | | | | 390 | | | | | 395 | | | | | 400 |
|---|---|---|---|---|---|---|---|---|---|---|---|---|---|---|---|
| Lys | Leu | Pro | Phe | Met | Phe | Thr | Thr | Gly | Glu | Ala | Val | Leu | Tyr | Glu | Ala |
| | | | | 405 | | | | 410 | | | | 415 | | | |
| Thr | Asn | Pro | Phe | Pro | Ala | Ile | Met | Asp | Pro | Leu | Pro | Leu | Arg | Thr | Lys |
| | | | 420 | | | | 425 | | | | | 430 | | | |
| Asn | Gly | Thr | Ser | Gly | Lys | Asp | Ser | Ala | Thr | Thr | Ser | Thr | Leu | Ser | Lys |
| | | 435 | | | | 440 | | | | | 445 | | | | |
| Asp | Ser | Leu | Asn | Pro | Ser | Ser | Leu | Leu | Ala | Ala | Met | Met | Gln | Gln | Asp |
| 450 | | | | | 455 | | | | | 460 | | | | | |
| Glu | Ser | Ile | Tyr | Leu | Tyr | Pro | Ala | Ser | Ser | Thr | Ser | Ser | Thr | Ala | Pro |
| 465 | | | | 470 | | | | 475 | | | | | 480 | | |
| Phe | Glu | Asn | Asn | Phe | Phe | Asn | Glu | Ser | Met | Asn | Glu | Cys | Arg | Asn | Trp |
| | | | 485 | | | | 490 | | | | | 495 | | | |
| Gln | Asp | Asn | Thr | Ala | Pro | Met | Gly | Asn | Asp | Thr | Ile | Leu | Lys | His | Glu |
| | | | 500 | | | | 505 | | | | | 510 | | | |
| Gln | Ile | Asp | Gln | Pro | Gln | Asp | Val | Asn | Ser | Phe | Ala | Gly | Gly | His | Pro |
| | | 515 | | | | 520 | | | | | 525 | | | | |
| Gly | Leu | Phe | Gln | Asp | Ser | Lys | Asn | Ser | Asp | Leu | Tyr | Ser | Ile | Met | Lys |
| | 530 | | | | 535 | | | | | 540 | | | | | |
| Asn | Leu | Gly | Ile | Asp | Phe | Glu | Asp | Ile | Arg | His | Met | Gln | Asn | Glu | Lys |
| 545 | | | | 550 | | | | 555 | | | | | 560 | | |
| Phe | Phe | Arg | Asn | Asp | Phe | Ser | Gly | Glu | Val | Asp | Phe | Arg | Asp | Ile | Asp |
| | | | 565 | | | | 570 | | | | | 575 | | | |
| Leu | Thr | Asp | Glu | Ile | Leu | Thr | Tyr | Val | Gln | Asp | Ser | Leu | Ser | Lys | Ser |
| | | | 580 | | | | 585 | | | | | 590 | | | |
| Pro | Phe | Ile | Pro | Ser | Asp | Tyr | Gln | Gln | Gln | Ser | Leu | Ala | Leu | Asn |
| | | 595 | | | | 600 | | | | | 605 | | | | |
| Ser | Ser | Cys | Met | Val | Gln | Glu | His | Leu | His | Leu | Glu | Gln | Gln | Gln | Gln |
| | 610 | | | | 615 | | | | | 620 | | | | | |
| His | His | Gln | Lys | Gln | Val | Val | Glu | Pro | Gln | Gln | Gln | Leu | Cys | Gln |
| 625 | | | | 630 | | | | 635 | | | | | 640 | | |
| Lys | Met | Lys | His | Met | Gln | Val | Asn | Gly | Met | Phe | Glu | Asn | Trp | Asn | Ser |
| | | | 645 | | | | 650 | | | | | 655 | | | |
| Asn | Gln | Ile | Val | Pro | Phe | Asn | Cys | Pro | Gln | Gln | Asp | Pro | Gln | Gln | Tyr |
| | | | 660 | | | | 665 | | | | | 670 | | | |
| Asn | Val | Phe | Thr | Asp | Leu | His | Gly | Ile | Ser | Gln | Glu | Phe | Pro | Tyr | Lys |
| | | 675 | | | | 680 | | | | | 685 | | | | |
| Ser | Glu | Met | Asp | Ser | Met | Pro | Tyr | Thr | Gln | Asn | Phe | Ile | Ser | Cys | Asn |
| | 690 | | | | 695 | | | | | 700 | | | | | |
| Gln | Pro | Val | Leu | Pro | Gln | His | Ser | Lys | Cys | Thr | Glu | Leu | Asp | Tyr | Pro |
| 705 | | | | 710 | | | | 715 | | | | | 720 | | |
| Met | Gly | Ser | Phe | Glu | Pro | Ser | Pro | Tyr | Pro | Thr | Thr | Ser | Ser | Leu | Glu |
| | | | 725 | | | | 730 | | | | | 735 | | | |
| Asp | Phe | Val | Thr | Cys | Leu | Gln | Leu | Pro | Glu | Asn | Gln | Lys | His | Gly | Leu |
| | | | 740 | | | | 745 | | | | | 750 | | | |
| Asn | Pro | Gln | Ser | Ala | Ile | Ile | Thr | Pro | Gln | Thr | Cys | Tyr | Ala | Gly | Ala |
| | | 755 | | | | 760 | | | | | 765 | | | | |
| Val | Ser | Met | Tyr | Gln | Cys | Gln | Pro | Glu | Pro | Gln | His | Thr | His | Val | Gly |
| | 770 | | | | 775 | | | | | 780 | | | | | |
| Gln | Met | Gln | Tyr | Asn | Pro | Val | Leu | Pro | Gly | Gln | Gln | Ala | Phe | Leu | Asn |
| 785 | | | | 790 | | | | 795 | | | | | 800 | | |
| Lys | Phe | Gln | Asn | Gly | Val | Leu | Asn | Glu | Thr | Tyr | Pro | Ala | Glu | Leu | Asn |
| | | | 805 | | | | 810 | | | | | 815 | | | |
| Asn | Ile | Asn | Asn | Thr | Gln | Thr | Thr | Thr | His | Leu | Gln | Pro | Leu | His | His |
| | | | 820 | | | | 825 | | | | | 830 | | | |

Pro Ser Glu Ala Arg Pro Phe Pro Asp Leu Thr Ser Ser Gly Phe Leu
    835                 840                 845

( 2 ) INFORMATION FOR SEQ ID NO:5:

( i ) SEQUENCE CHARACTERISTICS:
        ( A ) LENGTH: 52 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: modifiedbase
        ( B ) LOCATION: 3
        ( D ) OTHER INFORMATION: /modbase=i ( i x ) FEATURE:
        ( A ) NAME/KEY: modifiedbase
        ( B ) LOCATION: 6
        ( D ) OTHER INFORMATION: /modbase=i ( i x ) FEATURE:
        ( A ) NAME/KEY: modifiedbase
        ( B ) LOCATION: 13
        ( D ) OTHER INFORMATION: /modbase=i ( i x ) FEATURE:
        ( A ) NAME/KEY: modifiedbase
        ( B ) LOCATION: 16
        ( D ) OTHER INFORMATION: /modbase=i ( i x ) FEATURE:
        ( A ) NAME/KEY: modifiedbase
        ( B ) LOCATION: 19
        ( D ) OTHER INFORMATION: /modbase=i ( i x ) FEATURE:
        ( A ) NAME/KEY: modifiedbase
        ( B ) LOCATION: 22
        ( D ) OTHER INFORMATION: /modbase=i ( i x ) FEATURE:
        ( A ) NAME/KEY: modifiedbase
        ( B ) LOCATION: 29
        ( D ) OTHER INFORMATION: /modbase=i ( i x ) FEATURE:
        ( A ) NAME/KEY: modifiedbase
        ( B ) LOCATION: 32
        ( D ) OTHER INFORMATION: /modbase=i ( i x ) FEATURE:
        ( A ) NAME/KEY: modifiedbase
        ( B ) LOCATION: 43
        ( D ) OTHER INFORMATION: /modbase=i ( i x ) FEATURE:
        ( A ) NAME/KEY: modifiedbase
        ( B ) LOCATION: 46
        ( D ) OTHER INFORMATION: /modbase=i ( x i ) SEQUENCE DESCRIPTION: SEQ ID NO:5:

TTNATNCCTC TCNGCNGGNA TNGGTCTTNA CNGTTCTTTC TGNACNGGTC TT                52

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: modifiedbase ( B ) LOCATION: 7
                    ( D ) OTHER INFORMATION: /modbase=OTHER
                         / note="Can be either adenine, thymine, guanosine,
                         or cytosine."

( i x ) FEATURE:
                    ( A ) NAME/KEY: modifiedbase
                    ( B ) LOCATION: 10
                    ( D ) OTHER INFORMATION: /modbase=OTHER
                         / note="Can be either adenine, thymine, guanosine,
                         or cytosine."

( x i ) SEQUENCE DESCRIPTION: SEQ ID NO:6:

AAAGCCNGTN CAAGAAAGAC                                                                                        20

( 2 ) INFORMATION FOR SEQ ID NO:7:

( i ) SEQUENCE CHARACTERISTICS:
                    ( A ) LENGTH: 25 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:7:

GGATTTGACT TAATTCCTTC AGGGG                                                                                  25

( 2 ) INFORMATION FOR SEQ ID NO:8:

( i ) SEQUENCE CHARACTERISTICS:
                    ( A ) LENGTH: 40 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:8:

CCATCGATCT CGAGAGATTG CAGATAGCAA GGTTTGGTGC                                                                  40

( 2 ) INFORMATION FOR SEQ ID NO:9:

( i ) SEQUENCE CHARACTERISTICS:
                    ( A ) LENGTH: 38 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:9:

CCATCGATCT CGAGTGTAAT GAGTGAATTG AATGGTGC                                                                    38

( 2 ) INFORMATION FOR SEQ ID NO:10:

( i ) SEQUENCE CHARACTERISTICS:
                    ( A ) LENGTH: 30 base pairs
                    ( B ) TYPE: nucleic acid
                    ( C ) STRANDEDNESS: unknown
                    ( D ) TOPOLOGY: unknown ( i i ) MOLECULE TYPE: DNA (genomic)

( x i ) SEQUENCE DESCRIPTION: SEQ ID NO:10:

GAAGATCTTC CAGTGGTCCC AGCCTACACC                                                                             30

( 2 ) INFORMATION FOR SEQ ID NO:11:

( i ) SEQUENCE CHARACTERISTICS:
                    ( A ) LENGTH: 30 base pairs
                    ( B ) TYPE: nucleic acid ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:11:

GAAGATCTTC ATGTGAACTT GCTGACGTCC                                   30

( 2 ) INFORMATION FOR SEQ ID NO:12:

( i ) SEQUENCE CHARACTERISTICS:
        ( A ) LENGTH: 63 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:12:

GCTCTAGATG ATCACCATGG TGCAGAAGAC CGTGAAGCCC ATCCCCGCTG AAGGAATTAA    60

GTC                                                                 63

( 2 ) INFORMATION FOR SEQ ID NO:13:

( i ) SEQUENCE CHARACTERISTICS:
        ( A ) LENGTH: 63 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:13:

GCACTAGTTG ATCACCATGG CCAGCCGCAA GCGGCGCAAG CCGGTGCAGA AGACCGTGAA    60

GCC                                                                 63

( 2 ) INFORMATION FOR SEQ ID NO:14:

( i ) SEQUENCE CHARACTERISTICS:
        ( A ) LENGTH: 65 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:14:

GCACTAGTTG ATCACCATGA GCAGCGGCGC CAACATCACC TATGCCAGCC GCAAGCGCCG    60

CAAGC                                                               65

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:15:

GCAGAGTCTG GGTTTAGAGC                                               20

( 2 ) INFORMATION FOR SEQ ID NO:16:

( i ) SEQUENCE CHARACTERISTICS:
        ( A ) LENGTH: 27 base pairs
        ( B ) TYPE: nucleic acid
        ( C ) STRANDEDNESS: unknown ( D ) TOPOLOGY: unknown ( i i ) MOLECULE TYPE: DNA (genomic)

( x i ) SEQUENCE DESCRIPTION: SEQ ID NO:16:

TCGAGTAGAT CACGCAATGG GCCCAGC                27

( 2 ) INFORMATION FOR SEQ ID NO:17:

( i ) SEQUENCE CHARACTERISTICS:
        ( A ) LENGTH: 27 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:17:

TCGAGCTGGG CCCATTGCGT GATCTAC                27

( 2 ) INFORMATION FOR SEQ ID NO:18:

( i ) SEQUENCE CHARACTERISTICS:
        ( A ) LENGTH: 28 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:18:

GCGTCGACTG GGCACCATGA ACAGCAGC                28

( 2 ) INFORMATION FOR SEQ ID NO:19:

( i ) SEQUENCE CHARACTERISTICS:
        ( A ) LENGTH: 40 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:19:

CCCAAGCTTA CGCGTGGTTC TCTGGAGGAA GCTGGTCTGG                40

( 2 ) INFORMATION FOR SEQ ID NO:20:

( i ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:20:

CCCAAGCTTA CGCGTGGAAG TCTAGCTTGT GTTTGG                36

( 2 ) INFORMATION FOR SEQ ID NO:21:

( i ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:21:

CCCAAGCTTA CGCGTGAAGC CGGAAAACTG TCATGC                36

(2) INFORMATION FOR SEQ ID NO:22:

(i) SEQUENCE CHARACTERISTICS:
(A) LENGTH: 49 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:22:

CCCAAGCTTA CGCGTGCAGT GGTCTCTGAG TGGCGATGAT GTAATCTGG 49

(2) INFORMATION FOR SEQ ID NO:23:

(i) SEQUENCE CHARACTERISTICS:
(A) LENGTH: 37 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:23:

CCCAAGCTTA CGCGTGGTCT TTGAAGTCAA CCTCACC 37

NUCLEIC ACIDS ENCODING MURINE AND HUMAN AH RECEPTORS

This invention was made with Government support under Grant Number: ES-05703 and ES-01884 awarded by the National Institute of Environmental Health Sciences. The Government has certain rights in the invention.

FIELD OF THE INVENTION

This invention relates to a cDNA molecule encoding an murine and human Ah-receptor ($Ah^{b-1}$ allele) that has been isolated and characterized. More specifically, the cDNA can be used to make an Ah-receptor which can be used in bioassays for detecting environmental pollutants. Additionally, the cDNA can be used in the generation of recombinant organisms that serve as biomonitors for environmental pollutants or can regulate gene expression for receptor agonists. Additionally, the cDNAs can be used to detect human and wildlife populations that have high susceptibility to environmental pollutants and polycyclic aromatic hydrocarbons.

DESCRIPTION OF THE PRIOR ART

Ah-receptor is a soluble protein which mediates an individuals response to a variety of drugs, carcinogens and toxic agents. Chemicals which interact with the Ah-receptor, include a variety of environmental contaminants (dioxins, PCBs, PBBs, benzo(a)pyrene and a variety of natural products (flavones, carbazoles etc). One of the most potent agonists of the Ah-receptor is 2,3,7,8-tetrachlorodibenzo-p-dioxin (TCDD or "dioxin"). TCDD is the prototype for a large family of highly toxic carcinogenic and teratogenic environmental contaminants. Poland A., Knutson, J. C., *Ann. Rev. Pharmacol. Toxicol.* 22:517–554 (1982). TCDD can induce a variety of receptor-medicated toxic responses, including a severe wasting syndrome, epidermal hyperplasia and metaplasis, tumor promotion and thymic involution. Upon binding to a agonist, the Ah-receptor interacts with dioxin responsive elements (DREs) that lie upstream of target promotors and activates the expression of a number of genes. Nebert, D. W., Gonzalez, F. J., *Ann. Rev. Biochem.*, 56:945–993 (1987); Durin, L. K., Jones, P. B. C., Fisher, J. M., Galeazzi, D. R. and Whitlock, J. P., *J. Cell. Biochem.*, 35:153–60 (1987); Telakowski-Hopkins, C. A., King, R. G., Pickett, C. B., *Proc. Natl. Acad. Sci. (USA)* 85:1000–1004 (1988). At least two other proteins play a role in receptor signaling. The 90 kD heat shock protein (Hsp 90) holds the receptor in a conformation that is able to bind ligand and also represses the receptor's intrinsic DNA binding properties. Perdew, G. H., *J. Biol. Chem*, 263:13802–13805 (1988); Pongratz, I., Mason, G. G. F., Poellinger, L., *J. Biol. Chem.* 267:13728–13724 (1992). The Ah-receptor nuclear translocator or ARNT, is required for proper nuclear targeting of the Ah-receptor and has been shown to be a part of the ligand-induced protein complex that binds to DNA sequences in response to activation by TCDD. Hoffman, E. C., et al., *Science* 252:954–8 (1991); Reyes, H., Reisz-Porszasz, S., Hankinson, O., *Science* 256:1193–119 (1992); Elferink, C. J., Gasiewicz, T. A., Whitlock, J. P., *J. Biol. Chem.* 265:20708–12 (1990).

The photoaffinity ligand, [$^{125}$I]-2-azido-3-iodo-7,8-dibromodibenzo-p-dioxin, covalently labels the Ah-receptor from a number of species, tissues and cell types. Poland, A., Glover, E., Ebetino, F. H. & Kende, A. S., *J. Biol. Chem.* 261:6352–6365 (1986). These photoaffinity labeling studies demonstrated that the Ah-receptor exhibits significant polymorphism, both between species and within different strains of the same species. For example, four different allelic forms of the Ah-receptor have been identified in inbred strains of mice: $Ah^{b-1}$ allele (C57 strains)=95 kD, $Ah^{b-2}$ allele (e g., C3H strain)=104 kD, $Ah^{b-3}$ allele (Mus spretus)=105 kD, and $Ah^d$ allele (e.g., DBA strain)=104 kD. The $Ah^d$ allele encodes a receptor with a 10–100-fold lower affinity for agonist than the $Ah^{b-1}$ or $Ah^{b-2}$ alleles. Poland, A. & Glover, E., *Mol. Pharm.* 11:389–398 (1975); Okey, A. B., Vella, L. M. & Harper, P. A., *Mol. Pharm.* 35:823–830 (1989).

The purification of the Ah-receptor from C57BL/6J mouse liver has been described. Bradfield, C. A., Glover, E. & Poland, A., *Mol. Pharm.* 39:13-9 (1991). To confirm the identity of this purified protein, its N-terminal amino acids has been sequenced and antibodies were raised against the corresponding synthetic peptide. Poland, A., Glover, E. & Bradfield, C. A., *Mol. Pharmacol.* 39:20-6 (1991).

SUMMARY OF THE INVENTION

The present invention provides recombinant DNA molecules which encode murine and human Ah receptors. These Ah receptors have the DNA sequences set out in sequence ID. numbers 1 and 3 respectively. These recombinant DNA molecules can be used as follows: 1) to generate large quantities of Ah-receptor protein for use in competitive binding assays used for detecting environmental pollutants or can regulate gene expression in response to receptor agonists, 2) in the generation of recombinant organisms that can serve as biomonitors for environmental pollutants, and 3) in detecting human and wildlife populations that have high susceptibility to environmental pollutants and polycyclic aromatic hydrocarbons (found in cigarette smoke). In a method of obtaining murine Ah receptor cDNA, a recombinant library was probed with oligonucleotides from group consisting of the following three single strand oligonucleotides: TTNATNCCTCTCNGCNGGNATNGGTCTT-NACNGTCTTTCTGNACNGGTCTT (SEQUENCE ID. NO. 5), AAAGCCNGT-NCAAGAAAGAC (SEQUENCE I.D. NO. 6), GGATTTGACTTAATTCCTTCAGGGG (SEQUENCE I.D. NO. 7). Also in a method of obtaining human Ah receptor cDNA, a human Ah receptor was screened with the mouse cDNA described in Sequence ID. No. 1.

According to particular embodiments of the invention DNA encoding the Ah-receptor protein or a peptide fragment thereof may be used to diagnose abnormal susceptibility to dioxins and polycyclic aromatic hydrocarbons, or alternatively, it may be inserted into an expression vector, including, but not limited to, vaccinia virus, as well as bacteria, yeast, insect or other vertebrate vectors. The expression vectors may be used to produce Ah receptor protein or peptide in quantity; the resulting pure protein can be used in a competitive binding assay to detect environmental pollutants. Additionally, the recombinant protein can be used in cell culture to regulate the expression of heterologous promoters and their genes in an agohist dependent manner. Finally, the pure protein can be used to generate polyclonal or monoclonal antibodies.

DETAILED DESCRIPTION OF THE INVENTION

Figure 1:
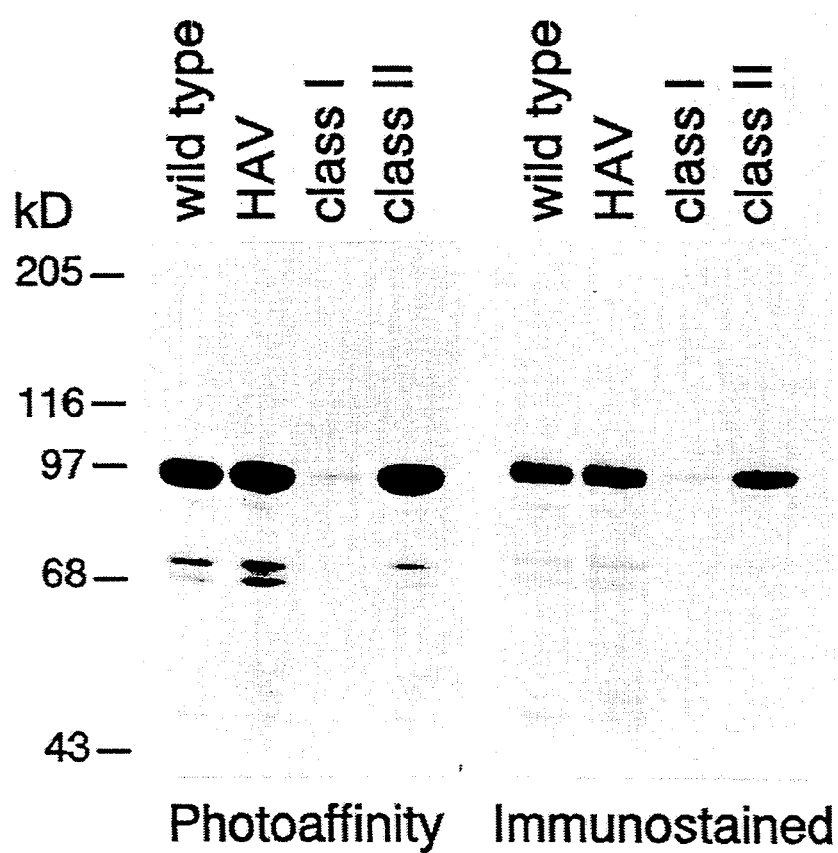
FIG. 1 shows detection of the Ah receptor in Wild-Type and Mutant Hepa-1c1c7 cells.

The present invention relates to Ah receptor cDNAs and proteins. For purposes of clarity of disclosure, and not by way of limitation, the detailed disclosure is divided into the following subsections:
(i) Cloning the Murine Ah-receptor;
 (a) Cloning the Murine Ah-Receptor
 (b) Cloning the Human Ah-Receptor
(ii) The genes and proteins of this invention;
(iii) Expression of the Ah receptor;
(iv) The utility of the invention.

(i) Cloning the Ah-receptor

(a) Cloning the Murine Ah-Receptor

The Ah receptor gene defined herein as nucleic acid sequences encoding Ah receptor proteins, may be identified according to the invention by cloning cDNA transcripts of the Ah receptor and identifying clones containing full length Ah receptor protein-encoding sequences or using oligonucleotide probes designated as sequence Id. numbers 5, 6 & 7.

Three oligonucleotide probes were used to obtain a cDNA encoding full length Ah receptor. These oligonucleotides were determined from the N-terminal amino acid sequence of a purified Ah receptor. The three oligonucleotides probes were referred to as OL-18, OL-2, and OL-27. OL-18 was designed from the amino acid sequence lysine 16-lysine 31 and was represented by the DNA sequence:

5'TTNATNCCT/CTCNGCNG-GNATNGGT/CTTNACNGTT/CTTT/CT-GNACNGGTCTT 3' (SEQUENCE ID. NO. 5) wherein A=Adenine, T=Thymine, C=Cytosine, G=Guanine, N=Inosine. OL-2 was designed from the amino acid sequence lysine-16-threonine and is represented by the DNA sequence:

5' AAA/GCCNGTNCAA/GAAAGAC 3' (SEQUENCE ID. NO. 6) wherein A=Adenine, T=Thymine, C=Cytosine, G=Guanine, N=A, C, G, and T. OL-27 was derived from the open reading frame of a genomic clone. OL-27 corresponds to the nucleotides encoding proline 26-34 and is represented by the DNA sequence:

5' GGATTTGACTTAATTCCTTCAGGGG 3' (SEQUENCE ! D. NO. 7) wherein A=Adenine, T=Thymine, C=Cytosine, G=Guanine.

The Ah-receptor was purified from C57BL/6J mouse liver that was covalently labeled with [$^{125}$I]-2-azido-3-iodo-7,8-dibromodibenzo-p-dioxin. See pages 45-52 of the specification. While mouse liver is probably the best source for Ah-receptor, other rodent tissues, such as murine thymus, kidney, lung, etc., can be utilized. To obtain the cDNA molecule, the OL-18 oligonucleotide, designed from the N-terminal amino acid sequence, is used as a probe to screen a mouse genomic DNA library. After screening $4 \times 10^5$ recombinant plaques, the OL-18 oligonucleotide is used as a hybridization probe to isolate a clone. This clone is further analyzed using the second oligonucleotide, OL-2.

The third oligonucleotide, OL-27, is designed from the downstream open reading frame (ORF) of the above genomic clone. OL-27 is used to screen $6 \times 10^5$ recombinants under high stringency conditions (65° C. $2 \times SSC$) to isolate a single clone, cAH1. See FIG. 2. The cAh1 clone is used as a probe to rescreen the mouse cDNA library. After rescreening an additional $1 \times 10^6$ recombinants, two overlapping clones, cAh3A and cAn4a are obtained. The cAh3A overlaps with the 3' end of cAh1. The cAh4A overlaps with the 3' end of cAh1 and the 5' end of cAh3A. See FIG. 2.

The genomic sequence 5' to the upstream open reading frame is analyzed and a putative upstream initiating methionine within a consensus sequence for translational initiation identified. Kozak, M., Nuc. Acids Res. 15:8125–8132 (1987). Polymerase chain reaction (PCR) is used to amplify this sequence out of Poly(A)RNA. The amplified fragment is subcloned into DBSK (clone cAhPCR1, FIG. 2) and sequenced to confirm its presence in the full length cDNA (mRNA).

(b) Cloning the Human Ah-receptor

The Ah-receptor's structure and the pattern of toxic responses that it induces vary significantly both within and across species. Poland, A., Knustson, J. C., Ann. Rev. Pharmacol. Toxicol. 22:517–554 (1982); Poland, A., Glover, E., Biochem. Biophys. Res. Comm. 146:1439–1449 (1987); Safe, S., Critical Reviews in Toxicology 21:51–88 (1990). This variability among animal models and target populations makes it difficult to confidently assess the risks associated with exposure to TCDD. "Research News", Science 252:911 (1991); "News and Comment", Science 251:624–626 (1991); Hanson, D. J., Chemical and Engineering News, 7–14 (1991). In order to perform functional comparisons of the Ah-receptor from two important animal targets, the murine cDNA was used as a probe to isolate the corresponding human clone. See Sequence ID. No. 1.

Figure 2:
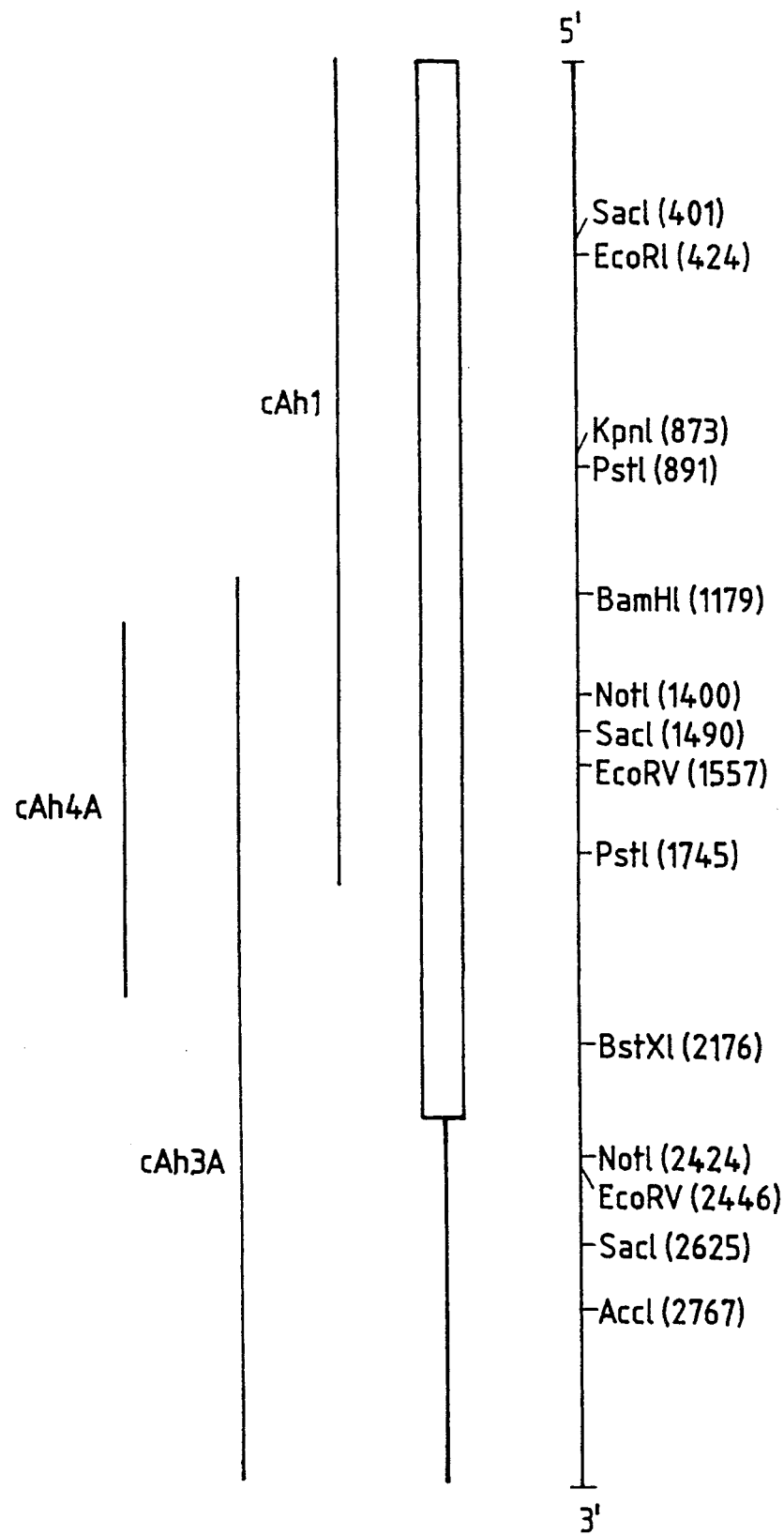
FIG. 2 shows a restriction map and location of mouse cDNA clones.
Figure 6A:
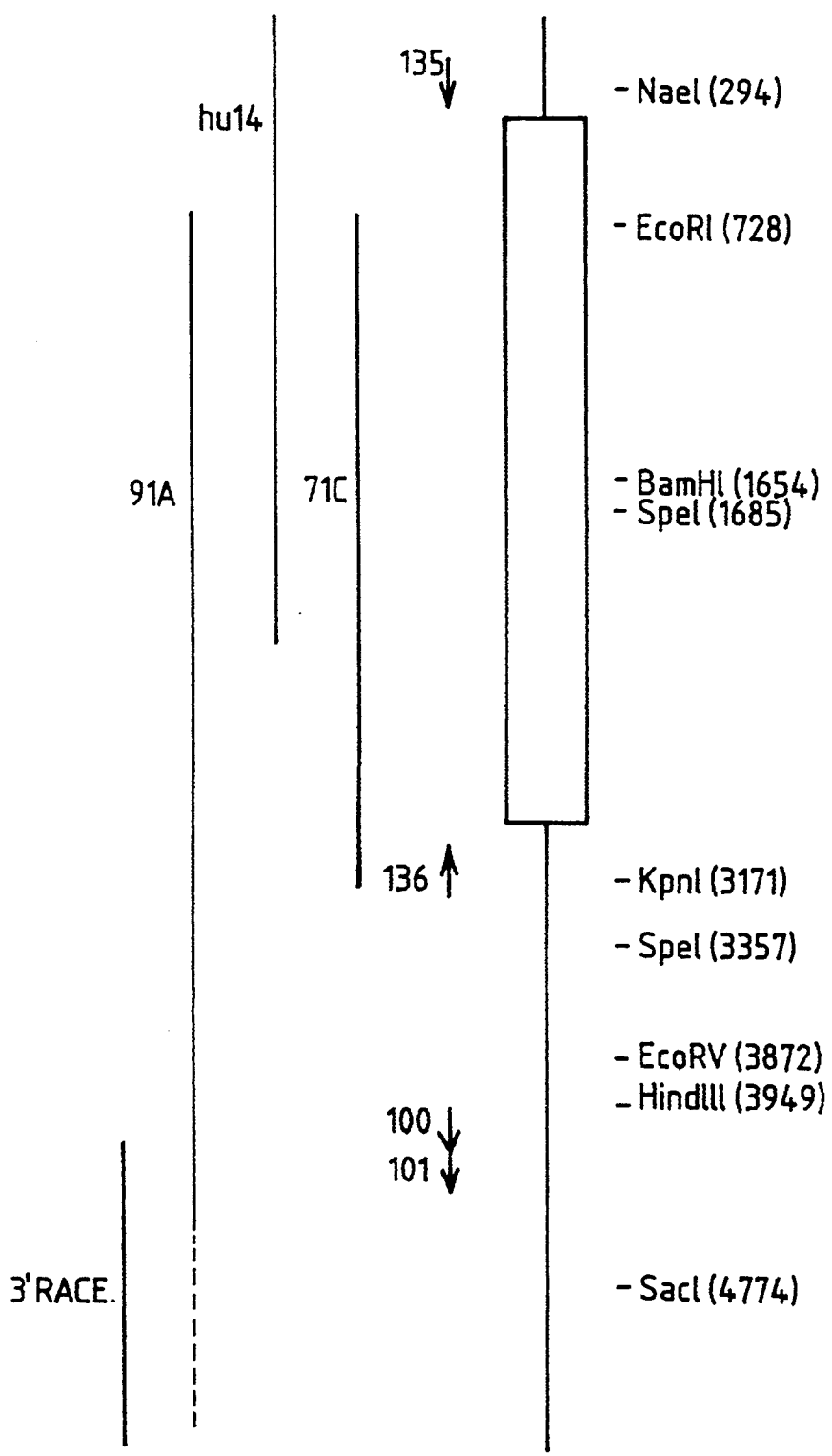
FIG. 6A shows a partial restriction map and location of human Ah-receptor cDNA clones.

The 1.4 bp EcoRI fragment from the murine Ah-receptor cDNA clone, cAh1, FIG. 2, was used as a probe to screen a commercially made human cDNA library constructed from oligo dT primed mRNA of the hepatoma cell line, HepG2 (Lambda Zap Vector, STRATAGENE). $5 \times 10^5$ Recombinants were screened (50% formamide 37° C.) yielding two overlapping cDNA clones, 91A and 71C. See FIG. 6A. Clone 91A contained a 4.47 kb insert which began with a continuous open reading frame (ORF) coding for 732 amino acids before reaching an in-frame termination codon (TAA). Clone 71C contained a 2.45 kb insert which began at the same site as 91A and extended 264 nucleotides beyond the termination codon. The ORF of the human Ah-receptor clones began at amino acid 15 of the murine Ah-receptor. An additional $4 \times 10^5$ recombinants were screened (50% formamide, 42° C.) using the 0.92 kb BamHi fragment of 91A as a probe. See FIG. 6A. One positive clone, hu14, was isolated which contained a 2.28 kb insert. The 3' end of this clone overlapped 1.56 kb with the 5' ends of 91A and 7iC. The 3' end of this clone overlapped 1.56 kb with the 5' ends of 91A and 71C. Sequence analysis of hu14 extended the ORF described for 91A and 71C an additional 116 amino acids at the N-terminus to a proposed initiation methionine. This methionine aligns with the initiation methionine previously described for the murine Ah-receptor (Kozak, M. *Nuc. Acids Res.* 15:8125–8132 (1987)), and has a stop codon 171 nucleotides immediately upstream. Clone 91A contains 2.27 kb of the 3' untranslated region (3' UTR) of the human Ah-receptor cDNA. To complete the 3' UTR, the rapid amplification of cDNA ends (RACE) method was used on HepG2 mRNA (Frohman, M. A., in *PCR Protocols: A Guide to Methods and Applications*, M. A. Innis, D. H. Gelfand, J. J. Shinsky, T. J. White, Eds. (Academic Press, Inc., San Diego, 1990), pp. 28–38.). Using two primers, 0L-100 and OL-101, specific to the 3' end of 91A, a single species of 1.1 kb was amplified. These two primers read as follows:

OL-100: 5' CCATCGATCTCGAGAGATT-GCAGATAGCAAGGTTTGGTGC 3' (SEQUENCE ID. NO. 8).

OL-101: 5' CCATCGATCTCGAGTGTAAT-GAGTGAATTCAJTGGTGC 3' (SEQUENCE ID. NO. 9). wherein A is adenine, T is thymine, G is guanine and C is cytosine.

The 5' end of this clone aligned with 91A for 0.48 kb to nucleotide 4640 where the two sequences diverged. See Sequence ID,. No. 3.

(ii) The Genes and Proteins of the Invention

The following nucleic acid sequences were determined. See sequence Id. number 1 for the murine Ah receptor. Additionally, the nucleic acid sequence for the human Ah receptor is shown in sequence I.D. number 3. These nucleic acid sequences can be altered and substitutions, additions or deletions that provide functionally equivalent molecules can be made.

In addition, the recombinant Ah receptor protein encoding nucleic acid sequence of the invention may be engineered so as to modify processing or expression of the Ah receptor protein.

The four murine clones of the Ah-receptor encode 805 amino acids (See Sequence I.D. No. 1 & 2). Based upon knowledge of the N-terminal amino acid sequence of this protein, it was concluded that the Ah-receptor, as found in vivo (i.e. after cleavage of a leader peptide and the initiation methionine) is a 796 amine acid protein with a calculated molecular weight of 89,426 daltons and an isoelectric point of 5.98. This calculated molecular weight is within 6% of the 95 kD predicted by analysis of the Ah-receptor by SDS-PAGE (Poland, A., Glover, E., & Bradfield, C. A., *Mol. Pharmacol.*, 39:20–6 (1991)) and the predicted pI is similar to that recently reported by two-dimensional gel electrophoresis of the protein 5.2–5.7. The more acidic nature of the protein as found in vivo may be attributable to receptor phosphorylation, a phenomenon which has experimental support. Perdew, G. H., & Hollenback, C. E., *Biochemistry*, 29:6210–4 (1990); Pongratz, I., Stromstedt, P. E., Mason, G. G. F., & Poellinger, L., *J. Biol. Chem.*, 266:16813–16817 (1991).

Figure 3:
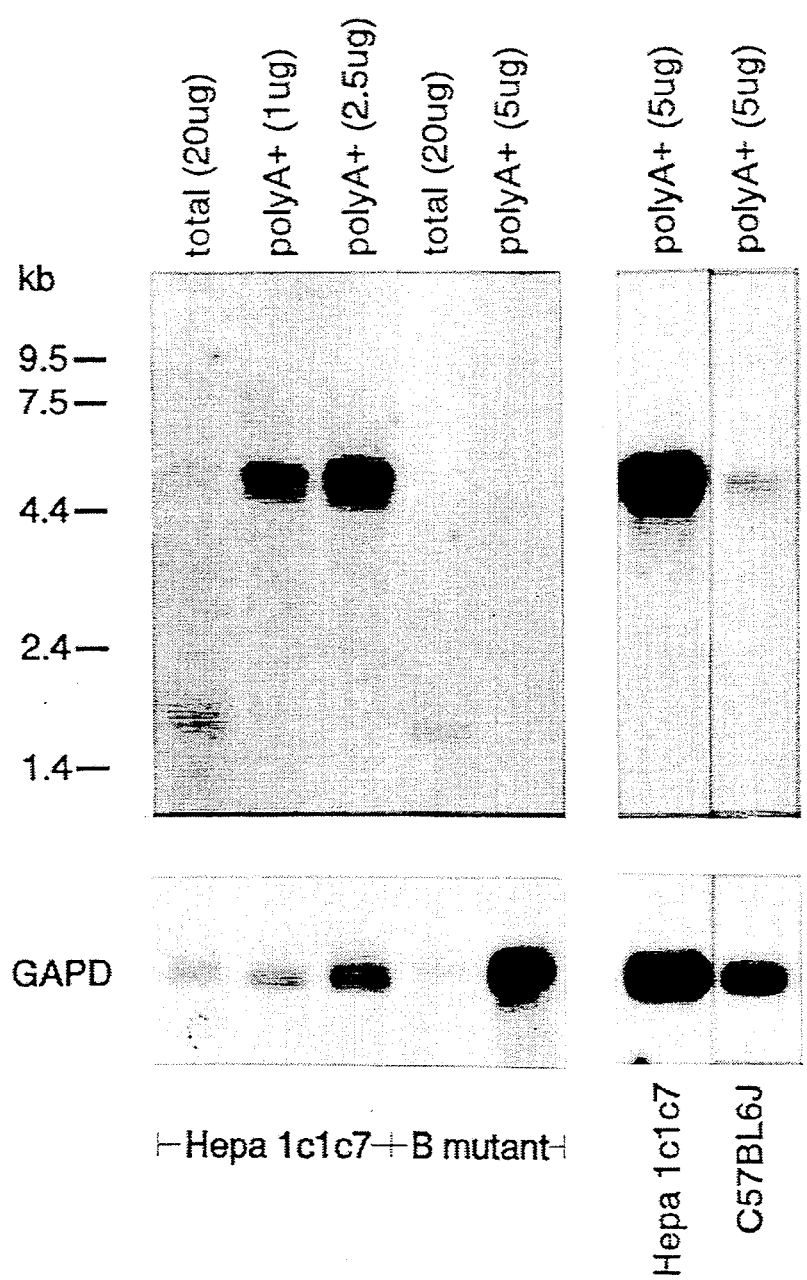
FIG. 3 shows Northern blot analysis of wild type and class I mutant Hepa 1c1c7 cells.

To estimate the size of the Ah-receptor mRNA, Northern analysis was performed on both total and poly(A) RNA isolated from Hepa 1c1c7 cells and the class I mutants. Using either the 0.42 kb (See FIG. 3) or the 1.4 kb EcoRI fragments of cAh1 as the hybridization proe, an mRNA species of approximately 5.4 kb was detected i the Hepa 1c1c7 cells. A minor band of approximately 5.2 kb is present in all cells and tissue samples and may represent an alternatively spliced transcript. The class I mutants, which express a very low level of the Ah-receptor protein (See FIG. 1), have undetectable expression of this 5.4 kb (or 5.2 kb) message under these same analysis conditions (See FIG. 3). Thus, the pattern of mRNA expression detected using the isolated cDNA as a probe is in agreement with what is seen at the protein level for the Ah-receptor.

Figure 5:
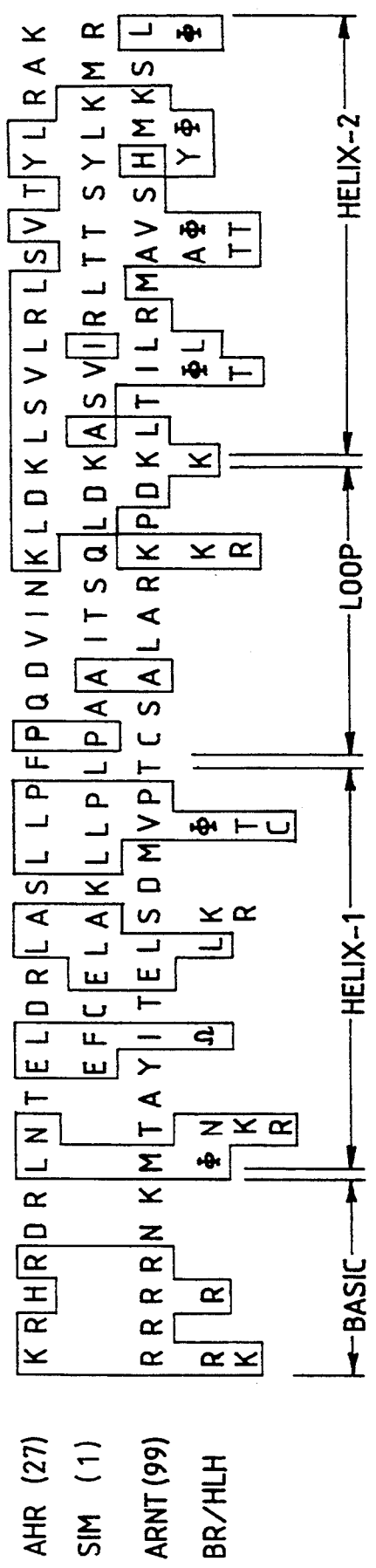
FIG. 5 shows the alignment of the basic helix-loop-helix domains of Ah-receptor (AHR), Sim, and ARNT.

Analysis of the primary amino acid sequence aloha with sequence comparison of the murine Ah-receptor was compared with proteins such as the Drospholia single-minded protein, Sim, and circadian rhythm protein, Per, and the human Ah-receptor nuclear translocator (ARNT) protein. This comparison provided insights into potential functional domains of the Ah protein. All of these proteins contain a homologous region of approximately 200 amino acids termed the PAAS domain (Per, ARNT, Ah-receptor, Sim). Nambu, J. R., Lewis, J. O., Warton, Jr., K. A., Crews. S. T., *Cell* 67:1157–1167 (1991). Adjacent to this domain in Sim, ARNT and the Ah-receptor is a basic region/helix-loop-helix motif (BR/HLH) similar to that found in many heterodimeric transcription factors. Weintraub, H., et al., *Science* 251:761–766 (1991); Blackwood, E. M., Eisenman, R. N., *Science* 251:1211–1217 (1991). See FIG. 5. The Ah-receptor and ARNT contain domains involved in the formation of heterodimeric DNA binding complexes and both proteins appear to be part of the TCDD induced complex that binds to DRE sequences which suggests that these two proteins are dimeric partners which act coordinately to regulated the expression of a number of genes.

In addition to the high sequence homology at their- N-termini, the Ah-receptor, Sim, and ARNT all have glutamine-rich C-termini. Glutamine-rich sequences have been described in several transcription factors (e.g., Spl and OTF-2) and have been characterized as activation domains. Courey, A. J. & Tjian, R., *Cell* 55:887–98 (1988); Gerster, T., Balmaceda, C. & Roeder, R. G., *EMBO J.* 9:1635–1643 (1990); Laurent, B. C., Treitel, M. A. & Carlson, M., *Mol. Cell. Biol.* 10:5616–5625 (1990). The presence of this domain in the Ah-receptor and ARNT suggests that both proteins may be involved in the transcriptional activation of dioxin-responsive genes. Within the glutamine rich segments of the Ah-receptor and Sim is a concentrated cluster of glutamine residues in which 12 of 21 amino acids in Sim and 11 of 21 in the Ah-receptor are glutamine. Similar glutamine-rich regions have been described in several developmentally regulated and tissue specific gene products from Drosophila to humans. These regions have been termed opa repeats and are defined at the nucleotide level as CAX repeats where X=G,A (encoding glutamine) or c (encoding histidine). Wharton, K. A., Yedvobnick, B., Finnerty, V. G. & Artavanis, T. S., *Cell* 40:55–62 (1985).

Figure 4:
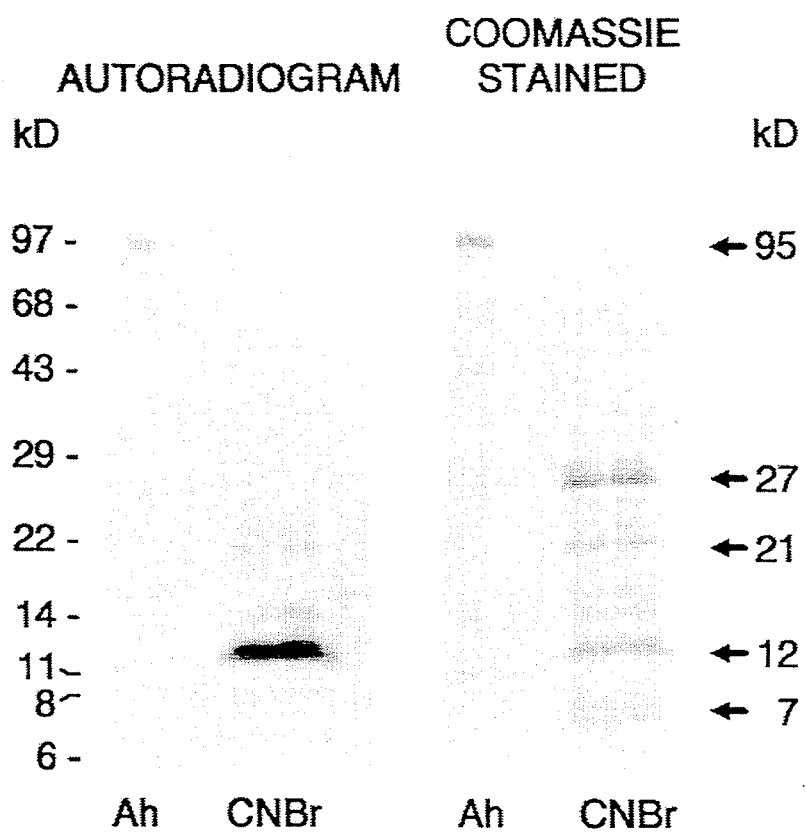
FIG. 4 shows peptide mapping and amino acid sequencing of internal fragments generated by CNBr.

Cyanogen bromide cleavage (CNBr) provides additional information regarding cDNA. CNBr fragmentation experiments provide insights into the domain structure of the Ah-receptor. By photoaffinity labeling the Ah-receptor prior to cleavage with CNBr, the region of the protein which was covalently bound by radioligand was identified. The autoradiogram of the CNBr fragments (See FIG. 4) identifies the 12 kd band as the major photoaffinity labeled fragment (>95% of radiolabel after purification). This locates the photoaffinity ligand bound residue(s) of the Ah-receptor to amino acids 232–334 as defined by the sequence known to follow methionine 231 and the predicted C-terminal cleavage site, methionine 334.

Figure 6B:
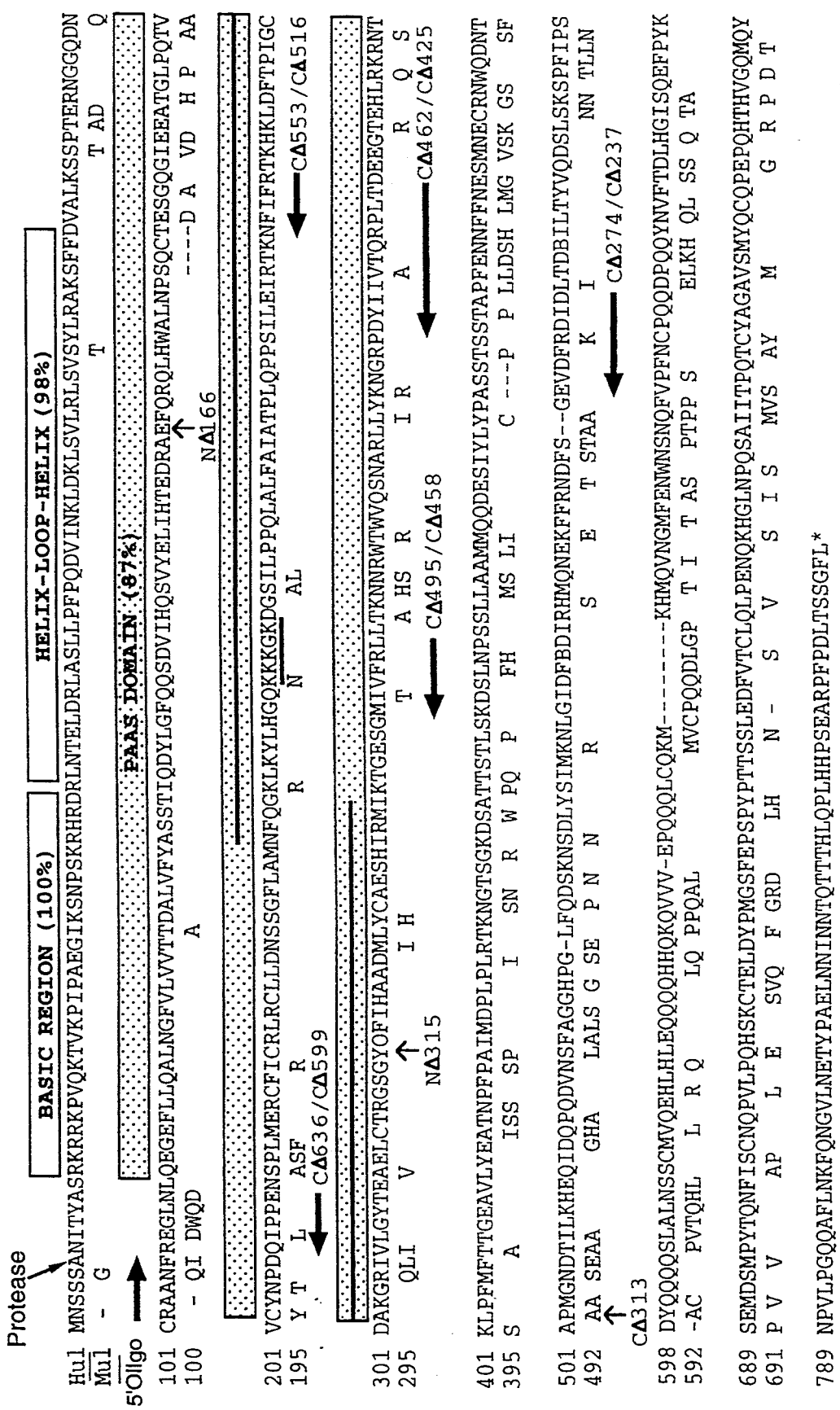
FIG. 6B shows the amino acid sequence of the human Ah-receptor (Hu) and comparison with the murine Ah-receptor.

A comparison of the deduced amino acid sequence of the human and murine Ah-receptor cDNAs revealed that the N-terminal half of the two proteins are highly conserved with 100% sequence identity in the basic region, 98% in the helix-loop-helix domain, and 87% in the PAAS domain. See FIG. 6B. In contrast, the C-terminal amino acid sequence of the two proteins is highly variable, displaying only 60% sequence identity.

Figure 9:
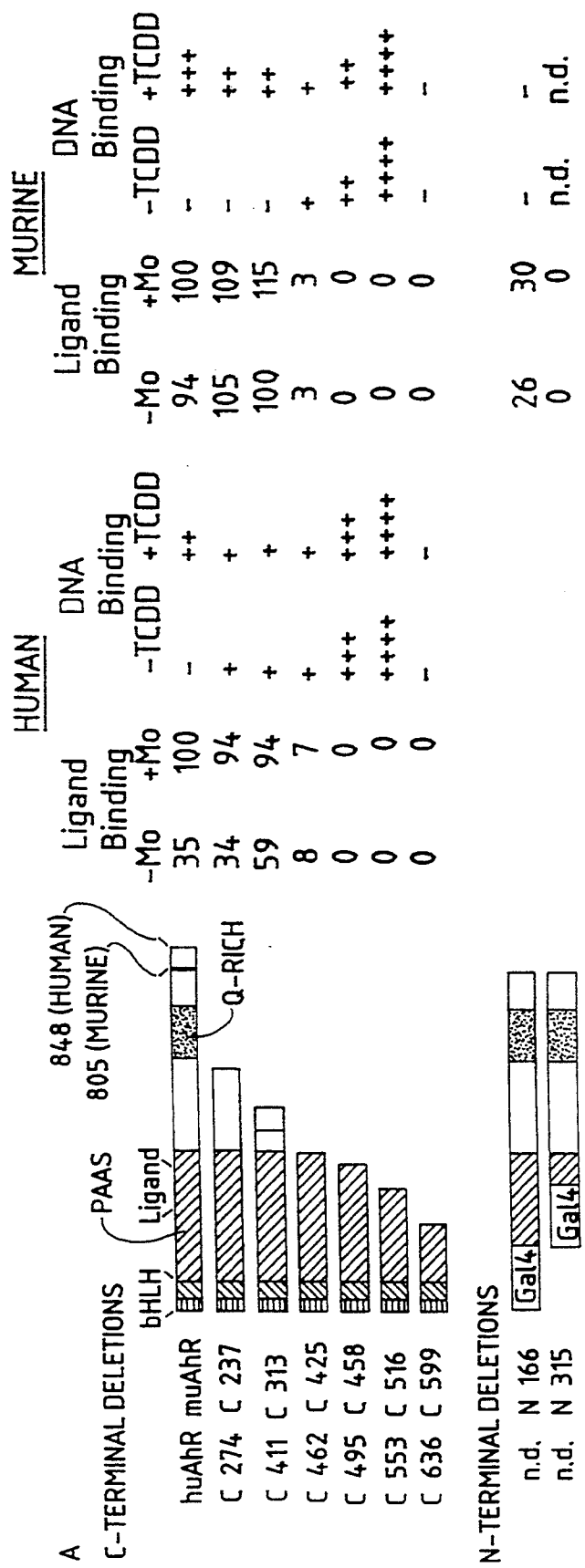
FIGS. 9A & B show deletion analysis of the human and murine Ah-receptors.
Figure 9:
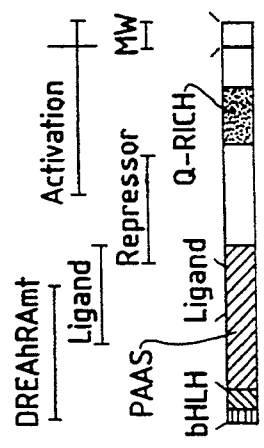
Figure 9A:
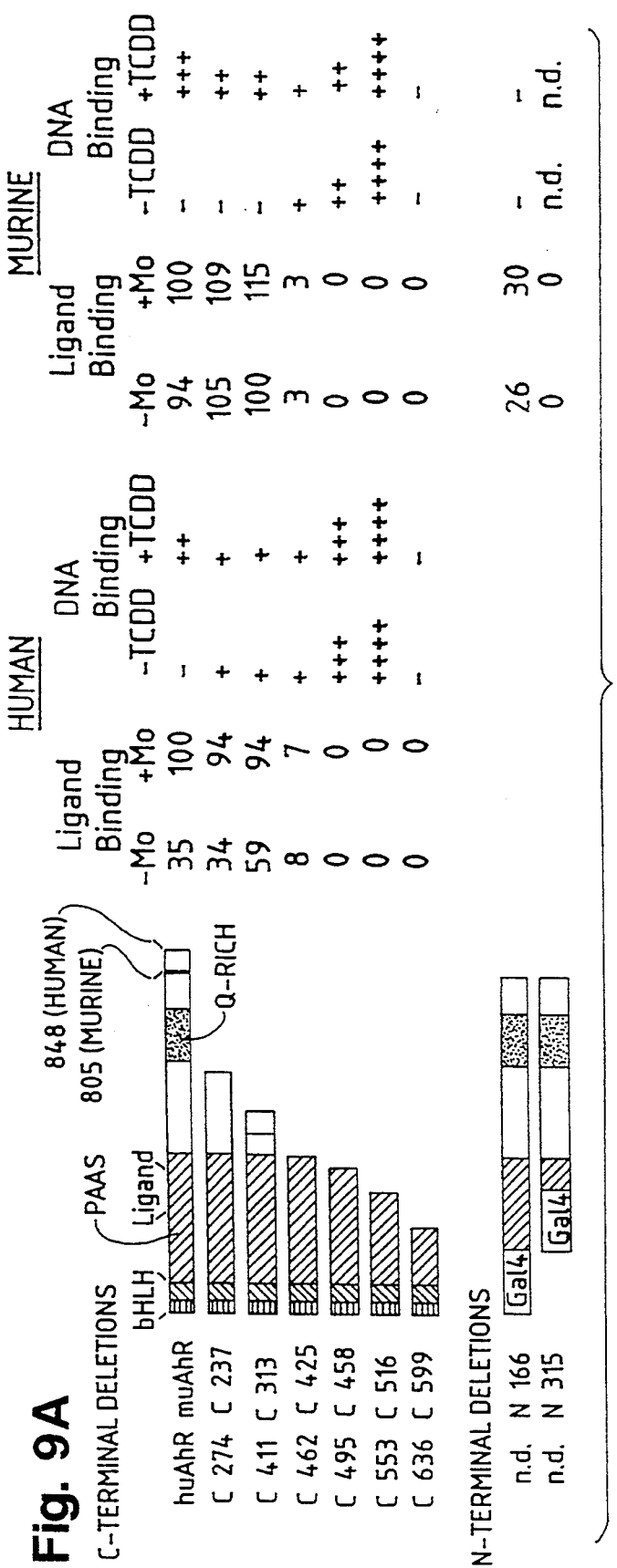
Figure 9B:
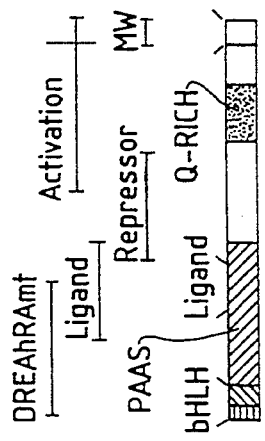

To characterize the functional domain map of the Ah-receptor, a series of deletion mutants were constructed and their capacity to bind ligand and the DRE was analyzed (See FIGS. 9A & B). For the murine receptor, C-terminal deletions of up to 313 amino acids (CΔ313) did not significantly affect ligand binding function. However, the CΔ425 mutant displayed decreased ligand binding by about 95%. Since this mutant retains the ability to bind ligand (about 10-fold over background), and the truncation of 33 additional amino acids from the C-terminus (CΔ458) completely abolished ligand binding activity, CΔ425 can be used to define the approximate C-terminal boundary of the domain required for ligand binding. To define the N-terminal boundary of this domain, N-terminal deletion mutants/chimeras containing the DNA binding domain of the Gal4 protein were used. A fusion protein missing 166 amino acids from the N-terminus (NΔ166) retained the capacity to bind ligand, while the deletion of 315 amino acids from the N-terminus (Na315) abolished ligand binding. Therefore, NΔ166 defined the approximate N-terminal boundary of the ligand binding domain.

Once the ligand binding domain was identified, characterization of the domains required for DRE binding was described. It was predicted that mutations in a number of functionally distinct domains, such a those required for ligand activation, Hsp90 association and dimerization with ARNT would have an impact on DRE binding. Because none of the Ah-receptor constructs bound the DRE in the absence of ARNT and ARNT did not bind the DRE alone, only Ah-receptor/ARNT heterodimers are able to bind to the DRE. It was discovered that the Gal4/Ah-receptor chimera, NΔ166, which was missing in the bHLH domain, did not bind to the DRE. The deletion mutant CΔ516 appeared to define the C-terminal boundary of a domain required for DRE binding suggesting that residues in the PAAS domain as far as 245 residues from the N-terminal basic domain play a role in DRE/Ah-receptor-ARNT complex formation (See FIGS. 9A & B). Finally it was discovered that the domain involved in receptor activation to a DRE binding form was located within the C-terminal 313 amino acids of the protein. This domain is defined by the CΔ237 and CΔ313 mutants which display decreasing ligand-activated DRE binding when compared to the full length receptor, but did not exhibit decreased ligand binding. (See FIG. 9).

Both CΔ458 and CΔ516 bound the DRE without ligand activation. This suggested that the C-terminal deletion of 458 amino acids removed a domain with a role in repressing the DRE binding activity of the receptor. Many laboratories have observed that the presence of oxyanions, such as molybdate lead to dramatic improvements in ligand binding and inhibit ligand activated receptor binding to DNA. Meshinchi, S., Grippo, J. F., Sanchez, E. R., Bresnick, E. H., Pratt, W. B., *J. Biol. Chem.* 263:16809–16817 (1988); Hutchison, K. A., et al., *J. Biol. Chem.* 267:2902–2908 (1992). Molybdate appears to act via stabilization of an Ah-receptor-Hsp90 complex. Manchester, D. K., Gordon, S. K., Golas, C. L., Roberts, E. A., Okey, A. B., *Cancer Res.,* 47:4861–4868 (1987). The effects of molybdate are observed on receptor isolated from essentially all species and murine strains except the receptor isolated from the C57BL/6J mouse. Cuthill, S., Poellinger, L., Gustafsson, J., *J. Biol. Chem.,* 262:3477–3481 (1987). It was observed that ligand binding to the human receptor could be improved (consistingly 3-fold) and DRE binding was completely inhibited by the presence of sodium molybdate, while no changes were observed for the murine form (See FIGS. 9A & B). Since the effect of molybdate on the human Ah-receptor's capacity to bind ligand was highly reproducible, an attempt to map this domain was made. The human deletion mutant CΔ274 exhibited the same molybdate-induced enhancement of ligand binding as the full length human receptor, while the deletion of 411 amino acids (CΔ411) weakened the ability of molybdate to stabilize the receptor. Finally, the deletion of 462 (CΔ462) amino acids from the C-terminus completely abolished the molybdate effect. These results allowed the mapping of the molybdate stabilization domain between mutants CΔ274 and CΔ462 (See FIGS. 9A & B). It was observed that the human receptor mutants CΔ274, CΔ411, and CΔ462 begin to acquire ligand-independent DRE binding. This supports the hypothesis that this domain is involved in the association of the receptor with Hsp90 which acts as a repressor of DRE binding activity.

(iii) Expression of the Ah Receptor

The cDNA molecule can be expressed by a variety of means including in a eukaryotic cell. Also, the Ah receptor and polypeptide derivatives of the Ah receptor can be expressed recombinant techniques when a DNA sequence encoding the relevant molecule is functionally inserted into a vector. By "functionally inserted" is meant in proper reading frame and orientation, as is well understood by those skilled in the art. Typically, the Ah receptor gene will be inserted downstream from a promoter and will be followed by a stop codon, although production as a hybrid protein followed by cleavage may be used, if desired. In general host-cell-specific sequences improving the production yield of Ah receptor and Ah receptor polypeptide derivatives will be used and appropriate control sequences will be added to the expression vector, such as enhancer sequences, polyadenylation sequences, and ribosome binding sites.

Once the appropriate coding sequence is isolated, it can be expressed in a variety of different expression systems, or it can be inserted into the genome for transgenic expression. WO 9203471 is partially set out to provide general background information regarding gene expression in different systems.

Mammalian Expression Systems

A mammalian promoter is any DNA sequence capable of binding mammalian RNA polymerase and initiating the downstream (3') transcription of a coding sequence (e.g. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, typically located within 100 to 200 bp upstream of the TATA box. An upstream promoter element determines the rate at which transcription is initiated and can act in either orientation (Sambrook et al., (1989) "Expression of Cloned Genes in Mammalian Cells," in *Molecular Cloning: A Laboratory Manual*, 2nd ed.).

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallothionein gene, also provide useful promoter sequences. Expression may be either constitutive or regulated (inducible), and depending on the promoter can be induced with glucocorticoid in hormone-responsive cells.

The presence of an enhancer element (enhancer), combined with the promoter elements described above, will typically increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nuclectide from the promoter (Maniatis et al., (1989) *Molecular Biology of the Cell*, 2nd ed.). Enhancer elements derived from viruses may be particularly useful, because they typically have a broader host range. Examples include the SV40 early gene enhancer (DiJkema et al. (1985) *EMBO J.* 4:761) and the enhancer/promoters derived from the long terminal repeat (LTR) of the Rous Sarcoma Virus (Gormal et al., (1982b) *Proc. Natl. Acad. Sci.* 79:6777) and from human cytomegalovirus (Boshart et al., (1985) *Cell* 41:521). Additionally, some enhancers are regulatable and become active only in the presence of an inducer, such as a hormone or metal ion (Sassone-Corsi and Borelli (1986) *Trends Genet.* 2:215; Maniatis et al., (1987) *Science* 236:1237).

A DNA molecule may be expressed intracellularly in mammalalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell. The adenovirus tripartite leader is an example of a leader sequence that provides for secretion of a foreign protein in mammalian cells.

Typically, transcription termination and polyadenyiation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation (Birnstiel et al., (1985) *Cell* 41:349; Proudfoot and Whitelaw (1988) "Termination And 3' end processing of eukaryotic RNA." In *Transcription and splicing* (ed. B. D. Hames and D. M. Glover); Proudfoot (1989) *Trends Biochem. Sci.* 14:105).

These sequences direct the transcription of an mRNA which can be translated into the polypeptide encoded by the DNA. Examples of transcription terminator/polyadenylation signals include those derived from SV40 (Sambrook et al (1989) "Expression of cloned genes in cultured mammalian cells." In *Molecular Cloning: A Laboratory Manual*).

Some genes may be expressed more efficiently when intrans (also called intervening sequences) are present. Several cDNAs, however, have been efficiently expressed from vectors that lack splicing signals (also called spliced donor and acceptor sites) (see e.g., Gothing and Sambrook (1981) *Nature* 293:620). Intrans are intervening noncoding sequences within a coding sequence that contain spliced donor and acceptor sites. They are removed by a process called "splicing" following polyadenylation of the primary transcript (Nevins (1983) *Ann. Rev. Biochem*, 52:441; Green (1986) *Annu. Rev. Genet.* 20:671; Padgett et al., (1986) *Annu. Rev. Biochem.* 55:1119; Krainer and Maniatis (1988) "RNA splicing." In *Transcription and solicina* (ed. B. D. Hames and D. M. Glover)).

Typically, the above described components, comprising a promoter, polyadenylation signal, and transcription termination sequence are put together into expression constructs. Enhancers. introns with functional splice donor and acceptor sites, and leader sequence also be included in an expression construct. If desired. Expression constructs are often maintained in a replicon, such as an extrachromosomal element (e.g., plasmids) capable of stable maintenance in a host, such as mammalian cells or bacteria. Mammalian replication systems include those derived from animal viruses, which require transacting factors to replicate. For example, plasmids containing the replication systems of papovaviruses, such as SV40 (Gluzman (1981) *Cell* 2523:175) or polyomavirus, replicate to extremely high copy number in the presence of the T antigen. Additional examples of mammalian replicons include those derived from bovine papillomavirus and Epstein-Barr virus. Additionally, the replicon may have two replication systems, thus allowing it to be maintained, for example, in mammalian cells for expression and in a procaryotic host for cloning and amplification. Examples of such mammalian-bacteria shuttle vectors include pMT2 (Kaufman et al., (1989) Mol. Cell. Biol. 9:946 and pHEBO (Shimizu et al., (1986) Mol. Cell. Biol. 6:1074).

Baculovirus Expression System

A baculovirus promoter is any DNA sequence capable of binding a baculovirus RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus promoter may also have a second domain called an enhancer, which, if present, is usually distal to the structural gene. Expression may be either regulated or constitutive.

Sequences encoding genes abundantly transcribed at late times in the infection cycle provide particularly useful promoter sequences. Examples include sequences derived from the polyhedrin (Friesen et al., (1986) "The Regulation of Baculovirus Gene Expression," in: The Molecular Biology of Baculoviruses (ed. Walter Doerfler); E.P.O. Pub. Nos. 127,839 and 155,476) and p10 (Vlak et al., (1988) J. Gen. Virol. 69:765) genes. A DNA molecular may be expressed intracellularly. A promoter sequence may be directly linked with the DNA molecule, in which the case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative to direct expression. Typically, a DNA sequence encoding the N-terminal portion of an endogenous yeast protein, or other stable protein, is fused to the 5' end of heterologous coding sequences. Upon expression, this construct will provide a fusion of the two amino acid sequences. For example, the N-terminus of the polyhedrin gene may be linked at the 5' terminus of a foreign gene and expressed in yeast. The DNA sequence at the junction of the two amine acid sequences may or may not encode a cleavable site. See e.g., Luckow et al., (1988) Bio/technology 6:47.

Alternatively, foreign proteins can also be secreted from the cell by creating chimeric DNA molecules that encode a fusion protein comprised of a leader sequence fragment that provides for secretion of the foreign protein in insects. The leader sequence fragment typically encodes a signal peptide comprised of hydrophobic amino acids which direct the secretion of the protein from the cell.

DNA encoding suitable signal sequences can be derived from genes for secreted insect or baculovirus proteins, such as the baculovirus polyhedrin gene (Carbonell et al., (1988) Gene 3:409). Alternatively, leaders of non-baculovirus origin, such as those derived from genes encoding human alpha-interferon (Maeda et al., (1985) Nature 315:592), human gastrin-releasing peptide (Lebacq-Verheyden et al., (1988) Molec. Cell. Biol. 8:3129), human IL-2 (Smith et al., (1985) Proc. Natl. Acad. Sci. USA 82:8404), mouse IL-3 (Miyajima et al., (1987) Gene 58:273), and human glucocerebrosidase (Martin et al., (1988) DNA 7:99) also provide for secretion in insects.

Typically, transcription termination sequences recognized by insects are regulatory regions located 3' to the translation stop codon, and thus together with the promoter flank the coding sequence, These sequences direct the transcription of an mRNA which can be translated into the polypeptide encoded by the DNA. Examples include transcription termination sequences derived from the polyhedrin gene (Miller et al., (1988) Ann. Rev. Microbiol. 42:177). Prior to insertion of the foreign gene into the baculovirus genome, the above described components, comprising a promoter, leader (if desired), coding sequence of interest, and transcription termination sequence, are typically put together into an intermediate transplacement construct. Intermediate transplacement constructions are often maintained in a replicon, such as an extrachromosomal element (e.g., plasmids) capable of stable maintenance in a host, such as bacteria. The replicon will have a replication system, thus allowing it to be maintained in a prokaryotic host for cloning and amplification. The promoter and transcription termination sequence of the construct will typically comprise a 2.5 kb section of the baculovirus genome for integration of the foreign gene into the baculovirus genome by double crossover recombination events, producing a baculovirus expression vector (Miller et al., (1989) Bioessays 4:91). The baculovirus expression vector is typically packaged into an infectious recombinant baculovirus.

When using baculovirus expression vectors, selectable markers are, such as antibiotic resistance genes, are generally not used. Selection is typically by visual inspection for occlusion bodies. Examples are given elsewhere in this specification of the use of selectable markers.

Recombinant baculovirus expression vectors have been developed for infection into several insect cells. For example, recombinant baculoviruses have been developed for inte alia: Aedes aegytpi, Autographa californica, Bombyx mori, Drosophila melangaster, Heliothis zea, Spodopters Frugiperda, and Trichoplusiain (P.C.T. WO 89/046699; Carbonell et al., (1985) J. Virol. 56:153: Smith et al., (1983) Mol. Cell. Biol. 3:2156; Wright (1986) Nature 321:718; See generally, Fraser et al., (1989) In Vitro Cell. Dev. Biol. 25:225).

Methods of introducing exogenous DNA into insect hosts are well-known in the art, and typically include either the transfection of host insect cells with DNA or the infection of insect cells or live insects, usually larvae, with virus. Transfection procedures are based on the calcium phosphate procedure originally developed for mammalian cells (Graham et al., (1973) Virology 52:456). DNA transfection and viral infection procedures usually vary with the insect genus to be transformed. See e.g. Autograph (Carstens et al., (1980) Virology 101:311), Heliothis (virescens) (P.C.T. Pub. No. W088/02030), Spodoptera (Kang (1988) "Baculovirus Vectors for Expression of Foreign Genes, " in Advances in Virus Research, vol. 35).

Bacterial Expression Systems

A bacterial promoter is any DNA sequence capable of binding bacterial RNA polymerase and initiating the downstream (3') transcription of a coding sequence (e.g., structural aene) into mRNA. A promoter will have a transcription initiation region which is usually placed proximal to the 5' end of the coding sequence.

This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli* (Raibaud et al., (1984) *Annu. Rev. Genet.* 18:173). Regulated expression may therefore be either positive or negative, thereby either enhancing or reducing transcription.

Sequences encoding metabolic pathway enzymes provide particularly useful promoter sequences. Example include promoter sequences derived from sugar metabolizing enzymes, such as galactose, lactose (lac) (Chang et al., (1977) *Nature* 198:1056), and maltose. Additional examples include promoter sequences derived from biosynthetic enzymes such as tryptophan (trp) (Goeddel et al., (1980) i Nuc. Acids Res., 8:4057; Yelverton et al., (1981) *Nucl. Acids Res.* 9:731; U.S. Pat. No. 4,738,921; E.P.O. Pub. Nos. 36,776 and 121,775). The y-lactamase (bla) promoter system (Weissmann (1981) "The cloning of interferon and other mistakes." In *Interferon* 15 3 (ed. I. Gresser), bacteriophage lambda PL (Shimatake et al., (1981) *Nature* 292:128) and T5 (U.S. Pat. No. 4,689,406) promoter systems also, provide useful promoter sequences. In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter comprised of both tro promoter and lac operon sequences that is regulated by the lacrepressor (Amann et al., (1983) *Gene* 25:167; de Boer et al., (1983) *Proc. Natl. Acad. Sci.* 80:21). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to product high levels of expression of some genes in prokaryotes. The bacteriophage T7 RNA polymerase/promoter system is an example of a coupled promoter system (Studier et al., (1985) *Proc. Natl. Acad. Sci.* 82:1074). In addition, a hybrid promoter can also be comprised of a bacteriophage promoter and an *E. coli* operator region (E.P.O. Pub. No. 267,851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon (Shine et al., (1975) *Nature* 254:34). The SD sequence is thought to promote binding of mRNA to the ribosome by the pairing of bases between the SD sequence and the 3' and of *E. coli* 16S rRNA (Steitz et al., (1979) "Genetic signals and nucleotide sequences in messenger RNA." In *Biological Regulation and Development: Gene Expression* (ed. R. F. Goldberger)). To express eukaryotic genes and prokaryotic genes with weak ribosome-binding site (Sambrook et al., (1989) Expression of Cloned genes in *Escherichia coli.*" In *Molecular Cloning: A Laboratory Manual*).

A DNA molecule may be expressed intracellularly. A promoter sequence may be directly linked with the DNA molecule, in which case the first amino acid at the N-terminus will always be a methionine, which is encoded by the ATG start codon. If desired. methionine at the N-terminus may be cleaved from the protein by in vitro incubation with cyanogen bromide or by either in vivo or in vitro incubation with a bacterial methionine N-terminal peptidase (E.P.O. Pub. No. 219,237).

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene (Nagai et al., (1984) *Nature* 309:810). Fusion proteins can also be made with sequences from the lac Z (Jia et al., (1987) *Gene* 60:197), trpE (Allen et al., (1987) *J. Biotechnol.* 5:93; Makoff et al., (1989) *J. Gen. Microbiol.* 135:11), and CheY (E.P.O. Pub. No. 324,647) genes. The DNA sequence at the junction of the two amino acid sequences may or may not encode a cleavable site. Another example is a ubiquitin fusion protein. Such a fusion protein is made with the ubiquitin region that preferably retains a site for a processing enzyme (e.g. ubiquitin specific processing-protease) to cleave the ubiquitin from the foreign protein. Through this method, native foreign protein can be isolated (Miller et al., 91989) Bio/Technology 7:698).

Alternatively, foreign proteins can also be secreted from the cell by creating chimeric DNA molecules that encode a fusion protein comprised of a signal peptide sequence fragment that provides for secretion of the foreign protein in bacteria (U.S. Pat. No. 4,336,336). The signal sequence fragment typically encodes a signal peptide comprised of hydrophobic amino acids which direct the secretion of the protein from the ceil. The protein is either secreted into the growth media (gram-positive bacteria) or into the periplasmic space, located between the inner and outer membrane of the cell(-gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) (Masui et al., (1983), in: *Experimental Manipulation of Gene Expression;* Ghrayeb et al., (1984) *EMBO J.* 3:2437) and the *E. coli* alkaline phospnatase signal sequence (phoA) (Oka et al., (1985) *Proc. Natl. Acad. Sci.* 2:7212). As an additional example, the signal sequence of the alphaamylase gene from various Bacillus strains can be used to secrete heterologous proteins from *B. subtilis* (Palva et al., (1982) *Proc. Natl. Acad. Sci. USA* 79:5582; E.P.O. Pub. No. 244,042).

Typically, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the above described components, comprising a promoter, signal sequence (if desired), coding sequence of interest, and transcription termination sequence, are put together into expression constructs. Expression constructs are often maintained in a replicon, such as an extrachromoscmal element (e.g., plasmids) capable of stable maintenance in a host, such—as bacteria. The replicon will have a replication system, thus allowing it to be maintained in a procaryotic host either for expression or for cloning and amplification. In addition, a replicon may be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various Bacillus strains integrate into the Bacillus chromosome (E.P.O. Pub. No. 127,328). Integrating vectors may also be comprised of bacteriophage or transposon sequences.

Typically, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline (Davies et al., (1978) *Annu. Rev. Micrcbiol.* 2:469). Selectable markers may also include biosynthetic genes, such as those in the histidine, tryptophan, and leucine biosynthetic pathways.

Alternatively, some of the above described components can be put together in transformation vectors. Transformation vectors are typically comprised of a selectable market that is either maintained in a replicon or developed into an integrating vector, as described above.

Expression and transformation vectors, either extrachromosomal replicons or integrating vectors, have been developed for transformation into many bacteria. For example, expression vectors have been developed for, inter alia, the following bacteria: *Bacillus subtilis* (Palva et al., (1982) *Proc. Natl. Acad. Sci. USA* 79:5582; E.P.O. Pub. Nos. 36,259 and 63,953; P.C.T. WO 84/04541), *escherichia coli* (Shimatake et al., (1981) *Nature* 292:128; Aman et al., (1985) *Gene* 40:183; Studier et al., (1986) *J. Mol. Biol.* 189:113; E.P.O. Pub. Nos. 36,776, 136,829 and 136,907; U.K. Patent Application Serial No. 8418273), *Streptococcus cremoris* (Powell et al., (1988) *Appl. Environ. Microbiol.* 54:655); *Streptococcus liyidans* (Powell et at., (1988) *Appl. Environ. Microbiol.* 54:655), *Streptomyces lividans* (U.S. Pat. No. 4,745,056).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Transformation procedures usually vary with the bacterial species to be transformed. See e.g., (Masson et al., (1989) *FEMS Microbiol. Lett.* 60:273; Palva et al., (1982) *Proc. Natl. Acad. Sci. USA* 79:5582; E.P.O. Pub. Nos. 36,259 and 63,953; P.C.T. WO 84,/04541, Bacillus), (Miller et al., (1988) *Proc. Natl. Acad. Sci.* 85:856; Wange et al., (1990) *J. Bacteriol.* 172:949, Campylobacter), (Cohen et al., (1973) *Proc. Natl. Acad. Sci.* 69:2110; Dower et al., (1988) *Nucleic Acids Res.* 16:6127; Kushner (1978) "An improved method for transformation of *Escherichia coli* with Eo-lEl-derived plasmids." In *Genetic Engineering: Proceedings of the International Symposium on Genetic Engineering* (eds. H. W. Boyer and S. Nicosia); Mandel et al., (1970) *J. Mol. Biol.* 53:159; Taketo (1988) *Biochem. Biophys. Acta* 949:318; Escherichia) (Chassy et al., (1987) *FEMS Microbiol. Lett.* 44:173 Lactobacillus); (Fiedler et al., (1988) *Anal. Biochem.* 170:38, Pseudomonas); (Augustin et al., (1990) *FEMS Microbiol. Lett* 66:203, Staphylococcus) , (Barany et al., (1980) *Bacteriol.* 144:698; Harlander (1987) "Transformation of *Streptococcus lactis* by electroporation," in: *Streptococcal Genetics* (ed. J. Ferretti and R. Curtiss III); Perry et. al., (1981) *Infec. Immun.* 32:1295; Powell et al., (1988) *Anal. Environ. Microbiol.* 54:655; Somkuti et al., (1987) *Proc. 4th Evr. Cona. Biotechnology* 1:412, Streptococcus. Alternatively, foreign proteins can also be targeted to the membrane of a bacterial cell. If the cDNA expression construct includes an amino-terminal hydrophobic leader sequence, and one or more additional internal hydroohobic domains of sufficient size to span the cell membrane (typically —20 amino acids), the resulting protein can be targeted to the cell membrane and retained there in a conformation dependent on the nature and characteristics of the internal hydrophobic domains. (Wickner W. T. and Lodish H. F., *Multiple Mechanisms of Protein Insertion into and Across Membranes, Science* 300:400–407 (1985)). (Hereby incorporated by reference).

Description: Yeast Expression System

A yeast promoter is any DNA sequence capable of binding yeast RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydorgenase (ADH) (E.P.O. Pub No. 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (E.P.O. Pub. No. 329203). The yeast PHO gene, encoding acid phosphatase, also provides useful promoter sequences (Myanohara et al., (1983) Proc. Natl. Acad. Sci. USA 80:1).

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (E.P.O. Pub No. 164556). Furthermore, a yeast promoter can include naturally occurring promoters of non-yeast origin that have the ability to bind yease RNA polymerase and initiate transcription. Examples of such promoters include inter alia, (Cohen et al., (1980) Proc. Natl. Acad. Sci. USA 77:1078: Henikoff et al., (1981) Nature 283:835; Hollenberg et al., (1981) Curr. Topics Microbiol. Immunol. 96:119; Hollenberg et al., (1979) "The Expression of Bacterial Antibiotic Resistance Genes in the Yeast Saccharomyces cerevisiae," in Plasmids of Medical, Environmental and Commercial Importance (eds. K. N. Timmis and A. Puhler; Mercerau-Puigalon et al., (1980) Gene 11:163; Panthier et al., (1980) Curr. Genet. 2:109).

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative to direct expression. Typically, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See e.g. E.P.O. Pub. No. 196056. Another example is a ubiquitin fusion protein. Such a fusion protein is made with the ubiquitin region that preferably retains a site for a processing enzyme (e.g. ubiquitin-specific processing protease) to cleave the ubiquitin from the foreign protein.

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene (E.P.O. Pub. No. 13873; J.P.O. Pub. No. 62,096,086) and the A-factor gene (U.S. Pat. No. 4,588,684). Alternatively, leaders of non-yeast origin, such as an interferon leader, exist that also provide for secretion in yeast (E.P.O. Pub. No. 60057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (U.S. Pat. Nos. 4,546,083 and 4,870,008; E.P.O. Pub. No. 324274). Additional leaders employing an alpha-factor leader fragment that provides for secretion include hybrid alpha-factor leaders made with a presequence of a first yeast, but a pro-region from a second yeast slphafactor. (See e.g., P.C.T. WO 89/02463).

Typically, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Typically, the above described components, comprising a promoter, leader (if desired), coding sequence of interest, and transcription termination sequence, are put together into expression constructs. Expression constructs are often maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 (Botstein et al. (1979) Gene 8:17–24), pCl/1 (Brake et al., (1984) Proc Natl. Acad. Sci. USA 81:4642–4646), and YRp17 (Stinchcomb et al., (1982) J. Mol. Biol. 158:157). In addition, a replicon may be either a high or low copy number plasmid. A high copy number plasmid will generally have a copy number ranging from about 5 to about 200, and typically about 10 to about 150. A host containing a high copy number plasmit will preferably have at least about 10, and more preferably at least about 20. Either a high or low copy number vector may be selected, depending upon the effect of the vector and the foreign protein on the host. See e.g. Brake et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome (Orr-Weaver et al., (1983) *Methods in Enzymol.* 101:228–245). An integrating vector may be directed to a specific locus in yeast by selecting the appropriate homologous sequence for inclusion in the vector. See Orr-Weaver et al., supra. One or more expression construct may integrate, possibly affecting levels of recombinant protein produced (Rine et al., (1983) *Proc. Natl. Acad. Sci. USA* 80:6750). The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Typically, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRPI, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUPI allows yeast to grow in the presence of copper ions (Butt et al., (1987) *Microbiol. Rev.* 51:351).

Alternatively, some of the above described components can be put together into transformation vectors. Transformation vectors are typically comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* (Kurtz, et al., (1986) *Mol. Cell. Biol.* 6:142), *Candida maltosa* (Kunze, et al., (1985) *J. Basic Microbiol.* 25:141). *Hansenula polymorpha* (Gleeson, et al., (1986) *J. Gen. Microbiol.* 132:3459; Roggenkamp et al., (1986) *J. Gen. Genet.* 202:302), *Kluyveromyces fragilis* (Das, et al., (1984) *J. Bacteriol.* 158:1165), Kluyveromyceslactis (De Louvencourt et al. (1983) *J. Bacteriol.* 154:737; Van den Berg et al., (1990) *Bio/Technology* 8:135), *Pichia guillerimondii* (Kunze et al., (1985) *J. Basic Microbiol.* 25:141), *Pichia pastoris* (Cregg, et al., (1985) *Mol. Cell. Biol.* 5:3376; U.S. Pat. Nos. 4,827,148 and 4,929,555), *Saccharomyces cerevisiae* (Hinnen et al., (1978) *Proc. Natl. Acad. Sci. USA* 75:1929; Ito et al., (1983) *J. Bacteriol.* 153:163) *Schizosaccharomyces pombe* (Beach and Nurse (1981) *Nature* 300:706), and *Yarrowia lipolytica* (Davidow, et al., (1985) *Curr. Genet.* 10:380471 Gaillardin, et al., (1985) *Curr. Genet.* 10:49).

Methods of introducing exogenous DNA into yeast hosts are well-known in the art, and typically include either the transformation of spheroplasts or of intact yeast cells treated with alkali cations. Transformation procedures usually vary with the yeast species to be transformed. See e.g., (Kurtz et al. (1986) *Mol. Cell. Biol* 6:142; Kunze et al., (1985) *J. Basic Microbiol.* 25:141; Cardida); (Gleeson et al., (1986) *J. Gen. Microbiol.* 132:3459; Roggenkamp et al., (1986) *Mol. Gen. Genet.* 202:302; Hansenula; (Das et al., (1984) *J. Bacteriol.* 158:1165: De Louvencourt et al., (1983) *J. Bacteriol* 154:1165; Van den Berg et al., (1990) *Bio/Technology* 8:135; Kluyveromyces); (Cregg et al., (1985) *Mol. Cell. Biol.* 5:3376; Kunze et al., (1985) *J. Basic Microbiol.* 25:141; U.S. Pat. Nos. 4,837,48 and 4,929,555; Pichia/(- Hinnen et al., (1978) *Proc. Natl. Acad. Sc. USA* 75:1929; Ito et al., (1983) *J. Bacteriol.* 153:163 Saccharomyces); (Beach and Nurse (1981) *Nature* 300:706; Schizosaccharomces); (Davidow et al., (1985) *Curr. Genet.* 10:39; Gaillardin et al.(1985) *Curr. Genet.* 10:49; Yarrowia. Alternatively, foreign proteins can also be targeted to the membrane of a yeast cell. If the cDNA expression construct includes an amino-terminal hydrophobic leader sequence, and one or more additional internal hydrophobic domains of sufficient size to span the cell membrane (typically −20 amino acids), the resulting protein can be targeted to the cell membrane and retained there in a conformation dependent on the nature and characteristics of the internal hydrophobic domains. (Wickner W. T. and Lodish H. F., *Multiple Mechanisms of Protein Insertion into and Across Membranes*, Science 300:400–407 (1985)). (Hereby incorporated by reference).

(iv) The Utility of the Invention

Figure 10:
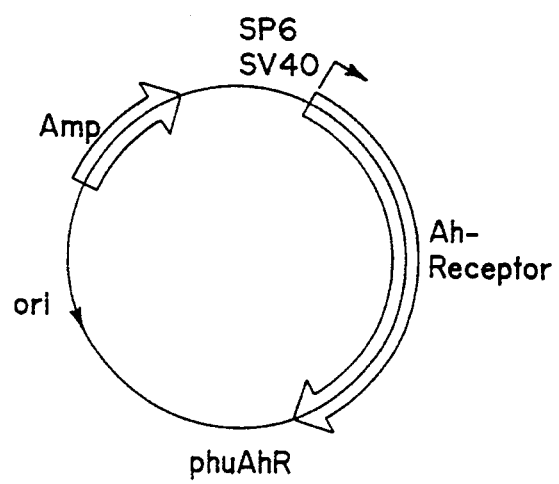
FIG. 10 shows an example of a mammalian expression vector for human AhR.

Assays that recognize the presence of aromatic halogenated toxins such as those in the dioxin family have been developed. Poland et al., U.S. Pat. No. 5,128,244 ('244) hereby incorporated by reference. This patent provides a method of detecting environmental pollutants that are related to 2,3,7,8-tetrachlorodibenzo-p-dioxin (TCDD). The Ah receptor is used in '244 as a reagent to specifically bind the radiolabeled agonist, [$^{125}$I]-2-iodo-7,8-dibromodibenzo-p-dioxin. Chemicals and environmental samples that compete with this compound for receptor occupancy are assumed to be a receptor agonist and thereby potential toxicants. One of the problems in applying this method lies in the availability of receptor preparations for the assay, especially preparations for human cells. The human and murine cDNA clones can be used to generate significant concentrations of purified Ah-receptor for use in the assay described in the '244 patent or in other assays as well. This can be accomplished by cloning the cDNAs into vectors which allow expression of the protein. An example of a mammalian vector that can be used to generate human AhR is provided in FIG. 10. Other expression systems include, but are not limited to: 1) in vitro expression in reticulocyte lysates, 2) baculovirus, 3) vaccinia virus, 4) yeast, 5) mammalian cells and 6) bacteria.

Figure 11:
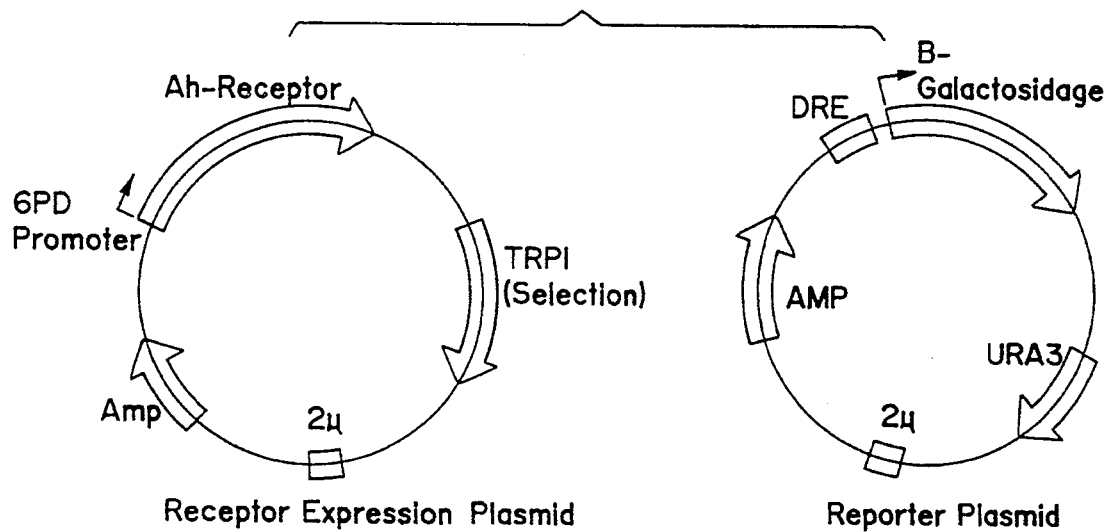
FIG. 11 shows an example of a receptor expression plasmid and a reporter plasmid.

The invention also provides a method of generating recombinant organisms that can serve as biomonitors for environmental pollutants. More specifically, genetically engineered eukaryotic organisms can be engineered to express two plasmids that can be used to detect environmental pollutants and which regulates the expression of heterologous reporter genes. The first plasmid contains either a murine or human cDNA that encodes a recombinant Ah receptor that can be used in cell culture to regulate the expression of a heterologous reporter gene such as β-galactosidase or luciferase in an agonist dependent manner. See FIG. 11. Organisms such as yeast or mammalian cells can be used. The advantage in using yeast is that it is easy to grow and inexpensive to maintain as a culture. The second plasmid contains the dioxin responsive element (DRE). The DRE lies upstream of a reporter gene (such as β-galactosidase or luciferase) and is the site where the Ah-receptor binds. See FIG. 11. If an enviromental pollutant, such as dioxin is present, the dioxin will bind to the Ah receptor generated from the first plasmid. The ligand-bound Ah receptor will then interact with the DRE in the second plasmid. The interaction of the Ah receptor with the DRE will activate the reporter gene. The reporter gene can then assayed to determine if dioxin is present. This method therefore, can be used out in the environment to monitor for the presence of environmental pollutants such as dioxin.

The Ah-receptor cDNA can be used to detect individuals or populations that have altered susceptibility to the toxicity of TCDD and related compounds. Strains of mice exist that have markedly different sensitivities to the effects of receptor agonists. The molecular mechanisms underlying this differential sensitivity are related to subtle sequence differences in the gene that encodes the Ah-receptor. These mutations lead to minor structural differences in receptor function, such that resistant strains of mice have receptors that do not bind agonist as tightly and thereby do not respond as easily. Similar mutations can be identified in human populations. Once these mutations are identified, the target region can be identified, and populations screened using PCR to amplify genomic DNA and sequence. Sequence primers for these assays will be derived from the cDNA and genomic clones of the Ah-receptor.

The invention can also be used to generate polyclonal or monoclonal antibodies. The fusion of mouse myeloma cells and spleen cells from immunized mice by Kohler and Milstein in 1975 (*Nature* 256:495–497 (1975)) demonstrated for the first time that it was possible to obtain a continuous cell line making homogeneous (so-called "monoclonal") antibody. Since this seminal work, much effort has been directed to the production of various hybrid cells (called "hybridomas") and to the use of the antibody made by these hybridomas for various scientific investigations. In order to produce a monoclonal antibody, a hybridoma clone will have to be produced. The hybridoma can be produced by standard techniques. The hybridoma is produced from the fusion of mouse myeloma cells with splenocytes obtained from a mouse hyperimmunized with single cell suspension containing the Ah-receptor that has been digested enzymatically. Next, the hybridoma would be transferred to a growth solution that kills off the unfused cancer cells; the unfused spleen cells will die by themselves. The hybridoma would then begin producing antibodies to the antigen initially injected into the mouse.

EXAMPLE 1: Purification of the Ah Receptor From the C57BL/6J Mouse

Materials and Methods Chemicals.

Activated charcoal, grade PX-21, was a gift from Amoco Research Corp. (Chicago, Ill.). Bacto-Gelating was from Difco Laboratories (Detroit, Mich.). Glacial acetic acid, trichloroacetic acid, and isopropyl alcohol (all reagent grade) were from Fisher Scientific (Fair Lawn, N.J.). Formaldehyde solution (37% v/v), stabilized with 10% methanol (v/v), was from Mallincrodt (St. Louis, Mo.). Silver nitrate was from Amend Drug and Chemical Co. (Irvington, N.J.). HPLC-grade acetonitrile, methanol, and n-propyl alcohol were from Burdick and Jackson Laboratories, Inc. (Muskegon, Mich.). Lithium dodecyl sulfate was from Gallard-Schlessinger Industries Inc. (New York). DEAE-cellulose (DE52) was from Whatman (Clifton, N.J.). Glycerol and formic acid (88%, v/v) were from J. T. Baker (Phillipsburg, N.J.). SDS and ammonium persulfate were from Bethesda Research Laboratories (Gaithsburg, Md.). SDS-PAGE molecular weight standards, bromphenol blue, N,N'-methylene-bis-acrylamide, and acrylamide (99% pure) were from Bio-Rad (Richmond, Calif.). Soybean trypsin inhibitor, Coomassie blue-R250, EGTA, EDTA, Tris (free acid and sodium salt), dithiothreitol, β-mercaptoethanol, phosphocellulose (50–150 μM), sodium azide, CAPS (free acid), MOPS (free acid and sodium salt), and Nonidet P-40 were purchased from Sigma Chemical Co. (St. Louis, Mo.). TFA (99% pure) and dimethyl sulfoxide (anhydrous, 99% pure) were from Aldrich Chemical Co. (Milwaukee, Wis.). Water used in preparation of buffers was deionized; water used in HPLC and staining of gels was deionized and passed through a Milli-Q reaent water system (Millipore, Bedford, Mass.).

Buffers.

MN represents the stock buffer, which contains 25 mM MOPS and 0.02% sodium azide (W/v), pH 7.5 at 4°. MβENG is the stock buffer plus 10 mM β-mercaptoethanol, 1 mM EDTA, and 10% (v/v) glycerol. Electrophoresis sample buffer was 2% lithium dodecyl sulfate (w/V), 62.5 mM Tris, 12.5% glycerol (v/v), 2 mM EDTA, 0.001% bromphenol blue (w/v), and 20 mM dithiothreitol, pH 6.8 at 4°. CM buffer is 10 mM CAPS and 10% (v/v) methanol, pH 11.0 at 20°.

Synthesis of Radioligands.

The photoaffinity ligand 2-azido-3-[$^{125}$I]iodo-7,8-dibromodibenzo-p-dioxin and the reversible raioligand of the Ah receptor 2-[$^{125}$I]iodo-7,8-dibromodibenzo-p-dioxin were synthesized as described previously. Kumar, V., and Chambon, P., *Cell* 55:145–156 (1988); Poland, A., Glover, E., Ebitino, F. H., and Kende, A. S., *J. Biol. Chem.* 261:6352–6356 (1986). These radioligands were prepared at specific radioactivities of 2176 Ci/mmol and were essentially pure, as indicated by RP-HPLC.

Animals and cytosol preparation.

C57BL/6J mice were purchased from The Jackson Laboratory (Bar Harbor, Me.) and bred in our laboratory. Adult male and female mice were killed by cervical dislocation and their livers were removed, rinsed with ice-cold KCl (150 mM), homogenized in 9 volumes of MβENG buffer plus 5 mM EGTA, and subjected to centrifugation at 10,000×g for 20 minutes at 4°. The postmitochondrial supernatant was carefully removed to avoid contamination by the surface lipid layer, and the membrane fraction was pelleted by centrifugation at 105,000×g for 1 hour at 4°. The cytosolic fraction (supernatant) was separated from the surface lipids and microsomal pellet an was stored at −80° until processed further.

Photoaffinity labeling.

Cytosol prepared from 300 grams of liver (total volume, 2 liters, 8–9 mg of protein/ml) was thawed in a warm water bath (37°) for approximately 1 hour. One twentieth of the cytosol (approximately 100 ml) was then removed and diluted with MENG buffer to 2 mg of protein/ml. The photoaffinity ligand was then added to the diluted cytosolic fraction to a final concentration of $3 \times 10^6$ dpm/ml, and the sample was incubated for 30 minutes at 20°. After incubation, the unbound radioligand was removed by the addition of 10 ml of charcoal/gelatin (final concentration, 1:0.1% w/v) in MN buffer, followed by mixing with a vortex mixer (5 seconds) and incubation at 20° for 10 minutes. The charcoal was then removed from suspension by centrifugation at $2000 \times g$ or 10 minutes at 4°. The supernatant was then transferred to clean tubes and the remaining fine particulate charcoal was removed by centrifugation at $10,000 \times g$ for 10 minutes at 4°. The supernatant containing the receptor-radioligand complex was transferred to a 150-ml beaker and irradiated at 310 nm, 80 W, at 4 cm, for 1 minute, to generate the covalently labeled radioligand-receptor complex. After photolysis, $\beta$-mercaptoethanol was added to a final concentration of 10 mM to quench any remaining free radicals. The photoaffinity-labeled fraction was then pooled with the bulk of the cytosol.

Phosphocellulose chromatography.

All ion exchange chromatography was performed in a room maintained at 4°. The photoaffinity-labeled pooled cytosol was brought to 80 mM NaCl and loaded onto a phosphocellulose column (10-cm i.d. $\times$ 14 cm; column volume, approximately 1 liter), with a flow rate of 15 cm/hr. After sample loading was complete, the flow rate was increased to 30 cm/hr and the column was washed with M$\beta$ENG buffer, containing 80 mM NaCl, until the UV absorbance at 280 nm returned to baseline. The Ah receptor was then eluted with M$\beta$ENG buffer plus 225 mM NaCl, with a flow rate of 30 cm/hr. The enriched fraction had a volume of 500 ml.

RP-HPLC.

All RP-HPLC was performed at 56°, using C4 silica-based columns (Vydac 214TP series; The Separations Group, Hesperia, Calif.) in line with catridge precolumns (Hi-Pore Guard C4, 4.6 $\times$ 30 mm; Bio-Rad). The HPLC hardware consisted of two model 510 pumps interfaced with a microprocessor gradient control unit (Waters, Milford, Mass.).

SDS-PAGE, staining, and autoradiography.

The efficiency of photoaffinity labeling and estimation of recoveries and purification factors were determined as follows: 100 $\mu$g of soybean trypsin inhibitor, as carrier protein, were mixed with the labeled sample and precipitated with 9 volumes of ice-cold acetone overnight at 4°. The protein pellet was collected by centrifugation ($2000 \times g$ for 10 minutes), washed with 1 ml of ice-cold acetone/water (9:1), and dissolved in electrophoresis sample buffer. The samples were then subjected to denaturing electrophoresis on discontiuous slab gels (3% stacking gel, 7.5% separating gel; acrylamide/bisacrylamide ratio=37.5:1), at 0.7 mA/cm$^2$ for 16 hours at 4°. Laemmli, U. K., *Nature (Lond).* 227:680–685 (1970). The gels were routinely fixed with methanol/acetic acid. stained with Commassic blue R250 (Chrambach, A., Reisfeld, R. A., Wyckoff, M., Zaccari, J., *Anal. Biochem.* 20:150–154 (1967)) or silver (Heukeshoven, J., and Dernick, R., *Electrophoresis* 6:103–112 (1985)), dried, and placed on top of a sheet of preflashed XAR-5 film (Kodak Chemical Co., Rochester, N.Y.) backed by an intensifying screen (Cronex Lightning Plus, E.I. Dupont de Nemours Inc., Wilmington, Del.), and the film was exposed for a period of 5 to 24 hour at −60° before developing. The 95- and 70-kDa bands were identified in the dried gels by autoradiography and excised, and the radioactivity was quantified by a $\gamma$ scintillation counting.

Protein determination.

Protein concentrations were determined by the method of Warburg and Christian (Warburg, O., and Christian, W., *Biochem. Z.* 310:382–421 (1942)). The protein concentration after electrophoresis and brilliant blue-R staining was quantified by laser scanning densitometry, using phosphorylase b from the molecular weight standard mix as reference protein.

Purification.

Photoaffinity labeling of the Ah receptor average 6400 dpm/mg of protein for the 95-kDa protein and 3800 dpm/mg from the 70-kDa proteolytic product (approximately 2 fmol of photoaffinity ligand bound to receptor/mg of cytosolic protein). Assuming 100 fmol of receptor/mg of protein, this is equivalent to labeling 2% of total receptor. A fraction of the cytosolic protein (1/20th) was routinely labeled and then added back to the bulk of the cytosolic protein, to yield a preparation with a specific activity of 320 to 190 dpm/mg for the 95- and 70-kDa proteins, respectively. After phosphocellulose and DEAE-cellulose chromatography, the specific activity was increased 100-fold, with a recovery of 46%.

Because attempts at further purification of this 100-fold enriched fraction using nondenaturing means were unsuccessful, purification was continued using denaturing conditions. To reduce the protein mass, the 100-fold-enriched material on a preparative RP-HPLC column (2.2-cm i.d. $\times$ 25 cm) with a large particle size (15–20 $\mu$m) was chromatographed. Using a linear gradient of acetonitrile in aqueous TFA (rate of change for acetonitrile=0.18%/cm/min), the 95-kDa receptor species eluted at 51.2% acetonitrile and the 70-kDa species eluted at 52% acetonitrile. Although resolution was inferior to that obtained with smaller particle size columns, use of the preparative column reduced protein approximately 20-fold and provided nearly complete resolution of the 95- and 70-kDa species. After multiple runs on the preparative HPLC column, fractions containing the 95-kDa species were pooled and purified further on a semipreparative column (1-cm i.d. $\times$ 25 cm) with a particle size of 5 $\mu$m. Using a linear gradient of water/n-propanol, with formic acid as a modifier (rate of change for n-propanol=0.1%/cm/min), the 95-kDa receptor eluted as a sharp peak at 26.3% n-propanol.

The final HPLC step was performed on an analytical column (4.6-mm i.d. $\times$ 25 cm) column with a particle size of 5$\mu$m, using a shallow linear gradient of acetonitrile in aqueous TFA (rate of acetonitrile change=0.06/cm/min). The elution of the 95-kDa receptor was monitored by counting the radioactivity present in the fractions and by subjecting an aliquot of each fraction to SDS-PAGE and analysis by silver staining and autoradiography. Fraction 19 contained a peak of radioactivity, but fraction 16 contained the most intense silver-staining ban at 95 kDa. For those fractions that had silver-staining material and significant radioactivity, the autoradiographic signal superimposed exactly over the silver-stained band at 95 kDa. Therefore, it was concluded that the unliganded receptor could be separated from the photoaffinity-labeled Ah receptor under the conditions employed in this final chromatography step.

HPLC fractions that contained the peak of the 95-kDa protein (as determined by silver staining) were pooled, subjected to SDS-PAGE, and electrotransferred to a PVDF membrane. The 95-kDa band was visualized on the membrane by staining with Coomassie blue R250, and the quantity of this protein was estimated by a comparison of staining intensities with known quantities of phosphorylase b. A typical experiment yielded 3-5 μg of the 95-kDa receptor from 10 grams of cytosolic protein. Final recoveries and purification factors were calculated by estimation of the protein in the 95-kDa Coomassie-stained band using laser densitometry. This method indicated a purification factor of 180,000-fold, with an overall recovery of 5%.

The above purification scheme was completed in 3 to 5 working days and yielded a purified Ah receptor of 3 to 5%.

EXAMPLE 2: Nucleotide Sequence of Murine Ah Receptor

Materials and Methods

General Methods:

Cells lines (Hepa1c1c7) were obtained from James P. Whitlock Jr. (Stanford University). Equivalent cell lines are available from the ATCC, catalogue number CRL1830. The Ah-receptor was photoaffinity labeled with [$^{125}$I]-2-azido-3-iodo-7,8-dibromodibenzo-p-dioxin. Poland, A., Glover, E., Ebetino, F. H. & Kende, A. S., *J. Biol. Chem.*, 261:6352-6365 (1986). Rabbit immunoglobulins raised against synthetic peptides corresponding to residues 12-31 and residues 233-250 were prepared and affinity purified. Poland, A., Glover, E. & Bradfield, C. A., *Mol. Pharmacol.* 39:20-6 (1991). The numbering of amino acid residues was determined by counting from the putative initiation methionine, not the true N-terminal residue of the protein (alanine #10) as determined from the amino acid sequencing. Bradfield, C. A., Glover, E. & Poland, i A. Mol. Pharmacol. 39:13-9 (1991).

Detection of the Ah-receptor by Immunochemical Staining and Photoaffinity Labeling.

100 μg of [$^{125}$I]-photoaffinity-labeled cytosolic protein was subjected to denaturing gel electrophoresis (SDS-PAGE) and blotted to nitrocellulose. Blots were immunostained after incubation with anti-N-terminal specific immunoglobulins (μg/ml) and goat anti-rabbit IgG linked to alkaline phosphatase. Poland, A., Glover, E. & Bradfield, C. A., *Mol. Pharmacol* 39:20-6 (1991). The quantity of the photoaffinity labeled receptor was determined after autoradiography by gamma-scintillation counting of the specifically labeled 95 kD bands.

DNA Cloning.

The oligonucleotide probe OL-18 was designed from the amino acid sequence lysine 16-lysine 31. See Sequence ID. 1. The sequence was in the antisense direction and reads 5'TTNATNCCTCTCNGCNG-GNATNGGT/CTTNACNGTT/CTTT/CT-GNACNGGT/CTT3' (SEQUENCE ID. NO. 5). The probe OL-2 was designed from amino acid sequence lysine 16-threonine 21 and reads AAA/GCCNGT-NCAA/GAAA/GAC (SEQUENCE ID. NO. 6). The probe OL-27 was derived from the open reading frame (ORF) of genomic clone described below. OL-27 corresponds to the nucleotides encoding proline 26-proline 34 and reads 5'GGATTTGACTTAATTCCTT-CAGGGG 3' (SEQUENCE ID. NO. 7). A genomic library was constructed in the Lambda FIX II vector and was obtained from STRATAGENE (San Diego, Calif.). The cDNA libraries were constructed in the Lambda ZAP II vector from random primed mRNA obtained from murine Hepa 1c1c7 cells. Short, J. M., Fernandez, J. M., Sorge, J. A. & Huse, W. D., *Nucleic Acids Res.* 16:7583-7600 (1988); Chirgwin, J. M., Przybyla, A. E., MacDonal, R. J. & Rutter, W. J., Biochem. 18:5294-5299 (1979). Library screening with degenerate oligonucleotides and cDNAs was performed. Sambrook, J., Fritsch, E. F., Maniatis, T. *Molecular Cloning: A Laboratory Manual/second edition* (Cold Spring Harbor Laboratory Press, 1989). Nucleotide sequence analysis was performed by the dideoxy-chain termination method. Sanger, F., Nicklen, S and Coulson, A. R., *Proc. Natl. Acad. Sci. USA* 74:5463-5467 (1977).

Northern Blot Analysis.

RNA was located by the method of Chirgwin (Chirgwin, J. M., Przybyla, A. E., MacDonal, R. J. & Rutter, W. J., *Biochem.* 18:5294-5299 (1979)) and samples were run on 0.8% formaldehyde-agarose gels. RNA was transferred to nitrocellulose membranes and hybridized for 16 hours using either the 0.42 kb or the 1.4 kb EcoRI fragment of cAh1 at a specific activity of $1 \times 10^7$ cpm/μg. Sambrook, J., Fritsch, E. F., Maniatis, T. *Molecular Cloning: A Laboratory Manual/second edition* (Cold Spring Harbor Laboratory Press, 1989). Autoradiograms were routinely exposed for 4 days and then stripped and reprobed with a glyceraldehyde phosphate dehydrogenase (GAPD) probe as an internal loading control.

Characterization of the Ah-receptor in Hepa1c1c7 cells and mutants.

Mutants of a murine hepatoma cell line, Hepa 1c1c7 (From James P. Whitlock Jr.), defective in the Ah-receptor signaling pathway, were independently isolated and characterized by two research groups. Miller, A. G., Israel, D., & Whirlock, J. P., *J. Biol. Chem.* 258:3523-3527 (1983); Hankinson, O., *Somatic Cell Genet.* 9:497-514 (1983). These mutant cell lines displayed resistance or altered responses in cytochrome P450IA1 induction after exposure to Ah-receptor agonists. "Class I" mutants have a decreased level of the Ah-receptor. "Class II" mutants have normal Ah-receptor levels, but the Ah-receptor-ligand complex has a lower affinity for the nucleus. Jones, P. B. C., Miller, A. G., Israel, D. I., Galeazzi, D. R. & Whitlock, J. P., *J. Biol. Chem.*, 259:12357-12363 (1984). High activity variant (HAV) cells were also isolated. These cells appeared to have normal levels of the Ah-receptor, but the induction of the cytochrome P450IA1 gene is enhanced due to an altered cis-acting element in the promoter.

To extend proof that the photoaffinity-labeled protein was the Ah-receptor and that the N-terminal amino acid sequence data was specific to that protein, the Hepa 1c1c7 cells and derived mutants were used. See FIG. 1. The wild type, HAV cells and class II mutants show a similar amount of receptor by both methods of detection. In contrast, the class I mutants have a greater than 7-fold reduction in the levels of the Ah-receptor as compared to wild-type cells (quantitated by counting the [$^{125}$I]-photoaffinity label in the 95 kD bands). This result agreed with previous characterizations of these mutant cells in which the level of the Ah-receptor, as measured by radioligand binding, was shown to be decreased. Isreak, D. I., Whitlock, J. P., *J. Biol. Chem.* 258-1039-10394 (1983). This data demonstrates that the photoaffinity ligand specifically binds to the Ah-receptor, it confirms the identity of the purified protein as the Ah-receptor, and provided the N-terminal amino acid sequence for use in the present cloning studies.

CNBr Cleavage and Amino Acid Sequence Analysis of the Purified Ah-Receptor.

500 pmol of the purified Ah-receptor which had been purified from C57BL/6J mouse liver and covalently labeled with [$^{125}$I]-2-azido-3-iodo-7,8-dibromodibenzo-p-dioxin, was dissolved in 100 µl of 70% formic acid. CNBr was added and the cleavage reaction was carried out at room temperature, in the dark, under nitrogen, for 24 hours. The cleavage products were separated by 12% Tricine-SDS-PAGE (Schagger, G. & von Jagow, G., *Anal. Biochem.*, 166:368–379 (1987), electroblotted onto PVDF membranes, and stained with Coomassie blue dye. The major fragments were subjected to N-terminal sequencing on a pulsed liquid phase sequenator. Hewick, R. M., Hunkapillar, M. W., Hood, L. E. & Dryer, W. J., *J. Bicl. Chem.*, 256:7990–7997 (1981).

EXAMPLE 3: Nucleotide Sequence of the Human Ah Receptor

Methods and Materials

General Materials and Methods: Ligand Binding of the Murine and Human Ah-receptors.

Photoaffinity labeling using the ligand, [$^{125}$I]-2-azido-3-iodo-7,8-dibromodibenzo-p-dioxin (specific activity=0.5µCiµl), was carried out in 50µl reactions in MENG buffer. Samples of Ah receptor were incubated with 0.25 µCi of ligand (0.1 pmoles)+/− 100 nM β-naphthoflavone 30 minutes at room temperature, cooled on ice and incubated with one fifth of charcoal/gelatin (3%/0.3% w/v) for 30 minutes on ice. The charocal/gelatin was subjected to centrifugation at 14,000 rpm for 5 minutes at 4° and the supernatant was irradiated with ultraviolet light at 0.8 J/cm$_2$ followed by addition of 300 mM β-mercaptoethanol. Acetone precipitates were resuspended in 1×Laemmli sample buffer and subjected to 7.5% SDS-PAGE and autoradiograph as described in Sambrook, J., Fritsch, E. F., Maniatis, T., *Molecular Cloning: A Laboratory Manual/second edition* (Cold Spring Harbor Laboratory Press, 1989).

Photoaffinity Labeling of Murine Derived Hepa 1c1c7 and Human Derived Hela Cells.

Cytosolic extracts were prepared from nearly confluent cells. The cells were washed twice with PBS, scraped in 10 ml PBS, pelleted at 4°, and resuspended in 500 µl of labeling buffer with (Hela) or without (Hepa) 10 mM sodium molybdate. The cells were homogenized with 30 strokes in a glass homogenizer and subjected to centrifugation at 14,000 rpm for 20 minutes at 4°. The supernatants were centrifuged at 55,000 rpm for 1 hour at 4°. 10 µg of Hepa and 60 µg of Hela cytosol were photoaffinity labeled.

Photoaffinity labeling of murine (muAhR) and human (huAhR) Ah-receptors expressed in COS-1 cells.

Figure 12:
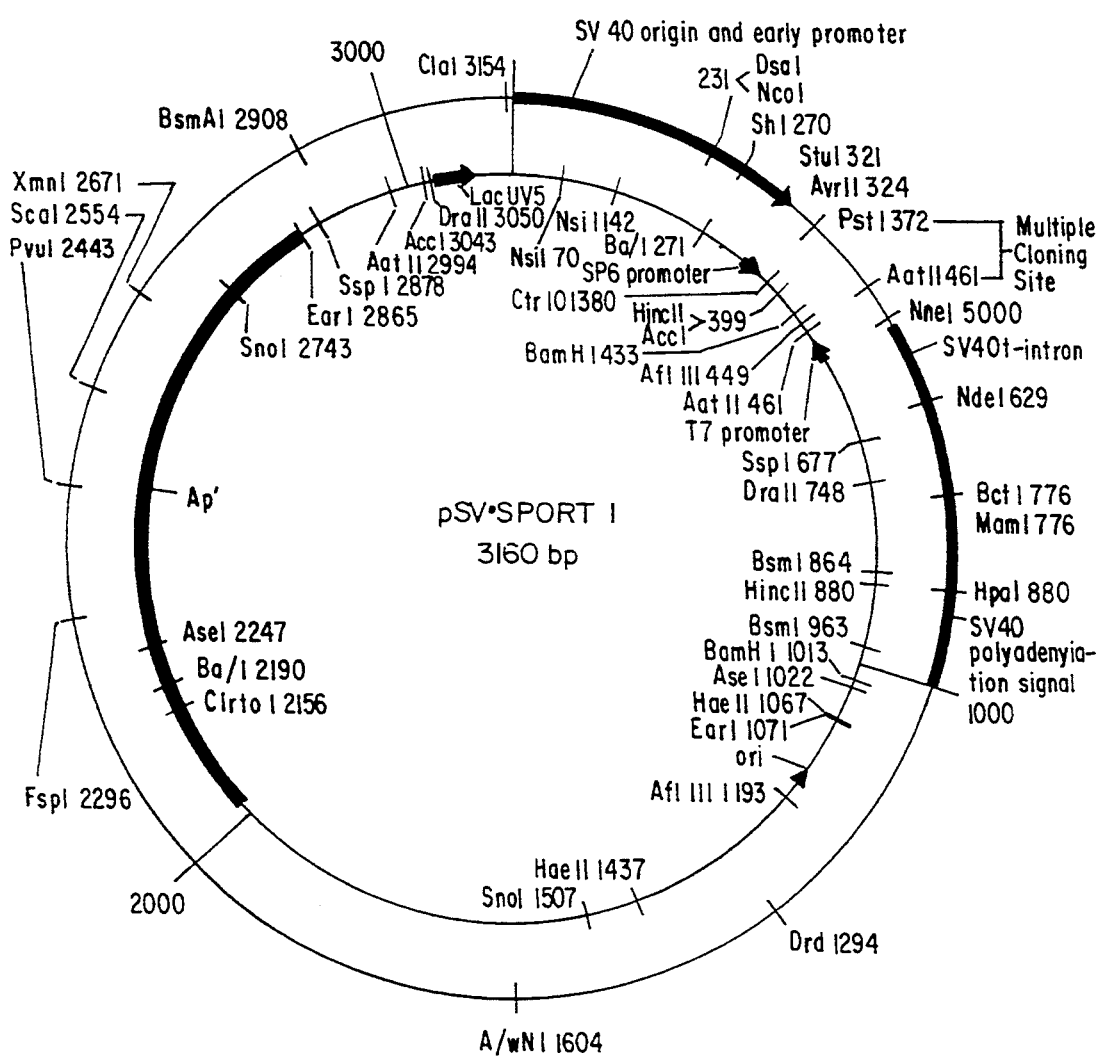
FIG. 12 shows a plasmid map of pSV. Sport1.
Figure 13:
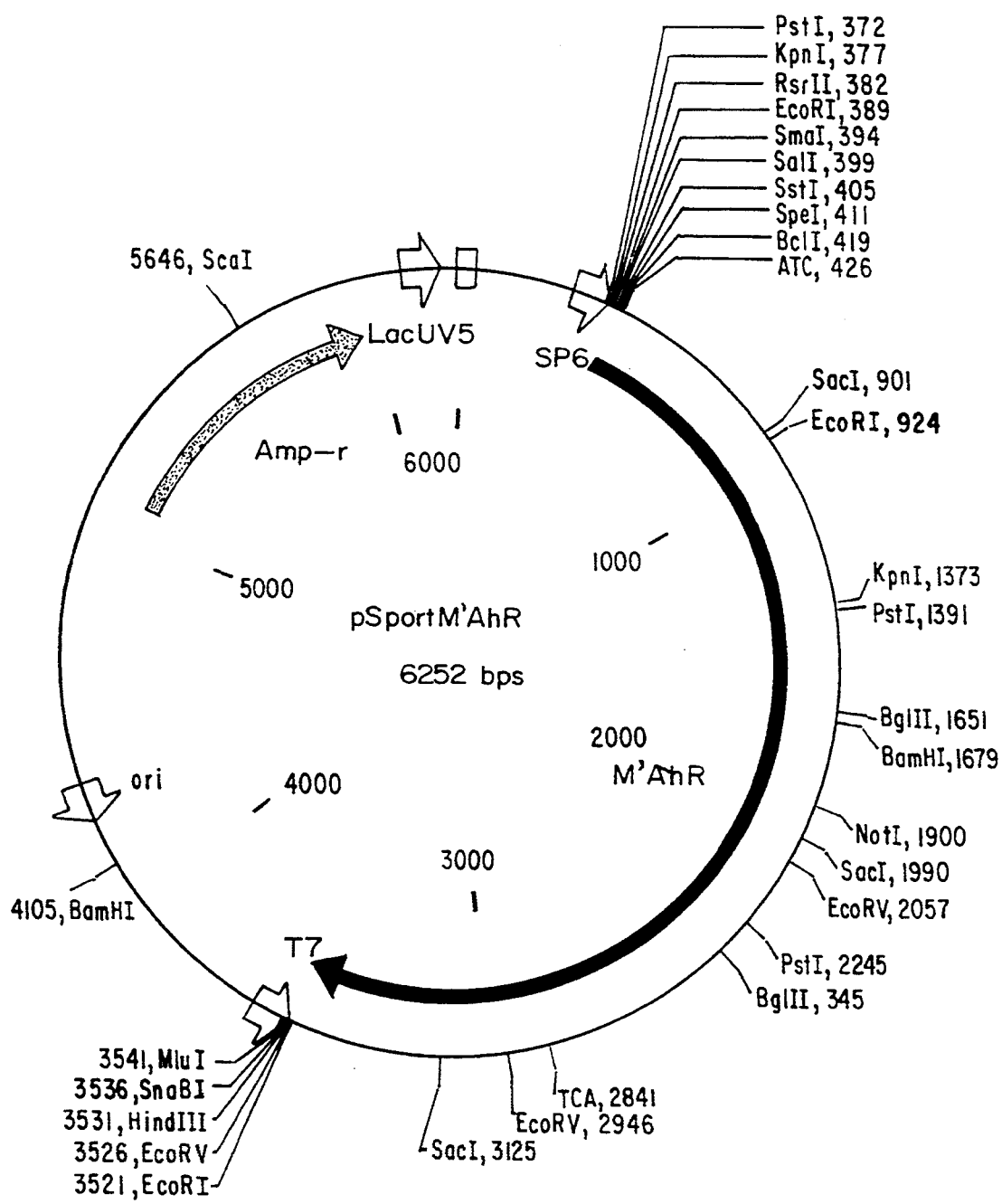
FIG. 13 shows a plasmid map of pSport M'AhR.

The cells were trypsinized, pelleted, and resuspended in DME at a concentration of 4×10$^6$ cells/ml. 20 µg of pmuAhR (See FIG. 12 and Sequence I.D. No. 1 from 1 to 3060) or phuAhR (See FIG. 13 and Sequence I.D. No. 3 from 383 to 2640) plasmid DNA, plus 1.0 µg of pGL-C (luciferase transfection efficiency control, Promga) were added to 700 µl of the cell suspension in 2 mm electroporation cuvettes and incubated 5 minutes on ice. The cells were electroporated at settings of V=150 volts, C=1200 µf, and R=48 ohms and incubated 5 minutes on ice. The cells were added to 20 ml DME. At 24 hours fresh media was added to the cells.

At 72 hours the cells were harvested and cytosolic extracts were prepared as above in the presence of 10 mM sodium molybdate. 60 µg of transfected CCS-1 cytosols were used for photoaffinity labeling. 20 µg of the parent vector, pSV-Sport1, See FIG. 12, were used in control transfections.

Construction of the phuAhR and pmuAhR plasmids.

The plasmid phuAhR was constructed by PCR using OL-135 (5'-GAAGATCTTCCAGTGGTCCCAGC-CTACACC-3' Sequence ID. No. 10.) 81 nucleotides upstream of the initiation methionine and OL-136 (5'-GAAGATCTTCATGTGAACTTGCTGACGTCC-3' Sequence ID. No. 11) 102 nucleotides downstream of the stop codon of the full length human Ah-receptor cDNA clone. The PCR-generated human Ah-receptor was then subcloned into the KpnI and SalI sites of the expression vector, pSV-Sport1 (GIBCO/BRL) and confirmed by DNA sequence analysis. The plasmid pmuAhR was constructed by sequential PCR on the murine clone, cAh1, using OL-55 (5'-GCTCTAGAT-GATCACCATGGTGCAGAAGACCGTGAAGC-CCATCCCCGCTGAAGGAATTAAGTC-3' Sequence ID. No. 12), OL-67 (5'-GCACTAGTTGAT-CACCATGGCCAGCCGCAAGCGGC-GCAAGCCGGTGCAGAAGACCGTGAAGCC-3' Sequence ID. No. 13), and OL-68 (5-GCACTAGTT-GATCACCATGAGCAGCGGCGCCAACAT-CACCTATGCCAGCCGCAAGCGCCGCAAGC -3' Sequence ID. No. 14) as the 5' primes to add the codons for the 25 amino acids (including the initiation methionine) missing from the N-terminus of this clone. The 3' primer, OL-57 (5'GCAGAGTCTGGGTT-TAGAGC-3' Sequence ID. No. 15), was downstream of the internal EcoRI site. The PCR product was then subcloned into the SpeI and EcoRI sites of the pBluescript vector (STRATAGENE) and the 2.6 kb EcoRI fragment containing the remainder of the 3' sequence of the mouse Ah-receptor was cloned into the EcoRI site. The resulting full length murine Ah-receptor clone was then subcloned into the SpeI and HindIII sites of pSV-Sport1.

In vitro transcription and translation of pmuAhR and phuAhR.

Experiments were carried out using the TNT Coupled Reticulocyte Lysate System (PROMEGA). Briefly, 1 µg of plasmid DNA was added to a 50 µl reaction containing 50% TNT rabbit reticulocyte lysate, reaction buffer, 20 µM amino acid mixture minus methionine, 20 µM amino acid mixture minus leucine, 40 units RNasin, 20 units SP RNA polymerase and incubated at 30° for 90 minutes. pSV-Sport1 was used as a labeling control. One fifth of an in vitro reaction was used for photoaffinity labeling. The efficiency of expression was analyzed in parallel experiments utilizing $^{35}$S-methionine labeling and autoradiography and Western blot analysis using affinity-purified goat antibody raised against an N-terminal peptide derived from the murine Ah-receptor. Poland, A., Glover, E., Bradfield, C. A., *Mol. Pharmacol.* 39:20–6 (1991).

Gel shift assays demonstrating binding of Ah-receptor (AhR)-ARNT Heterodimes to DRE3.

A complementary pair of synthetic oligonucleotides, 5'-TCGAGTAGATCACGCAATGGGCCCAGC-3' Sequence ID. No. 16 and 5'-TCGAGCTGGGC-CCATTGCGTGATCTAC-3' Sequence ID. No. 17 (containing DRE3) were annealed and end-labeled with gamma $^{32}$P-labeled deoxyadenosine triphosphate as described. Sambrook, J., Fritsch, E. F., Maniatis, T., *Molecular Cloning: A Laboratory Manual/second edition* (Cold Spring Harbor Laboratory Press, 1989). Cytosolic extracts (35 μg of protein) obtained from either human SCC cells or murine Hepa 1c1c7 cells (From James P. Whitlock Jr.) were incubated in the presence of DMSO (−) or 20 nM TCDD (+) for 2 hours at either room temperature (human) or 30° (murine). Nonspecific competitor, poly dIdC, was added and incubated 15 minutes at room temperature. The radiolabeled probe was then added and incubated 15 minutes at room temperature followed by nondenaturing gel electrophoresis. In vitro translated human AhR and ARNT proteins were incubated with either DMSO (−) or 20 nM TCDD (+) for 2 hours at room temperature followed by gel shift assays as described above. In vitro translated mouse AhR and humanARNT proteins were incubated with either DMSO (−) or 20 nM TCDD (+) for 2 hours at 30° followed by electrophoretic mobility shift assays. Addition of excess competitor wild-type DRE3 (wt) or mutant DRE3 (m), containing two nucleotide substitutions in the core region (Neuhold, L. A., Shirayoshi, Y., Ozato, K., Jones, J. E., Nebert, D. W., *Mol. Cell. Biol.* 9:2378–86 (1989)) demonstrates specificity of complex formation.

Deletion analysis of the human and murine Ah-receptors.

C-terminal deletions were constructed by PCR (CΔ313 and CΔ41]were restriction enzyme fragments utilizing internal NOtI and SpeI sites, respectively) and cloned into the pSV-Sport1 (GIBCO/BRL) expression vector. The oligonucleotides used in PCR for the construction of the deletion mutants were as follows: the human 5′ primer was OL-126, 5′-GCGTCGACTGG-GCACCATGAACAGCAGC-3′ Sequence ID. No. 18, which primed over the initiation methionine; the murine 5′ primer was OL-68 (Sambrook, Fritsch, E. F., Maniatis, T., *Molecular Cloning: A Laboratory Manual/second edition* (Cold Spring Harbor Laboratory Press, 1989)); the 3′ primes for both human and murine deletion mutants were OL-122, 5′-CCCAAGCT-TACGCGTGGTTCTCTGGAG-GAAGCTGGTCTGG-3′ Sequence IDo No. 19 (CΔ636/CΔ599); OL-123, 5′-CCCAAGCT-TACGCGTGGAAGTCTAGCTTGTGTTTGG-3′ Sequence ID. No. 20 (CΔ553/CΔ516); OL-125, 5′-CCCAAGCTTACGCGTGAAGCC-GGAAAACTGTCATGC-3′ Sequence ID. No. 21 (CΔ495/CΔ458); OL-163, 5′-CCCAAGCT-TACGCGTGCAGTGGTCTCTGAGTGGCGAT-GATGTAATCTGG-3′ Sequence ID. No. 22 (CΔ462/CΔ425); OL-124, 5′-CCCAAGCT-TACGCGTGGTCTTTGAAGTCAACCTCACC-3′ Sequence ID. No. 23 (CΔ274/CΔ237). All PCR was carried out using the high fidelity Pfu DNA polymerase (STRATAGENE) and the sequencing of more than 4.0 kb has yielded no PCR-induced mutations. In addition, the fact that two separate clones of each deletion mutant (human and murine) produced similar results supports the fidelity of the PCR-generated deletion mutants.

All 3′ primers were designed against the murine cDNA. Position of primers was based on preliminary structural analysis of protein encoded by murine Ah-receptor cDNA. N-terminal deletions representing chimeric proteins consisting of the Ah-receptor and the DNA binding domain of the yeast Gal4 protein were constructed first in the pSG424 vector (Sadowski, I., Ptashne, M., *Nucleic Acids Research* 17:7539 (1989)) and then subcloned into the pGEM-7Zf vector (PROMEGA).

EXAMPLE 4: Use of cDNA Ah Receptor in an Assay

Figure 7:
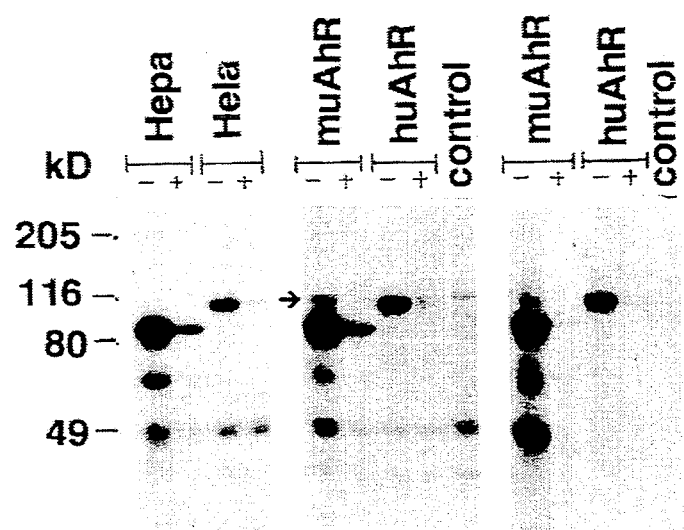
FIG. 7 shows the ligand binding of the murine and Ah receptors.
Figure 8A:
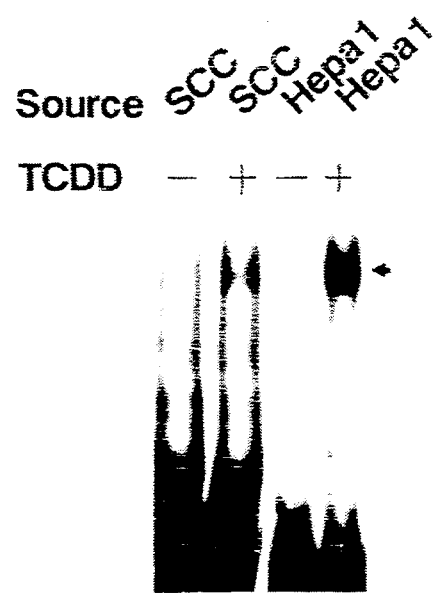
FIGS. 8A, 8B, and 8C shows gel shift assays demonstrating binding of Ah receptor (AhR)-ARNT heterodimers to DRE3.
Figure 8B:
Figure 8C:
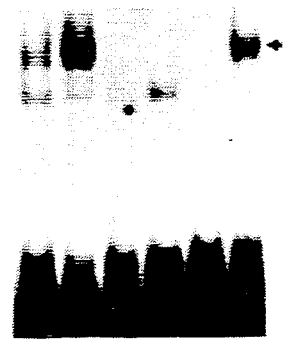

To determine if in vitro models could be developed to characterize the functional domains of the Ah-receptor, both murine and human cDNAs in COS-1 cells were expressed and photoaffinity labeled the cytosolic fractions from the transfectants with [$^{125}$I]-2-azido-3-iodo-7,8-dibromodibenzo-p -dioxin. Poland, A., Glover, E., Ebetiono, F. H., and Kende, A. S., *J. Biol. Chem.* 261:6352–6365 (1986). To demonstrate specificity of ligand binding, the reactions were performed in the presence of an excess of the receptor agonist β-naphthoflavone, which inhibited the labeling of the receptors. See FIG. 7. Since the Ah-receptor and ARNT are constitutively expressed in COS-1 cells (See FIG. 7) cDNA expression in a reticulocyte lysate system was used. Both the human and mouse receptors were specifically labeled with the photoaffinity ligand. See FIG. 7. Despite its structural similarity to the Ah-receptor, ARNT does not bind the photoaffinity ligand under the conditions used to label the receptor nor under conditions of 5-fold excess radioligand. Hoffman, E. C., et al., *Science* 252:954–8 (1991). Also, ligand binding is independent of ARNT, as ligand binding is independent of the presence or absence of ARNT. The DNA binding properties of these translated receptors were examined by employing gel shift assays using a synthetic oligonucleotide corresponding to a well characterized DRE. Dension, M. S., Fisher, J. M., Whitlock, J. P., *J. Biol. Chem.* 264:16478–16482 (1989). Cytosolic extracts from human and murine cells were shown to interact with the DRE in a ligand dependent manner. See FIG. 8A, 8B & 8C. Similarly, in the presence of ARNT, the in vitro expressed human and murine receptors bound to the DRE upon ligand activation. See FIG. 8A, 8B & 8C. The specificity of DRE-binding was demonstrated by competition experiments using an excess of unlabeled DRE oligonucleotide or an oligonucleotide containing a mutated DRE. This demonstrates that both the Ah-receptor and ARNT are required for DNA binding, since neither protein was able to bind to the DRE alone.

Although the invention has been described in terms of the specific embodiments many modifications and variations of the present invention are possible in light of the teachings. It is, therefore, to be understood that within the scope of the appended claims the invention may be practiced otherwise than as specifically described.

We claim:

1. An isolated nucleic acid encoding the murine Ah receptor whose amino acid sequence is defined by SEQ ID NO. 2.

2. The nucleic acid of claim 1 wherein said nucleic acid has the nucleotide sequence set out in SEQ ID NO. 1.

3. An isolated nucleic acid encoding the human Ah receptor, whose amino acid sequence is defined by SEQ ID NO. 4.

4. The nucleic acid of claim 3 wherein said nucleic acid has the nucleotide sequence set out in SEQ ID NO. 3.

* * * * *

UNITED STATES PATENT AND TRADEMARK OFFICE
CERTIFICATE OF CORRECTION

PATENT NO. : 5,378,822
DATED : January 3, 1995
INVENTOR(S) : Bradfield et al.

It is certified that error appears in the above-indentified patent and that said Letters Patent is hereby corrected as shown below:

On the title page:

Under "Assignee" delete -- "Wisconsin Alumni Research, Evanston Ill; Northwestern University and Foundation, Madison, Wis." and insert -- Northwestern University, Evanston, Ill.; Wisconsin Alumni Research Foundation, Madison, Wis. --.

Signed and Sealed this

Thirteenth Day of June, 1995

BRUCE LEHMAN

*Attest:*

*Attesting Officer*   *Commissioner of Patents and Trademarks*